(12) United States Patent
Ameri et al.

(10) Patent No.: US 11,660,265 B2
(45) Date of Patent: May 30, 2023

(54) METHOD OF RAPIDLY ACHIEVING THERAPEUTIC CONCENTRATIONS OF TRIPTANS FOR TREATMENT OF MIGRAINES AND CLUSTER HEADACHES

(71) Applicant: ZP Opco, Inc., Fremont, CA (US)

(72) Inventors: Mahmoud Ameri, Fremont, CA (US); Donald Kellerman, Santa Cruz, CA (US); Peter E. Daddona, Menlo Park, CA (US); Yi Ao, Palo Alto, CA (US); Peter C. Schmidt, Menlo Park, CA (US)

(73) Assignee: Emergex USA Corporation, Doylestown, PA (US)

( * ) Notice: Subject to any disclaimer, the term of this patent is extended or adjusted under 35 U.S.C. 154(b) by 513 days.

(21) Appl. No.: 16/454,474

(22) Filed: Jun. 27, 2019

(65) Prior Publication Data
US 2020/0000712 A1    Jan. 2, 2020

Related U.S. Application Data

(60) Provisional application No. 62/691,502, filed on Jun. 28, 2018.

(51) Int. Cl.
*A61M 37/00* (2006.01)
*A61K 9/00* (2006.01)
(Continued)

(52) U.S. Cl.
CPC .......... *A61K 9/0021* (2013.01); *A61K 31/422* (2013.01); *A61M 37/0015* (2013.01);
(Continued)

(58) Field of Classification Search
CPC .. A61K 9/0021; A61K 31/422; A61K 9/0019; A61K 9/0043; A61K 9/0056;
(Continued)

(56) References Cited

U.S. PATENT DOCUMENTS

| 5,080,646 A | 1/1992 | Theeuwes et al. |
| 5,147,296 A | 9/1992 | Theeuwes et al. |

(Continued)

FOREIGN PATENT DOCUMENTS

| DE | 10314617 A1 | 10/2004 |
| EP | 0914178 B1 | 1/2003 |

(Continued)

OTHER PUBLICATIONS

Lui, Chao ad Fang, Liang, Drug in Adhesive Patch of Zolitriptan: Formulation and In vitro/In vivo Correlation, 2015, AAPS PharmSciTech, vol. 16, No. 6, pp. 1245-1253. (Year: 2015).*

(Continued)

*Primary Examiner* — Amber R Stiles
(74) *Attorney, Agent, or Firm* — Mayer Brown LLP

(57) ABSTRACT

Compositions, devices and methods employing therapeutic concentrations of a triptan for treatment of migraine are described. Also described are methods for treating migraine by administering zolmitriptan using an adhesive dermally-applied microarray (ADAM) resulting in rapid and durable pain relief, pain freedom and reduction in most bothersome migraine-associated symptoms (MBS), or a combination thereof.

21 Claims, 26 Drawing Sheets
(26 of 26 Drawing Sheet(s) Filed in Color)

(51) Int. Cl.
*A61K 31/422* (2006.01)
*A61P 25/06* (2006.01)
*B05D 1/18* (2006.01)

(52) U.S. Cl.
CPC ...... *A61P 25/06* (2018.01); *A61M 2037/0023* (2013.01); *A61M 2037/0053* (2013.01); *A61M 2037/0061* (2013.01); *B05D 1/18* (2013.01)

(58) Field of Classification Search
CPC ...... A61M 37/0015; A61M 2037/0023; A61M 2037/0053; A61M 2037/0061; A61P 25/06; B05D 1/18
See application file for complete search history.

(56) References Cited

U.S. PATENT DOCUMENTS

| | | | |
|---|---|---|---|
| 5,169,382 | A | 12/1992 | Theeuwes et al. |
| 5,169,383 | A | 12/1992 | Gyory et al. |
| 5,738,728 | A | 4/1998 | Tisone |
| 5,741,554 | A | 4/1998 | Tisone |
| 5,743,960 | A | 4/1998 | Tisone |
| 5,916,524 | A | 6/1999 | Tisone |
| 6,050,988 | A | 4/2000 | Zuck |
| 6,083,196 | A | 7/2000 | Trautman et al. |
| 6,091,975 | A | 7/2000 | Daddona et al. |
| 6,322,808 | B1 | 11/2001 | Trautman et al. |
| 6,855,131 | B2 | 2/2005 | Trautman et al. |
| 6,855,372 | B2 | 2/2005 | Trautman et al. |
| 6,953,589 | B1 | 10/2005 | Trautman et al. |
| 7,087,035 | B2 | 8/2006 | Trautman et al. |
| 7,097,631 | B2 | 8/2006 | Trautman et al. |
| 7,131,960 | B2 | 11/2006 | Trautman et al. |
| 7,184,826 | B2 | 2/2007 | Cormier et al. |
| 7,419,481 | B2 | 9/2008 | Trautman et al. |
| 7,435,299 | B2 | 10/2008 | Trautman et al. |
| 7,537,795 | B2 | 5/2009 | Cormier et al. |
| 7,556,821 | B2 | 7/2009 | Ameri et al. |
| 7,798,987 | B2 | 9/2010 | Trautman et al. |
| 7,963,935 | B2 | 6/2011 | Cormier et al. |
| 7,973,058 | B2 | 7/2011 | Anderson et al. |
| 8,361,022 | B2 | 1/2013 | Ameri et al. |
| 8,633,159 | B2 | 1/2014 | Ameri et al. |
| 8,663,155 | B2 | 3/2014 | Cormier et al. |
| 8,753,318 | B2 | 6/2014 | Trautman et al. |
| 9,192,749 | B2 | 11/2015 | Trautman et al. |
| 9,272,137 | B2 | 3/2016 | Anderson et al. |
| 9,295,714 | B2 | 3/2016 | Ameri et al. |
| 9,387,315 | B2 | 7/2016 | Trautman et al. |
| 9,421,351 | B2 | 8/2016 | Trautman et al. |
| 9,782,344 | B2 | 10/2017 | Ameri et al. |
| 9,918,932 | B2 * | 3/2018 | Ameri ............... A61K 31/422 |
| 10,342,963 | B2 | 7/2019 | Cao et al. |
| 11,058,630 | B2 * | 7/2021 | Ameri ............... A61K 31/422 |
| 2002/0123675 | A1 | 9/2002 | Trautman et al. |
| 2006/0177494 | A1 | 8/2006 | Cormier et al. |
| 2007/0173536 | A1 | 7/2007 | Van Der Schaaf et al. |
| 2008/0039775 | A1 | 2/2008 | Ameri et al. |
| 2008/0213461 | A1 | 9/2008 | Gill et al. |
| 2009/0252791 | A1 | 10/2009 | Sreedharala et al. |
| 2011/0144159 | A1 | 6/2011 | Fay et al. |
| 2013/0064868 | A1 | 3/2013 | Okazaki et al. |
| 2013/0064875 | A1 | 3/2013 | Okazaki et al. |
| 2015/0038897 | A1 | 2/2015 | Daddona et al. |
| 2016/0074644 | A1 | 3/2016 | Cao et al. |
| 2017/0239174 | A1 | 8/2017 | Ameri et al. |
| 2018/0153798 | A1 | 6/2018 | Ameri et al. |
| 2018/0153799 | A1 | 6/2018 | Ameri et al. |
| 2019/0070103 | A1 * | 3/2019 | Ameri ............... A61K 9/7023 |
| 2020/0000712 | A1 | 1/2020 | Ameri et al. |
| 2021/0275445 | A1 * | 9/2021 | Ameri ............... A61K 31/422 |

FOREIGN PATENT DOCUMENTS

| | | | |
|---|---|---|---|
| EP | 2570115 | A1 | 3/2013 |
| EP | 2829265 | A2 | 1/2015 |
| EP | 3251722 | A1 | 12/2017 |
| EP | 3035952 | B1 | 12/2018 |
| JP | 2007511508 | A | 5/2007 |
| JP | 2007527392 | A | 9/2007 |
| JP | 2009509634 | A | 3/2009 |
| JP | 2013177376 | A | 9/2013 |
| JP | 2016014028 | A | 1/2016 |
| TW | 201620508 | A | 6/2016 |
| WO | 00/44438 | A1 | 8/2000 |
| WO | 2005004842 | A2 | 1/2005 |
| WO | 2005051456 | A2 | 6/2005 |
| WO | 2005115360 | A2 | 12/2005 |
| WO | 2007040938 | A1 | 4/2007 |
| WO | 2008115586 | A1 | 9/2008 |
| WO | WO-2008115586 | A1 * | 9/2008 ........... A61K 9/0021 |
| WO | 2010074239 | A1 | 7/2010 |
| WO | 2011046927 | A1 | 4/2011 |
| WO | 2012075209 | A1 | 6/2012 |
| WO | 2014058746 | A1 | 4/2014 |
| WO | 2014078545 | A1 | 5/2014 |
| WO | 2014193727 | A1 | 12/2014 |
| WO | 2017/079611 | A1 | 5/2017 |
| WO | 2017143345 | A1 | 8/2017 |
| WO | 2019/040063 | A1 | 2/2019 |

OTHER PUBLICATIONS

Lui, Chao and Fang, Liang, Drug in Adhesive Patch of Zolitriptan: Formulation and In vitro/In vivo Correlation, 2015, AAPS Pharm Sci Tech, vol. 16, No. 6, pp. 1245-1253. (Year: 2015).*
Alhalaweh et al, "Preparation of zolmitriptan-chitosan microparticles by spray draying for nasal delivery," European Journal of Pharmaceutical Sciences, 2009, pp. 206-214, vol. 38.
Ashina et al, "Intravenous treatment of migraine, Techniques in Regional Anesthesia and Pain Management," 2012, pp. 25-29, vol. 16.
Carl G.H. Dahlof, "Non-oral formulations of Triptans and Their Use in Acute Migraine," Current Pain and Headache Reports, 2005, pp. 206-212, vol. 9.
Derry et al, "Sumatriptan (all routes of administration) for acute migraine attacks in adults—overview of Cochrane reviews (Review)", 2014, Issue 5.
Fernandez et al, "Sumatriptan Succinate Transdermal Delivery Systems for the Treatment of Migraine," Journal of Pharmaceutical Sciences, Jun. 2008, 2102-2108, vol. 97, No. 6.
Girotra et al, "Development of zolmitriptan loaded PLGA/polozamer nanoparticles for migraine using quality by design approach," International Journal of Biological Macromolecules, 2016, pp. 92-101, vol. 85.
Ikemoto et al, "Rizatriptan (Maxalt), a new entity of triptan for migraine: pharmacology and therapeutic relevance," Folia Pharmacologica Japonica, The Japanese Pharmacological Society, 2004, pp. 295-302, vol. 123, Iss. 4.
Jhee et al, "Pharmacokinetics and Pharmacodynamics of the Triptan Antimigraine agents: A Comparative Review," Clin. Pharmacokinet., 2001, pp. 190-205, vol. 40, Issue 3.
Kumar et al, "Optimization of combinational intranasal drug delivery system for the management of migraine by using statistical design," European Journal of Pharmaceutical Sciences, 2015, pp. 140-151, vol. 70.
Liu et al, "Drug in Adhesive Patch of Zolmitriptan: Formulation and In vitro/In Vivo Correlation," AAPS PharmSciTech, 2015, pp. 1245-1253, vol. 16, No. 6.
Pascual et al, "Effect of iontophoresis on in vitro transdermal absorption of almotriptan," International Journal of Pharmaceutics, 2011, pp. 189-194, vol. 416.
Patel et al, "Controlled non-invasive transdermal iontophoretic delivery of zolmitriptan hydrochloride in vitro and in vivo," European Journal of Pharmaceutics and Biopharmaceutics, 2009, pp. 304-309, vol. 72.

(56) References Cited

OTHER PUBLICATIONS

Olivia J. Phung, "Orally inhaled dihydroergotamine: A novel ergot delivery method for the treatment of migraine," Formulary Journal, Feb. 2012, pp. 54-57, vol. 47, Issue 2.
Mark W. Pierce, "Transdermal Delivery of Sumatriptan for the Treatment of Acute Migraine," Neurotherapeutics: The Journal of the American Society for Experimental Neurotherapeutics, 2010, pp. 159-163, vol. 7, No. 2.
Shrewsbury et al, "Safety and pharmacokinetics of dihydroergotamine mesylate administered via a Novel (Tempo) inhaler," Headache, Mar. 2008, pp. 355-367, vol. 48, Issue 3.
Subedi et al, "Influence of formulation variables in transdermal drug delivery system containing zolmitriptan," International Journal of Pharmaceutics, 2011, pp. 209-214, vol. 419, Issues 1-2.
Tepper et al, "MAP0004, Orally Inhaled Dihhydroergotamine for Acute Treatment of Migraine: Efficacy of Early and Late Treatments," Mayo Clinic Proceedings, 2011, pp. 948-955, vol. 86, Issue 10.
Wang et al, "Uptake and biodistribution of rizatriptan to blood and brain following different routes of administration in rats," International Journal of Pharmaceutics, 2007, pp. 155-160, vol. 337.
Warnken et al, "Formulation and Device Design to Increase Nose to Brain Drug Delivery," Journal of Drug Delivery Science and Technology, 2016, pp. 213-222, vol. 35.
Wu et al., "Development of a novel transdermal patch containing sumatriptan succinate for the treatment of migraine: in vitro and in vivo characterization," J. Drug Del. Sci. Tech., 2014, pp. 695-701, vol. 24, Issue 6.
Diener et al, "Latest Literature on the Pathophysiology and Treatment of Headaches," Headache News, 2015.
Halker et al, "Total Migraine Freedom for Breath Powered Intranasal Delivery of 22 mg Sumatriptan Powder (AVP-825) Versus 100 mg Oral Sumatriptan from the Compass Study of Acute Treatment of Migraine," Abstract, Value in Health, May 2015, vol. 18, Issue 3, p. A278 at Item PND7.
Schulman et al, "Faster migraine pain and disability relief using AVP-825 compared to Sumatriptan tablet: applying a novel method for evaluating migraine relief across multiple outcomes," Abstract, The Journal of Pain, Apr. 2016, vol. 17, Issue 4, pp. S93-S94 at Item 478.
Seaber et al., "The absolute bioavailability and metabolic disposition of the novel antimigraine compound zolmitriptan (311C90)," Br. J Clin. Pharmacol., 1997; 43: 579-587.
Asseburg et al, "Cost-effectiveness of oral triptans for acute migraine: Mixed treatment comparison," International Journal of Technology Assessment in Health Care, 2012, pp. 382-389, vol. 28.
L. Kelman, "Review of frovatriptan in the treatment of migraine," Neuropsychiatr Dis Treat., 2008, pp. 49-54, vol. 4, Issue 1.
Ameri et al, "Parathyroid hormone PTH(1-34) formulation that enables uniform coating on a novel transdermal microprojection delivery system," Pharmaceutical Research, 2010, pp. 303-313, vol. 27.
Ameri et al, "Effect of irradiation on parathyroid hormone PTH(1-34) coated on a novel transdermal microprojection delivery system to produce a sterile product—adhesive compatibility," Journal of Pharmaceutical Studies, 2010, pp. 2123-2134, vol. 99.
Barnes et al, "An Introduction to Rheology," Elsevier, 1989, New York.
"Draft Guidance for Industry Migraine: Developing Drugs for Acute Treatment," U.S. Food and Drug Administration: Center for Drug Evaluation and Research, Oct. 2014.
Evers et al, EFNS guideline on the drug treatment of migraine-revised report of an EFNS task force, Eur. J. Neurol. ;2009), vol. 16, Issue 9, p. 968-981.
Avanir Pharmaceuticals, ONZETRA Xsail Package Insert (2016).
Impax Pharmaceuticals, Zomig package insert (2015).
Ferrari et al, Triptans (serotonin, 5-HT1B/1D agonists) in migraine: detailed results and methods of a meta-analysis of 53 trials, Cephalagia (2002), vol. 22, Issue 8, p. 633-658.
Rosenzweig et al., "The placebo effect in healthy volunteers: influence of experimental conditions on physiological parameters during phase I studies," Br. J. clin. Pharmac., 1995; 39, p. 657-664.
Seaber et al., "The absolute bioavailability and effect of food on the pharmacokinetics of zolmitriptan in healthy volunteers," Br. J. Clin. Pharmacol., 1998; 46: 433-439.
Impax Pharmaceuticals, Zomig package insert (2012).
Zosano Pharma, Press Release, Zosano Pharma Announces Notice of Allowance for a U.S. Patent Application Covering M207 as an Acute Treatment for Migraine (Jan. 3, 2018), available at http://ir.zosanopharma.com/news-releases/news-release-details/zosano-pharma-announces-notice-allowance-us-patent-application?ReleaseID=1053173.
Zosano Pharma, Press Release, Zosano Reaches Enrollment Milestone in M207-ADAM Long-term Safety Study (Mar. 16, 2018), available at http://ir.zosanopharma.com/news-releases/news-release-details/zosano-reaches-enrollment-milestone-m207-adam-long-term-safety.
Zosano Pharma, Press Release, Zosano Reaches Another Enrollment Milestone in M207-ADAM Long-term Safety Study (May 14, 2018), available at http://ir.zosanopharma.com/news-releases/news-release-details/zosano-reaches-another-enrollment-milestone-m207-adam-long-term.
Dodick et al, Use of Most Bothersome Symptom as a Coprimary Endpoint in Migraine Clinical Trials: A Post-Hoc Analysis of the Pivotal ZOTRIP Randomized, Controlled Trial, Headache (2018) vol. 58: p. 986-992.
Zosano Pharma, Press Release, Zosano Announces Publication of Most Bothersome Symptom Data from the ZOTRIP Pivotal Study in Headache: The Journal of Head and Face Pain (May 23, 2018), available at http://ir.zosanopharma.com/news-releases/news-release-details/zosano-announces-publication-most-bothersome-symptom-data-zotrip.
Ameri et al, Effect of Skin Model on In Vitro Performance of an Adhesive Dermally Applied Microarray Coated with Zolmitriptan, Journal of Pharmaceutics, (2018), p. 1-5.
Nguyen et al, Pharmacokinetics and Skin Tolerability of Intracutaneous Zolmitriptan Delivery in Swine Using Adhesive Dermally Applied Microarray, (2018), J. Pharm. Sci., 107: p. 2192-2197.
Zosano Pharma, Press Release, Zosano Announces Publication on Adhesive Dermally-Applied Microarray (ADAM) Technology for the Delivery of Zolmitriptan in Migraine in Journal of Pharmaceutics, (Jun. 20, 2018), available at http://ir.zosanopharma.com/news-releases/news-release-details/zosano-announces-publication-adhesive-dermally-applied.
Zosano Pharma, Press Release, Zosano to Present Additional Analyses from the ZOTRIP Pivotal Study on Pain Relief and Recurrence at the 2018 American Headache Society (AHS) Meeting, (Jun. 27, 2018), available at http://ir.zosanopharma.com/index.php/news-releases/news-release-details/zosano-present-additional-analyses-zotrip-pivotal-study-pain.
Zosano Pharma, Abstract from Presentation, Pharmacokinetics and Tolerability of a New Intracutaneous Microneedle System of Zolmitriptan (ZP-Zolmitriptan), (Jun. 9, 2016).
Zosano Pharma, Press Release, Zosano Announces Publication of Positive Phase 1 Data of Zolmitriptan Delivery in Future Medicine's Pain Management Journal, (Jul. 31, 2017), available at http://ir.zosanopharma.com/news-releases/news-release-details/zosano-announces-publication-positive-phase-1-data-zolmitriptan.
Zosano Pharma, Press Release, Zosano Pharma Announces US Patent Office Publication of "Method of Rapidly Achieving Therapeutic Concentrations of Triptans for Treatment of Migraines," (Aug. 28, 2017), available at http://ir.zosanopharma.com/news-releases/news-release-details/zosano-pharma-announces-us-patent-office-publication-method?ReleaseID=1038367.
Zosano Pharma, Press Release, Zosano Announces Publication of Pivotal Data of ADAM Zolmitriptan for the Acute Treatment of Migraine in Cephalalgia, (Oct. 12, 2017), available at http://ir.zosanopharma.com/news-releases/news-release-details/zosano-announces-publication-pivotal-data-adam-zolmitriptan?ReleaseID=1043757.
Spierings et al, "Randomized, double-blind, placebo-controlled, parallel-group, multi-center study of the safety and efficacy of ADAM

(56) References Cited

OTHER PUBLICATIONS zolmitriptan for the acute treatment of migraine", (2018) (e-published Oct. 12, 2017) Cephalalgia, 38 (2): p. 215-224.
Zosano Pharma, Press Release, Zosano Pharma Announces Initiation of Long-Term Safety Study for M207 as an Acute Treatment of Migraine, (Nov. 8, 2017), available at http://ir.zosanopharma.com/news-releases/news-release-details/zosano-pharma-announces-initiation-long-term-safety-study-m207?ReleaseID=1047756.
ClinicalTrials.gov—"Safety and Efficacy of ZP-Zolmitriptan Intracutaneous Microneedle Systems for the Acute Treatment of Migraine (Zotrip)", available at: https://clinicaltrials.gov/ct2/show/NCT02745392?term=zosano&rank=4.
ZosanoPharma, Corporate Presentation, May 2016 (28 pages).
"Zosano Pharma Reports Fourth Quarter and Fiscal 2016 Financial Results and Business Update," Mar. 1, 2017 (4 pages).
Zosano Pharma, "Zosano to Present Migraine Data at Three Industry-Leading Conferences," Jun. 1, 2017 (2 pages), available at: http://ir.zosanopharma.com/news-releases/news-release-details/zosano-present-migraine-data-three-industry-leading-conferences?ReleaseID=1028620.
Presentation: "Randomized, Double-blind, Multi-center, Parallel-group, Evaluation of the Safety and Efficacy of ADAM Zolmitriptan for the Acute Treatment of Migraine," Jun. 16, 2017.
Zosano Pharma, "Zosano Presents Data from ZOTRIP Study at International Headache Society," (Sep. 13, 2017), available at: http://ir.zosanopharma.com/news-releases/news-release-details/zosano-presents-data-zotrip-study-international-headache-society?ReleaseID=1040290.
ClinicalTrials.gov—"A Study to Evaluate the Long-Term Safety of M207 in the Acute Treatment of Migraine (ADAM)", available at: https://clinicaltrials.gov/ct2/show/NCT03282227?term=zosano.
Zosano Pharma, "Zosano Provides Patent Application Update" (Sep. 26, 2017), available at: http://ir.zosanopharma.com/news-releases/news-release-details/zosano-provides-patent-application-update? ReleaseID=1041740.
File History of U.S. Appl. No. 15/438,455 (not submitted herewith).
Zosano Pharma—Corporate Overview, Jan. 2018 (37 pages).
The Migraine World Summit; Notes on Dr. Goadsby; available at: https://www.migraineworldsummit.com/public-peter-goadsby/.
Zosano Pharma—Press Release: Zosano announces positive data from a nonclinical evaluation of pharmacokinetics and skin tolerability study for ADAM technology for the delivery of zolmitriptan (Jul. 17, 2018) available at http://ir.zosanopharma.com/news-releases/news-release-details/zosano-announces-positive-data-nonclinical-evaluation.
Zosano Pharma—Press Release: Zosano Pharma and Collaborators to Present Efficacy Data for M207 in the Treatment of Migraine at the 17th Biennial Migraine Trust International Symposium (MTIS) (Sep. 5, 2018) available at http://ir.zosanopharma.com/news-releases/news-release-details/zosano-pharma-and-collaborators-present-efficacy-data-m207.
Zosano Pharma—Press Release: Zosano Pharma to Present Phase 3 Safety Study Update for ADAM Technology in the Delivery of Zolmitriptan at the 5th Annual Transdermal & Intradermal Drug Delivery Systems Conference (Sep. 6, 2018) available at http://ir.zosanopharma.com/news-releases/news-release-details/zosano-pharma-present-phase-3-safety-study-update-adamtm.
Zosano Pharma—Press Release: Zosano Pharma Completes Manufacture of M207 Registration Batches (Sep. 19, 2018) available at: http://ir.zosanopharma.com/news-releases/news-release-details/zosano-pharma-completes-manufacture-m207-registration-batches.
Zosano Pharma—Press Release: Zosano Pharma Engages Contract Manufacturer as Part of the Commercialization Strategy for M207 (Oct. 3, 2018) available at: http://ir.zosanopharma.com/news-releases/news-release-details/zosano-pharma-engages-contract-manufacturer-part.
Zosano Pharma—Press Release: Zosano Pharma to Host Key Opinion Leader Meeting on New Treatments for Migraine and the Migraine Patients' Perspective (Oct. 18, 2018) available at: http://ir.zosanopharma.com/news-releases/news-release-details/zosano-pharma-host-key-opinion-leader-meeting-new-treatments.
Zosano Pharma—Press Release: Zosano Treats over 4,000 Migraines and Reaches an Important Goal in M207-ADAM Long-term Safety Study (Oct. 23, 2018) available at: http://ir.zosanopharma.com/news-releases/news-release-details/zosano-treats-over-4000-migraines-and-reaches-important-goal.
Zosano Pharma—Zosano Press Release re FDA: Zosano Receives Conditional FDA Acceptance of Proposed Brand Name Qtrypta for M207(Dec. 12, 2018) available at: http://ir.zosanopharma.com/news-releases/news-release-details/zosano-receives-conditional-fda-acceptance-proposed-brand-name.
Zosano Pharma—Press Release: Zosano Announces Publication of Positive Data on Qtrypta's Potential as an Acute Treatment for Patients with Difficult to Treat Migraines (Jan. 31, 2019) available at: http://ir.zosanopharma.com/news-releases/news-release-details/zosano-announces-publication-positive-data-qtryptastm-potential.
Tepper et al., "Efficacy of ADAM Zolmitriptan for the Acute Treatment of Difficult-to-Treat Migraine Headaches," Headache, (2019); 59(4), pp. 509-517.
Zosano Pharma—Press Release: Zosano Announces Completion of the Final Milestone in the Long-Term Safety Study of Qtrypta for the Acute Treatment of Migraine Disease (Feb. 21, 2019) available at: http://ir.zosanopharma.com/news-releases/news-release-details/zosano-announces-completion-final-milestone-long-term-safety.
Zosano Pharma—Press Release: Zosano Pharma Announces Presentation and Participation at the 31st Annual Roth Conference (Mar. 11, 2019) available at: http://ir.zosanopharma.com/news-releases/news-release-details/zosano-pharma-announces-presentation-and-participation-31st.
Zosano Pharma—Press Release: Zosano Announces the Publication of an Analysis of Acute Treatments for Migraine in Headache: The Journal of Head and Face Pain (Apr. 16, 2019) available at: http://ir.zosanopharma.com/news-releases/news-release-details/zosano-announces-publication-analysis-acute-treatments-migraine.
Hindiyeh et al.; "Review of Acute Treatment of Migraine Trial Results With the New FDA Endpoints: Design Implications for Future Trials;" Headache; 2019; 59(5); pp. 819-824.
Zosano Pharma—Press Release: Zosano Pharma Completes Site Qualification Batches at Contract Manufacturing Organization as it Prepares for NDA Submission of Qtrypta (Jun. 18, 2019) available at: http://ir.zosanopharma.com/news-releases/news-release-details/zosano-pharma-completes-site-qualification-batches-contract.
Zosano Pharma—Press Release: Zosano Pharma Announces Upcoming Presentation at American Headache Society Annual Meeting (Jul. 1, 2019) available at: http://ir.zosanopharma.com/news-releases/news-release-details/zosano-pharma-announces-upcoming-presentation-american-headache.
Zosano Pharma—Press Release: Zosano Pharma Announces Keynote Speech at the Pharmaceutics & Advanced Drug Delivery Systems Conference (Jul. 3, 2019) available at: http://ir.zosanopharma.com/news-releases/news-release-details/zosano-pharma-announces-keynote-speech-pharmaceutics-advanced.
Zosano Pharma—Press Release: Zosano Pharma Presents Migraine-ACT Scores for Qtrypta at the American Headache Society (AHS) Annual Scientific meeting (Jul. 15, 2019) available at: http://ir.zosanopharma.com/news-releases/news-release-details/zosano-pharma-presents-migraine-act-scores-qtryptatm-american.
Zosano Pharma—Press Release: Zosano Pharma Files IND to Initiate a Phase 2/3 Clinical Study in Cluster Headache (Aug. 14, 2019) available at: http://ir.zosanopharma.com/news-releases/news-release-details/zosano-pharma-files-ind-initiate-phase-23-clinical-study-cluster.
Zosano Pharma—Press Release: Zosano Pharma Announces Upcoming Oral and Poster Presentations at the Congress of the International Headache Society (Aug. 23, 2019) available at: http://ir.zosanopharma.com/news-releases/news-release-details/zosano-pharma-announces-upcoming-oral-and-poster-presentations.
Zosano Pharma—Press Release: Zosano Pharma Announces the Presentation of Multiple Positive Datasets from the Qtrypta Long-Term Safety Study at the Congress of the International Headache Society (Sep. 9, 2019) available at: http://ir.zosanopharma.com/

(56) References Cited

OTHER PUBLICATIONS news-releases/news-release-details/zosano-pharma-announces-presentation-multiple-positive-datasets.

Henry et al.; "Microfabricated Microneedles: A Novel Approach to Transdermal Drug Delivery," Journal of Pharmaceutical Sciences, vol. 87, No. 8, Aug. 1998, pp. 922-925.

Robert G. Strickley, "Solubilizing Excipients in Oral and Injectable Formulations," Pharmaceutical Research, Feb. 2004, vol. 21, Issue 2, pp. 201-230.

International Search Report and Written Opinion of PCT/US2017/048258 dated May 7, 2018 (13 pages).

Kellerman et al.; "Rapid systemic delivery of zolmitriptan using an adhesive dermally applied microarray;" Pain Manag. (2017) 7(6), 559-567.

American Healthcare Drug Products & Safety News: Security Safety Communication Update (Jun. 13, 2016, available at https://www.americanhealthcare.com/Portals/0/Drug_Safety/Zecuity%20Safety%20Communication%20Update%20EM%206.16.16.pdf.

The Academy of Medical Sciences; Notes on Dr. Goadsby; available at: https://acmedsci.ac.uk/fellows/fellowsdirectory/ ordinary-fellows/fellow/Professor-Peter-Goadsby-0009328.

Widera et al, "Effect of delivery parameters on immunization to ovalbumin following intracutaneous administration by a coated microneedle array patch system," Vaccine (2006), vol. 24, pp. 1653-1664.

U.S. Pharmacopeia Chapter 725: Topical and Transdermal Drug Products—Product Performance Test, Pharmacopeial Forum (May-Jun. 2009), vol. 35, Issue 3, 12 pages.

Ghosh et al, "In vitro/in vivo correlations in transdermal product development," Therapeutic Delivery (2015), vol. 6 (9), pp. 1117-1124.

Seaber et al, "In Tolerability and pharmacokinetics of the novel antimigraine compound 311C90 in healthy male volunteers," Br. J. Clin. Pharmacol. (1996), vol. 41, pp. 141-147.

Zecuity (Sumatriptan) Migraine Patch: Drug Safety Communication—FDA Evaluating Risk of Burns and Scars, Food and Drug Administration Safety Alerts (Jun. 13, 2016), available at: http://www.fda.gov/safety/medwatch/safetyinformation/safetyalertsforhumanmedicalproducts/ucm504736.htm.

Imitrex Injection Packaging Insert, GlaxoSmithKline (Nov. 2015), available at: https://www.gsksource.com/pharma/content/dam/GlaxoSmithKline/US/en/Prescribing_Information/Imitrex_Injection/pdf/IMITREX-INJECTION-PI-PPI.pdf.

Dahlof, Non-oral formulations of triptans and their use in acute migraine, Cr. Pain Headache Rep. (2005), vol. 9, Issue 3, p. 206-212.

Houghton et al, Effect of sumatriptan, a new selective 5HT1-like agonist, on liquid gastric emptying in man, Aliment. Pharmacol. Ther. (1992), vol. 6, Issue 6, p. 685-691.

Cipolla et al, Gastric motor effects of triptans: open questions and future perspectives. Pharmacol. Res. (2001), vol. 43, Issue 3, p. 205-210.

Tack, The physiology and the pathophysiology of the gastric accommodation reflex in man, Verhandelingen (2000), vol. 62, Issue 3, p. 183-210.

Scott, Sumatriptan clinical pharmacokinetics, Clin. Pharmacokinet. (1994), vol. 27, Issue 5, p. 337-344.

Munjal et al, A randomized trial comparing the pharmacokinetics, safety, and tolerability of DFN-02, an intranasal sumatriptan spray containing a permeation enhancer, with intranasal and subcutaneous sumatriptan in healthy adults, Headache (2016), vol. 56, Issue 9, p. 1455-1465.

Yates et al, Pharmacokinetics, dose proportionality, and tolerability of single and repeat doses of a nasal spray Formulation of zolmitriptan in healthy volunteers, J. Clin. Pharmacol. (2002), vol. 42, Issue 11, p. 1244-1250.

Lionetto et al, Pharmacokinetic evaluation of zolmitriptan for the treatment of migraines, Expert Opin. Drug Metab. Toxicol. (2012), vol. 8, Issue 8, p. 1043-1050.

Lionetto et al, Sumatriptan succinate: pharmacokinetics of different formulations in clincal practice, Expert Opin. Pharmacother. (2012), vol. 13, Issue 16, p. 2369-2380.

Lutfullin et al, Adverse events in volunteers participating in Phase I clinical trials: a single-center five-year survey in 1,559 subjects. Int. J. Clin. Pharmacol. Ther., (2005), vol. 43, Issue 5, p. 217-226.

Sibille et al, Adverse events in phase I studies: a report in 1015 healthy volunteers, Eur. J. Clin. Pharmacol. (1998), vol. 54, Issue 1, p. 13-20.

Rosenzweig, The placebo effect in healthy volunteers: influence of experimental conditions on the adverse events profile during phase I studies, Clin. Pharmacol. Ther. (1993), vol. 54, Issue 5, p. 578-583.

Zosano Pharma, Press Release, Zosano Pharma Completes Enrollment in Phase 1 Study for Microneedle Patch Delivery of Zolmitriptan for the Treatment of Migraine (Sep. 1, 2015), available at: http://ir.zosanopharma.com/news-releases/news-release-details/zosano-pharma-completes-enrollment-phase-1-study-microneedle?ReleaseID=929757.

Zosano Pharma, Press Release, Zosano Pharma Announces Positive Phase 1 Results for Its ZP-Triptan Patch Program for Treatment of Migraine (Nov. 2, 2015), available at: http://ir.zosanopharma.com/news-releases/news-release-details/zosano-pharma-announces-positive-phase-1-results-its-zp-triptan?ReleaseID=939871.

Zosano Pharma, Press Release, Zosano Pharma Enrolls First Subject in Pivotal Clinical Trial for ZP-Triptan Patch Program for Treatment of Migraine (Jun. 17, 2016), available at: http://ir.zosanopharma.com/news-releases/news-release-details/zosano-pharma-enrolls-first-subject-pivotal-clinical-trial-zp?ReleaseID=976145.

Zosano Pharma, Press Release, First Subject Treated in Zosano Pharma's Pivotal Efficacy Trial for M207 Patch or Acute Migraine (Jul. 25, 2016), available at http://ir.zosanopharma.com/news-releases/news-release-details/first-subject-treated-zosano-pharmas-pivotal-efficacy-trial-m207?ReleaseID=980904.

Zosano Pharma, Press Release, Zosano Pharma Announces Completion of Enrollment in Pivotal Efficacy Trial for M207 for Acute Migraine (Nov. 8, 2016), available at: http://ir.zosanopharma.com/news-releases/news-release-details/zosano-pharma-announces-completion-enrollment-pivotal-efficacy?ReleaseID=998276.

Z0sano Pharma, Press Release, Zosano Pharma Announces Last Subject Treated in its Migraine Pivotal Trial (Jan. 5, 2017), available at: http://ir.zosanopharma.com/news-releases/news-release-details/zosano-pharma-announces-last-subject-treated-its-migraine.

Zosano Pharma, Press Release, Zosano Pharma Announces 3.8 mg Dose of M207, its Novel Transdermal Therapeutic, Meets Both Co-primary Endpoints in the ZOTRIP Pivotal Efficacy Trial in Migraine ( Feb. 13, 2017), available at: http://ir.zosanopharma.com/news-releases/news-release-details/zosano-pharma-announces-38mg-dose-m207-its-novel-transdermal?ReleaseID=1011563.

Zosano Pharma, Press Release, Zosano Presents Additional Data from ZOTRIP Study at American Headache Society, Demonstrating Positive Results for Pain Freedom and Sustained Pain Freedom (Jun. 12, 2017), available at: http://ir.zosanopharma.com/news-releases/news-release-details/zosano-presents-additional-data-zotrip-study-american-headache?ReleaseID=1029861.

Zosano Pharma, Press Release, Zosano Pharma Announces Outcome of End of Phase 2 Meetings with FDA (Jun. 26, 2017), available at: http://ir.zosanopharma.com/news-releases/news-release-details/zosano-pharma-announces-outcome-end-phase-2-meetings-fda?ReleaseID=1031284.

International Headache Society, Guidelines for Controlled Trials of Drugs in Migraine: Third Edition. A Guide of Investigators, Cephalalgia (2012), p. 6-38, vol. 32, Issue 1.

Cai et al, A New Drug Release Method in Early Development of Transdermal Drug Delivery Systems, Pain Research and Treatment (2012), https://www.hindawi.com/journals/prt/2012/953140.

Kakuji Tojo, Mathematical Modeling of Transdermal Drug Delivery, Journal of Chemical Engineering of Japan (1987), vol. 20, No. 3.

Flaten et al, In vitro skin models as a tool in optimization of drug formulation, European Journal of Pharmaceutical Sciences (2015).

(56) References Cited

OTHER PUBLICATIONS

Miillson et al, Migraine pharmacotherapy with oral triptans: a rational approach to clinical management, Expert Opinion on Pharmacotherapy (2000), vol. 1, Issue 3.
Food and Drug Administration, What is a Serious Adverse Event?, last updated Feb. 1, 2016, available at https://www.fda.gov/safety/medwatch/howtoreport/ucm053087.htm.
American Headache Society, Late-Breaking Findings on Migraine and New Investigational Treatments Presented at 2017 American Headache Society Annual Scientific Meeting, AHS Meeting Release Late Breakers (Jun. 7, 2017), available at /https://americanheadachesociety.org/ahs-meeting-release-latebreakers/.
Nikki Albert, What is on the horizon with migraines—with Dr. Goadsby, Brainless Blogger (Jun. 23, 2017), available at https://brainlessblogger.net/2017/06/23/what-is-on-the-horizon-with-migraines-with-dr-goadsby/.
Kearney et al, Microneedle-mediated delivery of donepezil: Potential for improved treatment options in Alzheimer's Disease, European Journal of Pharmaceutics and Biopharmaceutics (Jun. 2016), vol. 103, p. 43-50.
Nalluri et al, Effect of microneedles on transdermal permeation enhancement of amlodipine, Drug Delivery and Translational Research (Feb. 2017), vol. 7, p. 383-394.
Uppuluri et al, Microneedle-assisted transdermal delivery of Zolmitriptan: effect of microneedle geometry, in vitro Dermeation experiments, scaling analyses and numerical simulations, Drug Development and Industrial Pharmacy (Apr. 2017), vol. 43, Issue 8.
Nalluri et al, In Vitro Skin Permeation Enhancement of Sumatriptan by Microneedle Application, CWT. Drug Deliv. (2015), pp. 761-769, vol. 12, Issue 6.
International Search Report for International Application No. PCT/US2017/018738 dated Jun. 13, 2017 along with the Written Opinion.
Kellerman et al, Rapid systemic delivery of zolmitriptan using an adhesive dermally applied microarray, Pain Management, (Jul. 25, 2017), available at https://www.futuremedicine.com/doi/full/10.2217/pmt-2017-0036.
Dubey et al, Duel-Acting Subcutaneous Microemulsion Formulation for Improved Migraine Treatment with Zolmitriptan and Diclofenac: Formulation and In Vitro-In Vivo Characterization, AAPS Journal (Mar. 2014), vol. 16, No. 2.
Kayser et al, The antimigraine 5-HT1B/1D receptor agonists, sumatriptan and dihydroergotamine, attenuate pain-related behavior in a rate model of trigeminal neuropathic pain, British Journal of Pharmacology (2002) vol. 137, Issue 3, p. 1287-1297.
Rapoport et al, Optimizing the dose of zolmitriptan (Zomig, *311C90) for the acute treatment of migraine, American Academy of Neurology (1997), vol. 49, Issue 5, p. 1210-1218.
Lipton et al, Clinical applications of zolmitriptan (Zomig, 311C90), Cephalagia (1997), vol. 17, Issue 18, pp. 53-59.
Solomon et al, Clinical efficacy and tolerability of 2.5 mg zolmitriptan for the acute treatment of migraine, American Academy of Neurology (1997), vol. 49, Issue 5, p. 1219-1225.
Adelman and Lewit, Comparative Aspects of Triptans in Treating Migraine, Clinical Cornerstone (2001), vol. 4, Issue 3, p. 53-64.
Lipton et al, Examination of unmet treatment needs among persons with episodic migraine: results of the American Migraine Prevalence and Prevention Study. Headache (2013), vol. 13, Issue 8, p. 1300-1311.
Gilmore and Michael, Treatment of acute migraine headache, Am. Fam. Phys. (2011), vol. 83, Issue 3, p. 271-280.
Marmura et al, The acute treatment of migraine in adults: the American Headache Society evidence assessment of migraine pharmacotherapies, Headache (2015), vol. 55, Issue 1, p. 3-20.
Rapoport, et al. "Rapid Systemic Absorption of Zolmitriptan from M207 is Associated with a High Rate of Pain Relief and a Low Incidence of Moderate or Severe Pain Recurrence;" 60th Annual Scientific Meeting of the American Headache Society, Jun. 28-Jul. 1, 2018; San Francisco, CA; Poster # PF50 (Published Summary and Poster).
Ferrari, et al.; "Treatment of Migraine Attacks with Sumatriptan. The Subcutaneous Sumatriptan International Study Group;" The New England Journal of Medicine. 1991; 325(5):316-21.
Vauquelin G., "Effects of target binding kinetics on in vivo drug efficacy: koff, kon and rebinding," British journal of pharmacology; 2016; 173(15):2319-34.
Vauquelin G; "Cell membranes . . . and how long drugs may exert beneficial pharmacological activity in vivo;" British journal of clinical pharmacology; 2016; 82(3):673-82.
"Migraine: Developing Drugs for Acute Treatment Guidance for Industry;" Feb. 2018; (12 pages); downloaded from: https://www.fda.gov/downloads/drugs/guidances/ucm419465.pdf.
Geraud, et al.; "Comparison of the efficacy of zolmitriptan and sumatriptan: issues in migraine trial design;" Cephalalgia: an international journal of headache; 2000; 20 (1):30-8.
Martin et al.; "Analysis of Ligand-Receptor Kinetics of Zolmitriptan, its Primary Metabolite, and Sumatriptan;" Poster Presentation; 60th Annual Scientific Meeting of the American Headache Society; Jun. 28-Jul. 1, 2018; San Francisco, CA.
File History of U.S. Appl. No. 15/882,504 (access is obtained through the USPTO records).
File History of U.S. Appl. No. 16/109,937 (access is obtained through the USPTO records).
File History of U.S. Appl. No. 17/330,289 (access is obtained through the USPTO records).
Zosano Phatma, Press Release "Zosano Pharma Initiates Phase 2/3 Clinical Study in Cluster Headache" dated Oct. 24, 2019.
Zosano Pharma, Press Release "Zosano Pharma Announces Completion of Pre-NDA Meetings with FDA for Qtrypta™" dated Nov. 13, 2019.
Zosano Pharma, Press Release "Zosano Pharma Reports Third Quarter 2019 Financial Results and Provides Corporate Update" dated Nov. 14, 2019.
Zosano Pharma, Press Release "Zosano Announces Pricing of Registered Direct Offering" dated Nov. 27, 2019.
Zosano Pharma, Press Release "Zosano Announces FDA Submission of New Drug Application for Qtrypta" dated Dec. 23, 2019.
Zosano Pharma, Press Release "Zosano Pharma Announces FDA Acceptance of 505(b)(2) New Drug Application for Qtrypta™ for the Acute Treatment of Migraine" dated Mar. 4, 2020.
Zosano Pharma, Press Release "Zosano Pharma Reports Fourth Quarter and Fiscal Year 2019 Financial Results" dated Mar. 13, 2020.
Zosano Pharma, Press Release "Zosano Pharma Reports First Quarter 2020 Financial Results and Provides Corporate Update" dated May 14, 2020.
Zosano Pharma, Press Release "Zosano Pharma to showcase new post-hoc analyses of Qtrypta's (M207) clinical trial data comparing key efficacy results from the pivotal study and the open-label long term safety study on the 2020 American Headache Society's Virtual Annual Scientific Meeting Platform" dated Jun. 13, 2020.
Zosano Pharma, Press Release "Zosano Pharma Reports Second Quarter 2020 Financial Results and Provides Corporate Update" dated Aug. 6, 2020.
Zosano Pharma, Press Release "Zosano Pharma Announces Partnership Agreement with EVERSANA to Support the Launch and Commercialization of Qtrypta™" dated Aug. 6, 2020.
Zosano Pharma, Press Release "Zosano Pharma Announces Agreement to Collaborate with Mitsubishi Tanabe Pharma Corporation" dated Aug. 18, 2020.
Zosano Pharma, Press Release "Zosano Pharma Receives Preliminary FDA Communication on Qtrypta™ NDA" dated Sep. 30, 2020.
Zosano Pharma, Press Release "Zosano Pharma Receives Complete Response Letter from FDA for Qtrypta™" dated Oct. 21, 2020.
Zosano Pharma, Press Release "Zosano Pharma Reports Third Quarter 2020 Financial Results" dated Nov. 13, 2020.
Zosano Pharma, Press Release "Zosano Pharma Requests Type A Meeting with the FDA to Review Resubmission Plans for Qtrypta™ New Drug Application" dated Jan. 4, 2021.
Zosano Pharma, Press Release "Zosano Pharma Announces NDA Resubmission Plans Following Type A Meeting with FDA" dated Feb. 1, 2021.

(56) References Cited

OTHER PUBLICATIONS

Zosano Pharma, Press Release "Zosano Pharma Presents Early-Onset of Action Data for Qtrypta™ in Acute Treatment of Migraines" dated Feb. 1, 2021.

Zosano Pharma, Press Release "Zosano Pharma Confirms NDA Resubmission Strategy Following Type A Meeting Minutes from FDA" dated Feb. 22, 2021.

Zosano Pharma, Press Release "Zosano Pharma Reports Fourth Quarter and Fiscal Year 2020 Financial Results" dated Mar. 11, 2021.

Zosano Pharma, Press Release "Zosano Pharma Confirms Plan to Move Forward with Pharmacokinetic Study Following Protocol Review by FDA" dated Apr. 26, 2021.

Zosano Pharma, Press Release "Zosano Pharma Reports First Quarter 2021 Financial Results" dated May 12, 2021.

Zosano Pharma, Press Release "Zosano Appoints Industry Veteran, Kathy McGee, to its Board of Directors" dated May 25, 2021.

Zosano Pharma, Press Release "Zosano Pharma Announces Publication of Clinical Data Regarding the Long-term use of Qtrypta™ for the Treatment of Acute Migraine in The Journal of Headache and Pain" dated May 26, 2021.

Zosano Pharma, Press Release "Zosano Pharma Announces Issuance of U.S. Patent for Method of Rapidly Achieving Therapeutic Levels with M207 for the Acute Treatment of Migraine" dated Jul. 20, 2021.

Zosano Pharma, Press Release "Zosano Pharma Reports Second Quarter 2021 Financial Results" dated Aug. 10, 2021.

Zosano Pharma, Press Release "Zosano Pharma Granted Type C Meeting with FDA Regarding NDA Resubmission for M207 Following Preliminary Top-Line Pharmacokinetic Study Results" dated Oct. 4, 2021.

Zosano Pharma, Press Release "Zosano Pharma Reports Third Quarter 2021 Financial Results" dated Nov. 10, 2021.

Spierings et al., "Randomized, Double-blind, Multi-center, Parallel-group, Evaluation of the Safety and Efficacy of ADAM Zolmitriptan for the Acute Treatment of Migraine" Jun. 16, 2017.

Zosano Pharma Corporate Presentation—Jan. 31, 2022.

File History of U.S. Appl. No. 17/392,536 (access is obtained through the USPTO records).

File History of U.S. Appl. No. 63/234,661 (access is obtained through the USPTO records).

Mayo Clinic; "Cluster Headache"; retrieved on Jun. 30, 2020 from: https://www.mayoclinic.org/diseases-conditions/cluster-headache/symptoms-causes/syc-20352080.

"Navigating the Symptoms & Treatments for Cluster Headaches" published Apr. 18, 2019 on the American Migraine Foundation's website; retrieved on Jun. 30, 2020 from: https://americanmigrainefoundation.org/resource-library/cluster-headache-2/.

\* cited by examiner

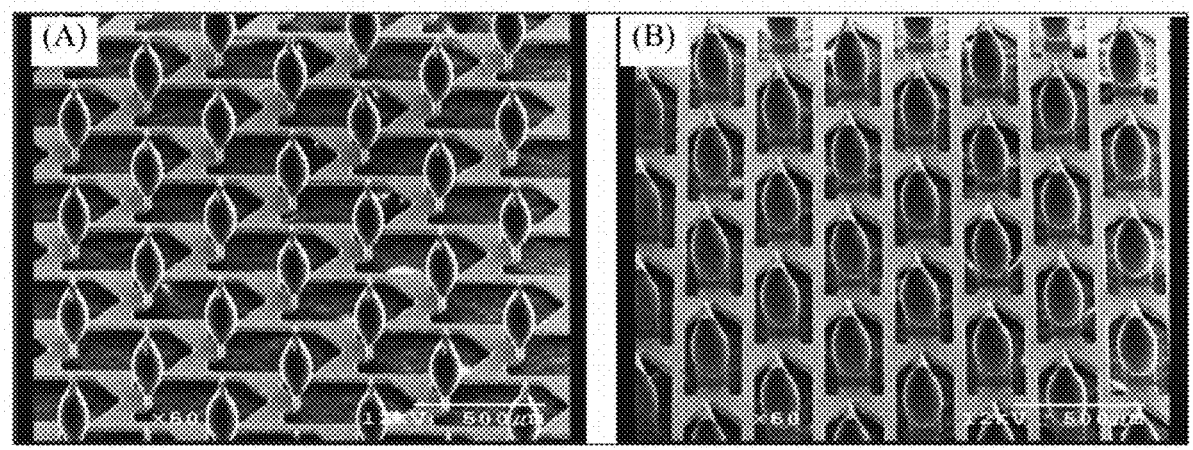
Figure 1(A)-(B)
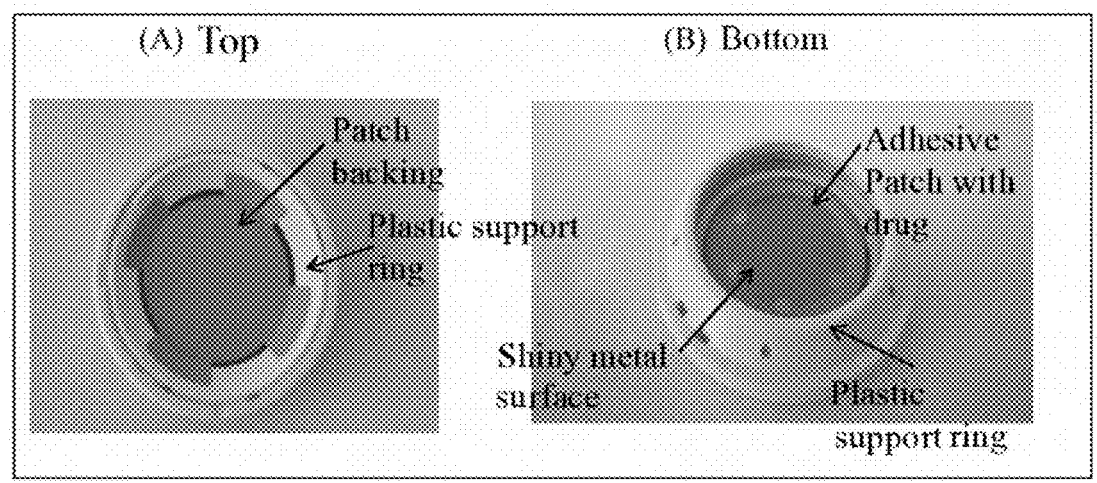
Figure 2(A)-(B)

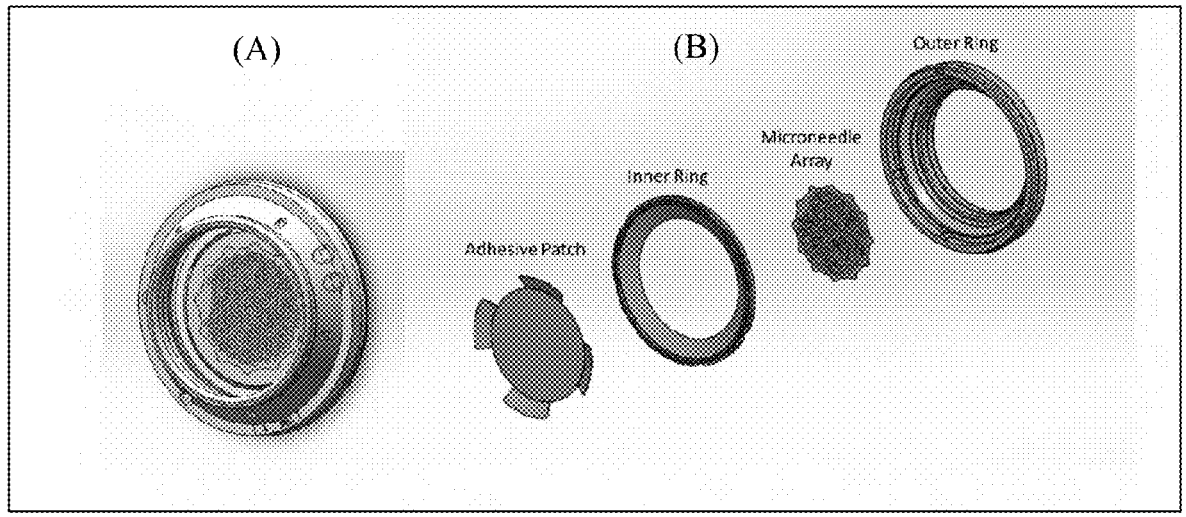
Figure 3(A)-(B)
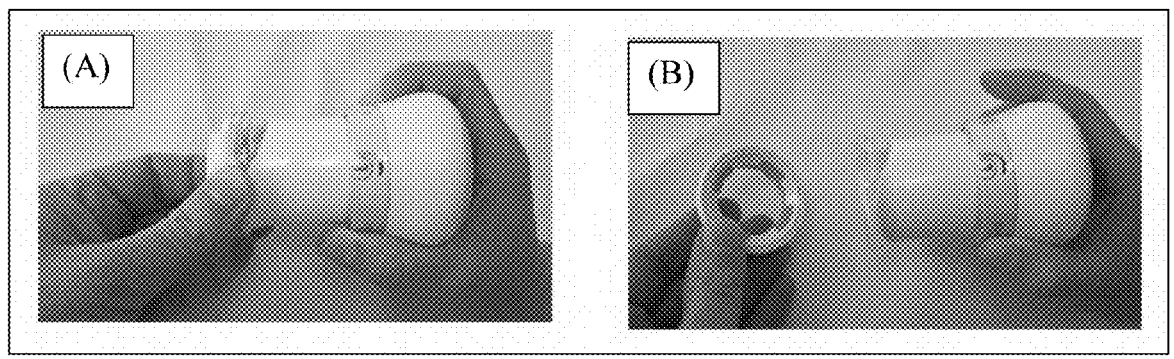
Figure 4(A)-(B)

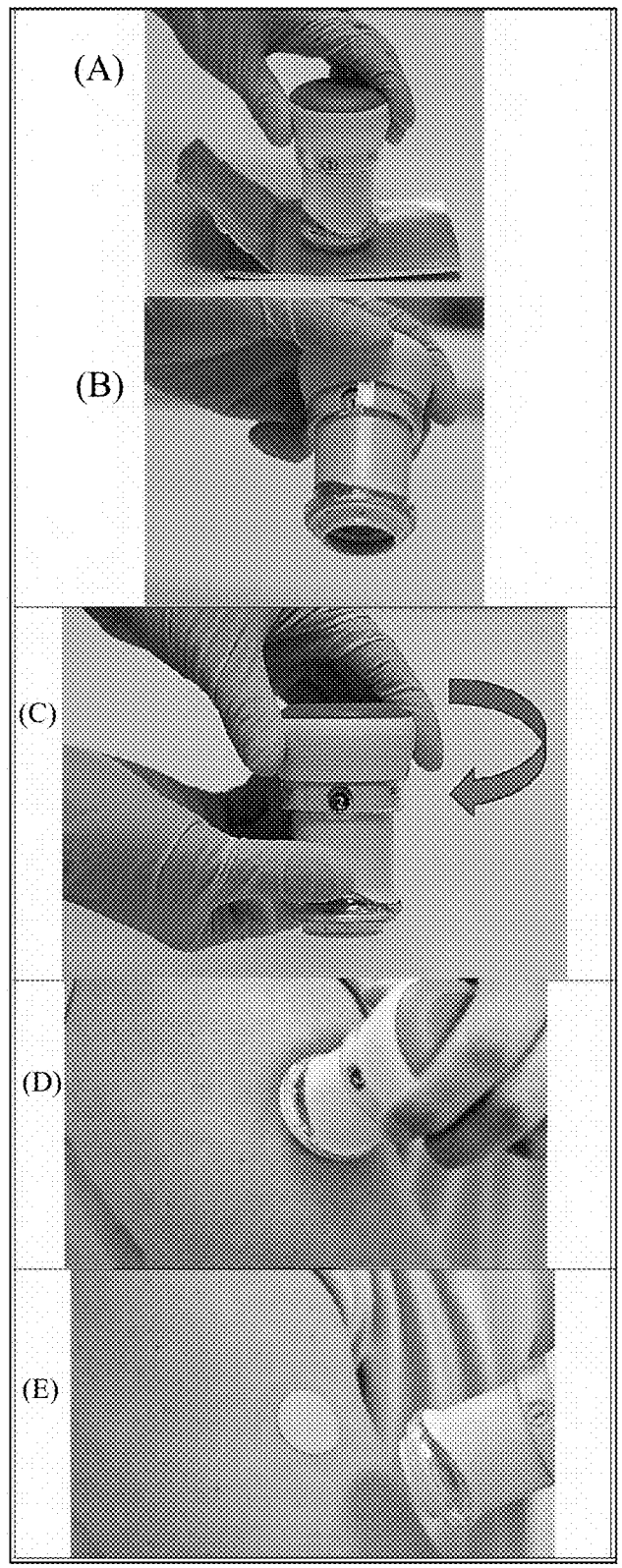
Figure 5(A)-(E)

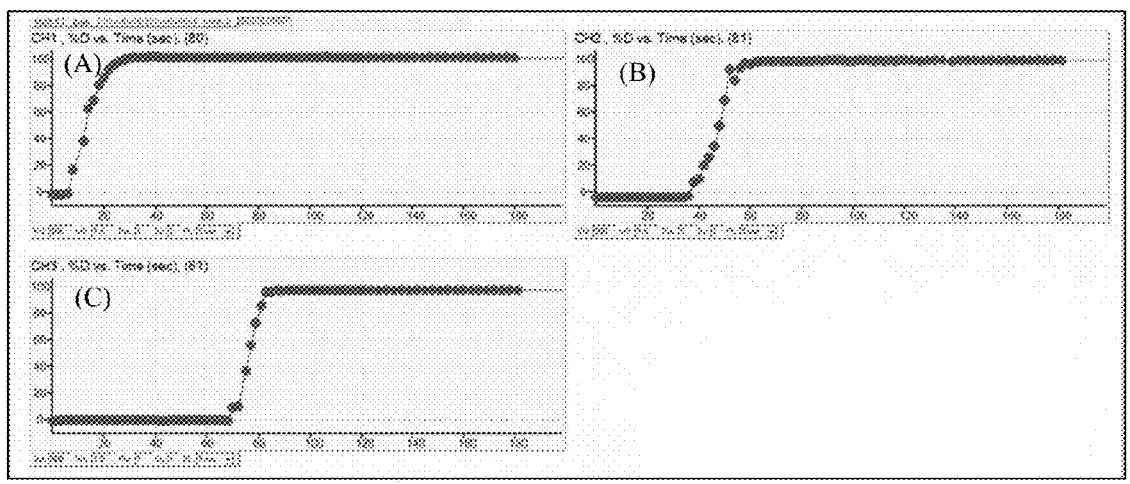
Figure 6(A)-(C)
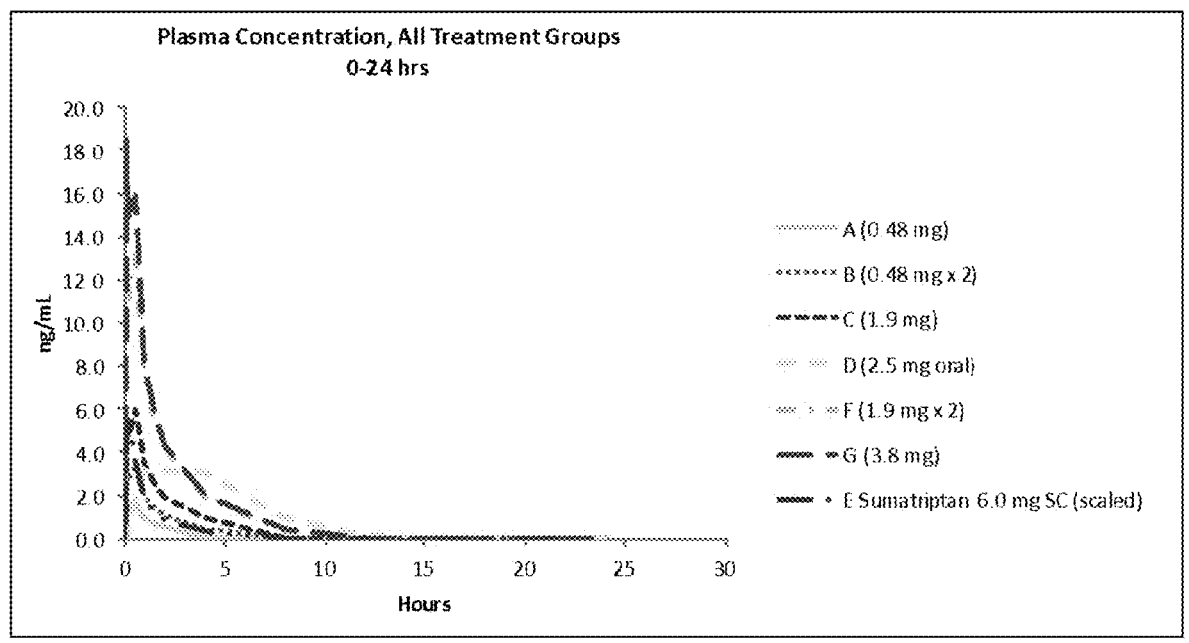
Figure 7

[a]via Cochran-Mantel-Haenszel test controlling for randomization stratification MBS. Last observation carried forward was used to impute missing data. This secondary endpoint not formally considered to be significant due to the fixed sequential testing methodology used in this study to control for overall type I error

[a]Defined as those who had pain relief at 2 hours and a recurrence of moderate or severe pain at the given time point. [b]via Cochran-Mantel-Haenszel test controlling for randomization stratification MBS. Last observation carried forward was used to impute missing data

METHOD OF RAPIDLY ACHIEVING THERAPEUTIC CONCENTRATIONS OF TRIPTANS FOR TREATMENT OF MIGRAINES AND CLUSTER HEADACHES

CROSS REFERENCE TO RELATED APPLICATIONS

This application claims benefit of U.S. Provisional Patent Application No. 62/691,502 filed on Jun. 28, 2018; which is incorporated herein by reference in its entirety to the full extent permitted by law.

TECHNICAL FIELD

The present invention relates to the field of transdermal or intracutaneous delivery of pharmaceutical agents, and more particularly to the delivery of triptans, including zolmitriptan.

BACKGROUND

According to the Migraine Research Foundation, migraine affects 30 million men, women and children in the United States. Most migraines last between four and 24 hours, but some last as long as three days. According to published studies, 63% of migraine patients experience between one and four migraines per month. The prevalence in women (about 18%) is on par with asthma and diabetes combined. Approximately one-third of those afflicted with migraines have three or more migraines per month and over half report severe impairment or the need for bed rest. Migraines are most prevalent in the third decade of life, affecting both productivity and quality of life. In surveys of desirable attributes for therapies for migraine, fast relief consistently scores very high as one of the most important factors for a migraine therapy.

Acute migraine is an incapacitating headache disorder that is characterized by episodic attacks of moderate to severe headache together with various combinations of neurological, gastrointestinal and autonomic symptoms. Migraine without aura is usually associated with nausea, vomiting, sensitivity to light, sound or movement, and can last for 4-72 hours if untreated. Previously termed "common migraine," migraine without aura is experienced by approximately 65% of patients. Migraine with aura is experienced by about 15-20% of patients; individuals suffer from transient focal neurological symptoms, usually visual. The visual symptoms are known as an aura. The remainder of migraine patients experience both types of migraine.

About a quarter of migraine patients experience one or more episodes per week. The most unpleasant symptoms associated with acute migraine are nausea and vomiting. The majority (about 90%) of patients experience nausea; about 70% experience vomiting; and a third typically experience both symptoms with every attack.

Cluster headaches are excruciating headaches that recur in a cyclical pattern (a "cluster"), usually daily, for a period of 1 week or more, usually for six to twelve weeks. In chronic cluster headache, clusters last for a year or more without remission. Cluster headaches are considered to be among the worst headaches known to medical science, and are known to result in pain more severe than migraines. In approximately 47% of cases, cluster headache attacks recur at the same time of day or night, and, in particular, during sleep. Clusters can start at the same time and have a similar duration year after year. These recurrence patterns suggest a role of the hypothamlamus (the body's biological clock), although the exact cause is unknown.

The pain of a cluster headache is typically on one side (unilateral) or localized and is around or above the eye. During an attack, patients may become agitated and restless, and they may have trouble resting in one place. As patients may prefer to move around, they may rock, sit, pace, crawl, scream in pain, or even bang their head against a hard surface. In some patients, due to the severity and recurrence of cluster headaches, there is a heightened risk of alcohol and drug abuse, self-injury, and even suicide. Notably, cluster headaches are sometimes referred to as "suicide headaches."

Treatment options for cluster headaches are extremely limited. and there is a strong need for treatments which provide rapid and effective responses. See, e.g., Law et al, *Triptans for acute cluster headache*, Cochrane Database of Systematic Reviews (2013), Issue 7. While migraines are different from cluster headaches, it is believed that certain treatments for migraines including triptans could also be effective for cluster headaches. However, oral and nasal routes of administration are not particularly effective due to slow absorption rates and the short duration of the headache. Injected triptans have shown some efficacy, but they are limited by needle phobia, lack of portability, complex preparation, the requirement for sharps disposal, and safety issues related to needle prick, cutting, and cross contamination infection.

The acute treatment of migraine was revolutionized in 1991 by the introduction of the triptan class, such as sumatriptan and zolmitriptan. The triptans are serotonin derivatives displaying highly selective and potent agonist activity at the vascular $5\text{-HT}_{1B}$ receptor and the neuronal $5\text{-HT}_{1D}$ receptor. The mode of action of the triptans is hypothesized to be three-fold: (1) binding of postsynaptic vascular $5\text{-HT}_{1B}$ receptors, to stimulate vasoconstriction of meningeal vessels; (2) binding of presynaptic neuronal $5\text{-HT}_{1D}$ receptors, to inhibit release of pro-inflammatory neuropeptides; and (3) binding of presynaptic neuronal $5\text{-HT}_{1D}$ receptors, to diminish the firing rate in trigeminal neurons and the trigeminal nucleus caudalis (central action). Triptans have similarly shown improved efficacy in treating cluster headaches over placebos.

Each of the currently available methods of administering triptans, including oral, nasal spray, subcutaneous injection and iontophoretic intracutaneous patch (which is a device that delivers medicine through the skin by a low electrical current), has significant disadvantages. Some migraine patients fail to respond consistently to oral triptans, and oral treatments may be ineffectual and/or unpleasant for patients who are suffering from the nausea, vomiting, or gastric stasis that can be associated with migraine. Oral, nasal and iontophoretic patch triptan products are also characterized by delayed absorption and relatively slow onset of action causing insufficient relief, especially early in the episode. This delay is a critical failure in cluster headache, as the fact that cluster headache episodes often last for 30 minutes or less implies a complete lack of treatment for oral triptans, and significantly reduced efficacy for nasal when compared to subcutaneously delivered triptans. Cluster headaches are often accompanied by stuffy or runny nose, which may impact absorption following nasal delivery. Nasal sprays may be unpleasant in taste, and use of injectables can cause discomfort.

Sumatriptan (IMITREX®) has been commercially available in a number of dosage forms, such as a tablet, subcutaneous (SC) injection, nasal spray and by transdermal electrophoresis. Oral administration (as a succinate) suffers from poor bioavailability (about 15%) due to poor absorption and pre-systemic metabolism. The time to reach maximum concentration in the bloodstream ($T_{max}$) after oral tablet administration is about 2 hours. A rapid-release tablet formulation has roughly the same bioavailability, although the $T_{max}$ is achieved on average 10-15 minutes earlier than the conventional tablet. When injected, sumatriptan is faster-acting (usually within 10 minutes), but the duration of action is lower. Although SC is faster, the tablet formulations of sumatriptan have been much more widely prescribed than the injection because many patients do not like injecting themselves.

The triptans have an excellent safety profile when used appropriately and their adverse effect profile is similar to that observed with placebo in clinical trials. Like other compounds in the triptan class, zolmitriptan has been shown to be effective and well-tolerated in placebo-controlled clinical trials. It is available in a number of commercial formulations (ZOMIG®): (a) a conventional release tablet (2.5 mg and 5.0 mg); (b) a "fast melt" orally disintegrating tablet (2.5 mg and 5.0 mg); and (c) a nasal spray (5.0 mg).

The bioavailability of zolmitriptan conventional release tablets has been found to be between 41 and 48%, and administration with food reduced $C_{max}$ and AUC by 13-16% (Seaber et al., "The absolute bioavailability and metabolic disposition of the novel antimigraine compound zolmitriptan (311C90)," Br. J. Clin. Pharmacol. 1997; 43(6): 579-87; Seaber et al., "The absolute bioavailability and effect of food on the pharmacokinetics of zolmitriptan in healthy volunteers," Br. J. Clin. Pharmacol. 1998; 46: 433-439). The $T_{max}$ of the conventional tablet is about 1.5 hours. Absorption is reported to be lower during an actual migraine attack so the $T_{max}$ may be higher during a migraine. Zolmitriptan is converted to an active N-desmethyl metabolite such that the metabolite concentrations are about two-thirds that of zolmitriptan. Because the $5HT_{1B/1D}$ potency of the metabolite is 2 to 6 times that of the parent, the metabolite may contribute a substantial portion of the overall effect after zolmitriptan administration.

The bioavailability of the orally disintegrating tablets is similar to that of the conventional tablets but the $T_{max}$ is (somewhat surprisingly) higher, at about 3 hours for the disintegrating tablets compared with 1.5 hours for the conventional tablet. The disintegrating tablets may also exacerbate nausea often concomitant with a migraine attack.

Zolmitriptan has significant advantages over other triptans when contemplated for alternate delivery routes and methods. Only three triptans, zolmitriptan, naratriptan, and frovatriptan have a lowest oral dose less than 5 mg. However, at this lowest dose, zolmitriptan significantly outperforms naratriptan in terms of pain relief at 2 hours (62% vs. 49%), and pain freedom at 2 hours (29% vs. 18%). (C. Asseburg, P. Peura, T. Oksanen, J. Turunen, T. Purmonen and J. Martikainen (2012); Cost-effectiveness of oral triptans for acute migraine: Mixed treatment comparison. International Journal of Technology Assessment in Health Care, 28, pp 382-389), and frovatriptan "has the lowest efficacy in 2-hour response, 2-hour pain free compared to the other triptans" (Neuropsychiatr Dis Treat. 2008 February; 4(1): 49-54).

Nasal administration of zolmitriptan was used in an attempt to overcome the disadvantages of oral delivery described above, and doses of 2.5 mg and 5.0 mg have been commercialized. However, the $T_{max}$ of zolmitriptan is only improved slightly (to about 1.5 hours), and a large portion of the dose is swallowed and still subject to first pass metabolism.

Other non-oral routes of administration such as transdermal iontophoresis, patches and liquid injectors have the disadvantages of skin irritation and scarring, pain and inability to deliver a therapeutically effective dose. Subcutaneously injected sumatriptan has been available for years but has never been widely used because it is difficult to prepare and due to issues related to needle phobia, sharps disposal, and accidental pricking, cutting, and cross contamination that are related to delivery with a needle.

Effectiveness of treatment of migraine with triptans has been shown to be more dependent on rate of absorption than on dose or plasma concentration. More rapid absorption and earlier $T_{max}$ leads to better pain relief, not just early in a migraine episode but surprisingly even later when the plasma concentration from the slower absorbed therapy is higher. In cluster headache, in addition to the above effect, there is a need for rapid absorption simply because of the short duration of the headache event. Rapid absorption can further reduce required application time of a transdermal patch, and lead to more efficient delivery of the packaged dose, which facilitates reproducibility, for example by reducing variability caused by variation in patch wear time.

Therefore, advantages could be achieved by a therapeutic alternative to currently available migraine and cluster headache treatments that: (a) has an onset of action faster than oral and comparable to SC formulations but without issues related to needles; (b) avoids the oral route that may limit absorption caused by the gastric effects of migraine (gastric stasis, nausea and vomiting); (c) mitigates the potential for food interactions, avoids first-pass metabolism and reduces the potential for drug interactions; (d) is preferred by patients (rapid onset but not injected or with unpleasant taste/smell e.g., nasal sprays); (e) has lower absorption that reduces triptan side effects, e.g., chest constriction while still effective at mitigating migraine related headache and nausea; (f) can be conveniently carried by the patient for use at the first sign of a migraine or cluster headache; and (g) can be quickly, conveniently, and safely self-administered. Additionally, because nausea is present in 60-70% of migraine attacks, it would be advantageous for physicians and patients to have a product that can be administered without using the gastrointestinal system and not susceptible to lack of absorption due to emesis. Similarly, stuffy and runny nose in cluster headache may impact the efficacy of nasally delivered drugs.

Thus, there is a need in the art for a route of administration that can accommodate the relatively large doses of triptans, such as zolmitriptan, typical of oral doses but lacks the side effects of orally delivered doses. The present disclosure meets these challenges and needs, among others. For instance, Applicant has surprisingly discovered that transdermal delivery of a triptan, such as zolmitriptan as described herein, can rapidly deliver the relatively large doses of zolmitriptan typical of oral doses with plasma concentrations in the range of or higher than those seen following oral administration, despite the difficulty of the skin's highly impermeable nature.

There is furthermore a need for a route of triptan administration that has improved efficacy due to an absorption rate comparable to injection and is portable and easy to prepare while avoiding the issues of needle phobia, sharps disposal, and accidental pricking, cutting, and cross contamination that are related to delivery with a needle.

Further, there is a need in the art for an effective method of triptan administration through transdermal delivery in which the patch can be accurately and evenly coated, without causing issues of residual drug on the array or issues of manufacturing inconsistencies, such as uneven formulation coating on a patch or difficulty with formulation sticking to the patch. Many attempts have been made to use transdermal microneedle patches for effective drug delivery; however, achieving rapid release of drug from and rapid treatment with microneedle systems, optimizing and developing effective microneedle shapes and sizes, while also containing a sufficient dosage of drug has proved elusive. Applicants, through significant development efforts, developed a system of effective triptan delivery by addressing issues of viscosity, drug loading, surface tension, shape and size of microneedles, and common manufacturing defects.

SUMMARY

The present disclosure relates to compositions, devices, methods of treatment, kits and methods of manufacture of pharmaceutical products useful in the treatment of migraines and other conditions, including cluster headaches. More specifically, the disclosure is directed to administration of a triptan, such as zolmitriptan, as the active pharmaceutical ingredient to a subject in need thereof. In particular, the present disclosure is directed to transdermally or intracutaneously, or otherwise through the skin, administering a therapeutically effective dose of the active ingredient that is more rapidly available in the subject's bloodstream as compared to a therapeutically effective oral dose of the active ingredient, in a format that is easy to use and portable for rapid administration. In one embodiment, the transdermal delivery of a triptan, such as zolmitriptan, generally comprises a patch assembly having a microprojection member that includes a plurality of microprojections (or "needles" or "microneedles" or "array") that are coated with, in fluid contact with a reservoir of, or otherwise comprise the drug. The patch assembly further comprises an adhesive component, and in a preferred embodiment the microprojection member and adhesive component are mounted in a retainer ring. The microprojections are applied to the skin to deliver the drug to the bloodstream or, more particularly, are adapted to penetrate or pierce the stratum corneum at a depth sufficient to provide a therapeutically effective amount to the bloodstream. In one embodiment, the insertion of the drug-coated microneedles into the skin is controlled by a handheld applicator that imparts sufficient impact energy density in less than about 10 milliseconds.

Preferably, the microprojection member includes a biocompatible coating formulation comprising the drug, such as zolmitriptan, in a dose sufficient to provide therapeutic effect. The coating may further comprise one or more excipients or carriers to facilitate the administration of the drug across the skin. For instance, the biocompatible coating formulation comprises zolmitriptan and a water-soluble carrier that is first applied to the microprojections in liquid form and then dried to form a solid biocompatible coating.

In a preferred embodiment, zolmitriptan, excipients, the coating and drying process lead to a drug coating that is non-crystalline (amorphous) with a surprisingly rapid dissolution rate. In this embodiment, the coating, upon its application to the skin via the microneedles, dissolves at a rate sufficient for rapid uptake of the drug into the epidermis and bloodstream. In one embodiment, such rate is less than 20 minutes, or less than 15 minutes, or less than 10 minutes, or less than 5 minutes, or less than 2.5 minutes, or less than 1 minute. This rate leads to rapid migraine and cluster headache relief. Preferably, this rapid uptake leads to greater than about 10% of patients being pain free in 1 hour after administration, more preferably greater than about 20% of patients, most preferably about 25% of patients or more are pain free. In another embodiment, this rapid uptake leads to pain free. Patients achieving pain relief in 1 hour after administration, or greater than 50 percent of patients, or about 65% of patients or more achieve pain relief 1 hour after administration. Preferably, the drug coating remains amorphous for 1 year, more preferably 2 years, following gamma or e-beam irradiation.

Such intracutaneous delivery system may be in the form of a device that is adapted for easy use directly by the patient. For example, the system may be a drug-device combination product comprising: (a) a disposable microprotrusion member with titanium microneedles that are coated with a drug product formulation and dried, the microprotrusion member being centered on an adhesive backing thus forming a patch, and (b) a reusable handheld applicator that ensures the patch is applied to the skin with a defined application energy sufficient to press the microneedles into the stratum corneum thereby resulting in drug absorption. In one embodiment, the delivery system comprises a patch comprising about 0.2 mg to about 10 mg zolmitriptan, or about 1 mg to about 4 mg, or about 1 mg, or about 1.9 mg, or about 2 mg, or about 3 mg, or about 3.8 mg, or about 4 mg, or about 5 mg, or about 6 mg, or about 7 mg, or about 8 mg, or about 9 mg zolmitriptan. In one embodiment, the delivery system is designed to deliver about 0.2 mg to about 10 mg zolmitriptan intracutaneously, or about 1 mg to about 4 mg, or about 1 mg, or about 1.9 mg, or about 2 mg, or about 3 mg, or about 3.8 mg, or about 4 mg, or about 5 mg, or about 6 mg, or about 7 mg, or about 8 mg, or about 9 mg, or more than about 1 mg, or more than about 1.9 mg, or more than about 2 mg, or more than about 3 mg, or more than about 3.8 mg, or more than about 4 mg, or more than about 5 mg, or more than about 6 mg, or more than about 7 mg, or more than about 8 mg or more than about 9 mg zolmitriptan.

In another embodiment, the present disclosure relates to a method for transdermally or intracutaneously administering a triptan to a patient in need thereof, comprising the steps of: (a) providing a transdermal patch adapted to intracutaneously deliver a triptan, comprising a microprojection member having a plurality of microprojections that are adapted to penetrate or pierce the stratum corneum of the patient, wherein the microprojections comprise a biocompatible coating partially or fully disposed on the microprojections, the coating comprising a therapeutically effective amount of the triptan; and (b) applying the microprojection member of the device to the skin of the patient, whereby the plurality of microprojections penetrate or pierce the stratum corneum and deliver the triptan to the patient's bloodstream. In one embodiment, the triptan is zolmitriptan and is coated on the microprojections in a total amount of approximately 0.2 to 10 mg of which approximately 50%, or 60%, or 65%, or 75%, or 80%, or 85%, or 90%, or 95%, or 100% of such dose reaches the bloodstream of the patient after administration, preferably wherein more than approximately 50%, or 60%, or 65%, or 75%, or 80%, or 85%, or 90%, or 95% of such dose reaches the bloodstream of the patient after administration.

The present disclosure encompasses a method for treatment or alleviation of migraine or cluster headache in a human patient in need thereof, comprising the transdermal or intracutaneous administration of a therapeutically effective amount of zolmitriptan that produces a therapeutic concentration of zolmitriptan in the bloodstream faster than therapeutically effective doses administered orally, intranasally, sublingually, or iontophoretically. In one aspect, the method for treatment or alleviation of migraine or cluster headache in a patient results in a plasma $T_{max}$ as quick as about 2 minutes and not later than about 30-40 minutes in most subjects. In another aspect, the method results in a maximum plasma concentration ($C_{max}$) of zolmitriptan of less than 50 ng/ml.

In one embodiment, the zolmitriptan-coated microneedle patch as disclosed herein achieves rapid blood plasma concentrations after application during a migraine or cluster headache attack. Such patch provides pain freedom and freedom from bothersome migraine or cluster headache symptoms for at least 45 minutes post administration. A patient's most bothersome migraine symptom in addition to pain is usually selected from sensitivity to light, particularly bright lights (photophobia), sensitivity to sound, particularly loud sounds (phonophobia), and nausea, although migraines can also be accompanied by vomiting, sensitivity to smell, aura, vision changes, numbness, tingling, weakness, vertigo, feeling lightheaded or dizzy, puffy eyelid, difficulty concentrating, fatigue, diarrhea, constipation, mood changes, food cravings, hives, and/or fever. Common symptoms of cluster headache include excruciating pain, often on one side of the head and generally situated in or around one eye, but which may radiate to other areas of face, head, neck and shoulders, restlessness, excessive tear production and redness in the eye on the affected side, stuffy or runny nose, forehead or facial sweating, pale skin (pallor), facial flushing, swelling around the eye on the affected side, and/or drooping eyelid.

Additional embodiments of the present devices, compositions, methods and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

BRIEF DESCRIPTION OF THE DRAWINGS

This application file contains at least one drawing executed in color. Copies of this patent application publication with color drawings will be provided by the Office upon request and payment of the necessary fee.

The foregoing features of embodiments will be more readily understood by reference to the following detailed description, taken with reference to the accompanying drawings, in which:

FIGS. 1(A) and (B) are scanning electron micrographs (SEM) of MF1663 array design coated with 1.9 mg zolmitriptan.

FIG. 2(A)-(B) show views of the patch and the retainer ring structure. (A) provides a top view of the patch and retainer ring. (B) provides a bottom perspective view of the patch attached to a retainer ring.

FIG. 3(A)-(B) illustrates the patch assembly, comprised of a patch in a retainer ring. (A) provides a side view of the patch assembly. (B) illustrates an exploded view of a patch assembly.

FIG. 4(A)-(B) illustrates how the used plastic retainer ring is removed from the applicator and discarded. The fingers are used to pull the used retainer ring off the applicator. (A) provides a side view of the retainer ring attached to the applicator. (B) provides a side view of the retainer ring separated from the applicator.

FIG. 5(A)-(E) are photographs of the steps for application of the patch of the present invention. (A) illustrates step 1: snap patch assembly onto applicator. (B) further illustrates step 1 and provides a bottom front perspective of the patch assembly with the applicator. (C) illustrates step 2: twist applicator cap clockwise from position 1 to position 2 to unlock for patch application. (D) illustrates step 3: press applicator downward to apply patch to skin. (E) illustrates step 4: patch is applied to the patient's skin and the retainer ring remains attached to the applicator.

FIG. 6(A)-(C) provides in vitro release profiles of ZP-Zolmitriptan M207 1.9 mg patches. (A), top left, provides in vitro release profiles of ZP-Zolmitriptan M207 1.9 mg patches that have been E-beam irradiated and stored at RT for 10 months, L/N0164004. (B), top right, provides in vitro release profiles of ZP-Zolmitriptan M207 1.9 mg patches that have been non-irradiated and stored at 40° C./75% RH for 10 months, L/N0203149-NI. (C), bottom left, provides in vitro release profiles of ZP-Zolmitriptan M207 1.9 mg patches that have been E-beam irradiated and stored at 40° C./75% RH for 10 months, L/N0203149-IR.

FIG. 7 is a line graph of mean zolmitriptan and sumatriptan plasma concentrations over time (zero to 24 hours) in normal human volunteers, wherein Treatment A is the M207 system (0.48 mg); Treatment B is the M207 system (0.48 mg×2); Treatment C is the M207 system (1.9 mg); Treatment D is the zolmitriptan (2.5 mg oral tablet); Treatment E is the Sumatriptan (6.0 mg SC using auto-injector pen); Treatment F is the Zolmitriptan system (1.9 mg×2); and Treatment G is the Zolmitriptan system (3.8 mg). Sumatriptan was scaled 6/90 to show the sumatriptan concentration-time profile relative to other treatments.

DETAILED DESCRIPTION OF SPECIFIC EMBODIMENTS

Figure 8:
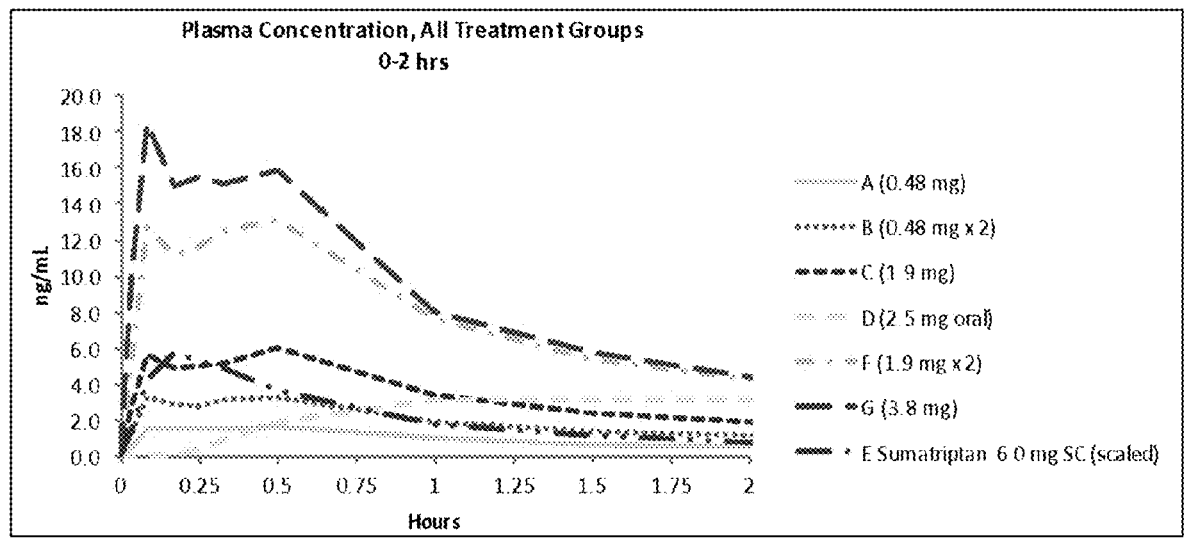
FIG. 8 is a line graph of mean zolmitriptan and sumatriptan plasma concentrations over time (zero to two hours), wherein Treatment A is the M207 system (0.48 mg); Treatment B is the M207 system (0.48 mg×2); Treatment C is the M207 system (1.9 mg); Treatment D is Zolmitriptan (2.5 mg oral tablet); Treatment E is the Sumatriptan (6.0 mg SC using auto-injector pen); Treatment F is the Zolmitriptan system (1.9 mg×2); and Treatment G is the Zolmitriptan system (3.8 mg). In the graph, sumatriptan was scaled 6/90 to show the sumatriptan concentration-time profile relative to other treatments.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

I. Introduction

Applicant surprisingly found, inter alia, that a dose of zolmitriptan typical of that of an oral delivery was well tolerated in delivery routes other than oral delivery, e.g., such as the intracutaneous or transdermal delivery of zolmitriptan as described herein. In accordance with this disclosure, the delivery of zolmitriptan generally comprises a delivery system comprising a microprojection member (or system) that includes a plurality of microprojections (or array thereof) that are adapted to penetrate or pierce the stratum corneum into the underlying epidermis layer, or epidermis and dermis layers. Applicant, through significant trial and error and development efforts, customized the transdermal delivery of zolmitriptan. In one embodiment, the microprojection member includes a biocompatible coating comprising zolmitriptan. This system provides superior pharmacokinetics and pharmacodynamics over existing therapies and can be extended to other triptans useful for treating migraines, cluster headaches, and other diseases or conditions.

II. Definitions

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

The term "amorphous" means a non-crystalline solid, i.e., a solid that lacks the long-range order that is characteristic of a crystal.

The term "area under the curve" or "AUC" means the area under the curve (mathematically known as definite integral) in a plot of concentration of drug in blood plasma against time. Typically, the area is computed starting at the time the drug is administered and ending when the concentration in plasma is negligible. In practice, the drug concentration is measured at certain discrete points in time and the trapezoidal rule is used to estimate AUC.

The term "biocompatible coating," as used herein, means and includes a coating formed from a "coating formulation" that has sufficient adhesion characteristics and no (or minimal) adverse interactions with the biologically active agent (a/k/a active pharmaceutical ingredient, or therapeutic agent, or drug).

The term "bioequivalent," as used herein, denotes a scientific basis on which two or more pharmaceutical products, compositions or methods containing same active ingredient are compared with one another. "Bioequivalence" means the absence of a significant difference in the rate and extent to which the active agent in pharmaceutical equivalents or pharmaceutical alternatives becomes available at the site of action when administered in an appropriately designed study. Bioequivalence can be determined by an in vivo study comparing a pharmacokinetic parameter for the two compositions. Parameters often used in bioequivalence studies are $T_{max}$, $C_{max}$, $AUC_{0-inf}$, $AUC_{0-t}$. In the present context, substantial bioequivalence of two compositions or products is established by 90% confidence intervals (CI) of between 0.80 and 1.25 for AUC and $C_{max}$.

The term "cluster" as used herein refers to a series of recurring cluster headaches. Cluster duration is usually from one week to one year, although in chronic cluster headache the duration exceeds one year. The end of a cluster is identified by at least 1 month of remission.

The term "cluster headache" as used herein refers to a condition characterized by excruciating headache pain that recurs, usually daily (although bouts may recur up to 8 times per day), for a period of a week or longer. Cluster headaches pain is usually localized on one side of the head ("unilateral") usually the same side although in some patients the side can vary. The pain usually reaches full intensity in under 10 minutes and lasts for between 15 minutes and 3 hours (usually between 30 and 60 minutes). Because of the rapid onset of symptoms and short duration, treatment via a route by which the drug is rapidly absorbed is required.

The term "coating formulation," as used herein, means and includes a freely flowing composition or mixture, which is employed to coat a delivery surface, including one or more microprojections and/or arrays thereof.

The term "degradation," as used herein, means the purity of the biological agent decreases from an initial time point.

The term "desiccant," as used herein, means an agent that absorbs water, usually a chemical agent.

The term "deteriorate," as used herein, means that the biologically active agent is diminished or impaired in quality, character, or value.

The term "electrotransport" refers, in general, to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent, or, for "reverse" electrotransport, samples or enhances sampling of the agent. The electrotransport of the agents into or out of the human body may be attained in various manners.

The term "half life" as used herein refers to the time required for a drug's blood or plasma concentration to decrease by one half. This decrease in drug concentration is a reflection of its excretion or elimination after absorption is complete and distribution has reached an equilibrium or quasi-equilibrium state. The half life of a drug in the blood may be determined graphically from a pharmacokinetic plot of a drug's blood-concentration time plot, typically after intravenous administration to a sample population. The half life can also be determined using mathematical calculations that are well known in the art. Further, as used herein the term "half life" also includes the "apparent half-life" of a drug. The apparent half life may be a composite number that accounts for contributions from other processes besides elimination, such as absorption, reuptake, or enterohepatic recycling.

The term "headache pain scale" as used herein means a scale used to allow patients to quantify their level of pain. Preferably a scale of 0-3 is used, wherein severe pain has a pain score of 3, moderate pain has a score of 2, mild pain has a score of 1, and no pain (also referred to as "pain freedom") has a score of 0.

The word "intracutaneous" as used herein, is a generic term that refers to delivery of an active agent (e.g., a therapeutic agent, such as a drug, pharmaceutical, peptide, polypeptide or protein) through the skin to the local tissue or systemic circulatory system without substantial cutting or penetration of the skin, such as cutting with a surgical knife or piercing the skin with a hypodermic needle. Intracutaneous agent delivery includes delivery via passive diffusion as well as delivery based upon external energy sources, such as electricity (e.g., iontophoresis) and ultrasound (e.g., phonophoresis).

The term "intracutaneous flux," as used herein, means the rate of intracutaneous delivery of a drug.

The term "microprojection member" or "microneedle array," and the like as used herein, generally connotes a microprojection grouping comprising a plurality of microprojections, preferably arranged in an array, for penetrating or piercing the stratum corneum. The microprojection member can be formed by etching or punching a plurality of microprojections from a thin sheet of metal or other rigid material, and folding or bending the microprojections out of the plane of the sheet to form a configuration. The microprojection member could alternatively be fabricated with other materials, including plastics or polymers, such as polyetheretherketone (PEEK). The microprojection member can be formed in other known techniques, such as injecting molding or micro-molding, microelectromechanical systems (MEMS), or by forming one or more strips having microprojections along an edge of each of the strip(s), as disclosed in U.S. Pat. Nos. 6,083,196; 6,091,975; 6,050,988; 6,855,131; 8,753,318; 9,387,315; 9,192,749; 7,963,935; 7,556,821; 9,295,714; 8,361,022; 8,633,159; 7,419,481; 7,131,960; 7,798,987; 7,097,631; 9,421,351; 6,953,589; 6,322,808; 6,083,196; 6,855,372; 7,435,299; 7,087,035; 7,184,826; 7,537,795; 8,663,155, and U.S. Pub. Nos. US20080039775; US20150038897; US20160074644; and US20020016562. As will be appreciated by one having ordinary skill in the art, when a microprojection array is employed, the dose of the therapeutic agent that is delivered can also be varied or manipulated by altering the microprojection array size, density, etc.

The term "microprojections" and "microneedles," as used interchangeably herein, refers to piercing elements that are adapted to penetrate, pierce or cut into and/or through the stratum corneum into the underlying epidermis layer, or epidermis and dermis layers, of the skin of a living animal, particularly a mammal and, more particularly, a human. In one embodiment of the invention, the piercing elements have a projection length less than 1000 microns. In a further embodiment, the piercing elements have a projection length of less than 500 microns, more preferably less than 400 microns. The microprojections further have a width in the range of approximately 25 to 500 microns and a thickness in the range of approximately 10 to 100 microns. The microprojections may be formed in different shapes, such as needles, blades, pins, punches, and combinations thereof.

The terms "minimize" or "alleviate" as used herein means reduce.

"Most bothersome other symptom" means a symptom, usually a migraine symptom, that is most bothersome to a patient, in addition to pain. Preferably, a most bothersome other symptom is identified by a patient at the start of a clinical trial. Usually, most bothersome other symptom is selected from nausea, photophonia, and phonophobia.

"Most bothersome other symptom freedom" means the patient reports an absence of the most bothersome other symptom at one or more pre-specified times after drug administration. Preferred times for migraine patients are 1 hour, 2 hours, and 4 hours. Preferred times for cluster headache patients are 15 minutes and 30 minutes.

"Nausea freedom" means the patient reports the absence of nausea at a pre-specified time period after drug administration.

"Optional" or "optionally" means that the subsequently described element, component or circumstance may or may not occur, so that the description includes instances where the element, component, or circumstance occurs and instances where it does not.

"Pain freedom" means the patient reports an absence of headache pain (headache pain score=0) at one or more pre-specified time after drug administration. Preferred times for migraine patients are 1 hour, 2 hours, and 4 hours. Preferred times for cluster headache patients are 15 minutes and 30 minutes.

"Pain relief" means the patient reports a reduction in headache pain, a reduction from moderate or severe pain (headache pain score=3 or 2) to mild or no pain (headache pain score=1 or 0), at one or more pre-specified time period after drug administration. Preferred times for migraine patients are 1 hour, 2 hours, and 4 hours. Preferred times for cluster headache patients are 15 minutes and 30 minutes.

"Phonophobia" refers to a fear of or aversion to sounds, especially loud sounds.

"Phonophobia freedom" means the patient reports the absence of phonophobia at a pre-specified time period after drug administration.

"Photophobia" refers to increased, often painful sensitivity to light, especially bright light.

"Photophobia freedom" means the patient reports the absence of photophobia at a pre-specified time period after drug administration.

"Partial AUC" means an area under the drug concentration-time curve (AUC) calculated using linear trapezoidal summation for a specified interval of time, for example, AUC(0-1 hr), AUC(0-2 hr), AUC(0-4 hr), AUC(0-6 hr), AUC(0-8 hr) etc.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid.

The term "stable," as used herein, refers to an agent formulation, means the agent formulation is not subject to undue chemical or physical change, including decomposition, breakdown, or inactivation. "Stable" as used herein, refers to a coating also means mechanically stable, i.e., not subject to undue displacement or loss from the surface upon which the coating is deposited.

The terms "subject" or "patient" are used interchangeably herein and refer to a vertebrate, preferably a mammal. Mammals include, but are not limited to, humans.

The terms "therapeutic-effective" or "therapeutically-effective amount," as used herein, refer to the amount of the biologically active agent needed to stimulate or initiate the desired beneficial result. The amount of the biologically active agent employed in the coatings of the invention will be that amount necessary to deliver an amount of the biologically active agent needed to achieve the desired result. In practice, this will vary widely depending upon the particular biologically active agent being delivered, the site of delivery, and the dissolution and release kinetics for delivery of the biologically active agent into skin tissues.

The term "transdermal," as used herein, means the delivery of an agent into and/or through the skin for local or systemic therapy.

The term "transdermal flux," as used herein, means the rate of transdermal delivery.

The term "$T_{max}$" refers to the time from the start of delivery to $C_{max}$, the maximum plasma concentration of the biologically active agent.

The term "package" or "packaging" will be understood to also include reference to "storage" or "storing."

The term "zolmitriptan" includes, without limitation, zolmitriptan salts, simple derivatives of zolmitriptan and closely related molecules.

III. Intracutaneous Delivery System

In one embodiment, the intracutaneous delivery system is a transdermal or intracutaneous drug delivery technology which comprises a disposable patch comprised of a microprojection member centered on an adhesive backing. The microprojection member comprises titanium (or other rigid material, including a plastic or polymeric material like polyetheretherketone (PEEK)) microneedles that are coated with a dry drug product formulation. The patch is mounted in a retainer ring to form the patch assembly. The patch assembly is removably mounted in a handheld applicator to form the intracutaneous delivery system. The applicator ensures that the patch is applied with a defined application speed and energy to the site of intracutaneous administration. The applicator may be designed for single use or be reusable.

More particularly, the patch can comprise an array of about 3 to 6 cm$^2$ of titanium microneedles approximately 200-350 microns long, coated with a hydrophilic formulation of the relevant drug, and attached to an adhesive backing. The maximum amount of active drug that can be coated on a patch's microneedle array depends on the active moiety of the drug formulation, the weight of the excipients in the drug formulation, and the coatable surface area of the microneedle array. For example, patches with about 1 cm$^2$, 2 cm$^2$, 3 cm$^2$, 4 cm$^2$, 5 cm$^2$, and 6 cm$^2$ microneedle arrays may be employed. The patch is applied with a hand-held applicator that presses the microneedles into the skin to a substantially uniform depth in each application, close to the capillary bed, allowing for dissolution and absorption of the drug coating, yet short of the nerve endings in the skin. The typical patch wear time is about 15 to 45 minutes or less, decreasing the potential for skin irritation. Nominal applicator energies of about 0.20 to 0.60 joules are generally able to achieve a good balance between sensation on impact and array penetration. The actual kinetic energy at the moment of impact may be less than these nominal values due to incomplete extension of the applicator's spring, energy loss from breaking away the patch from its retainer ring, and other losses, which may comprise approximately total 25% of the nominal.

A. Array Design

Figure 31:
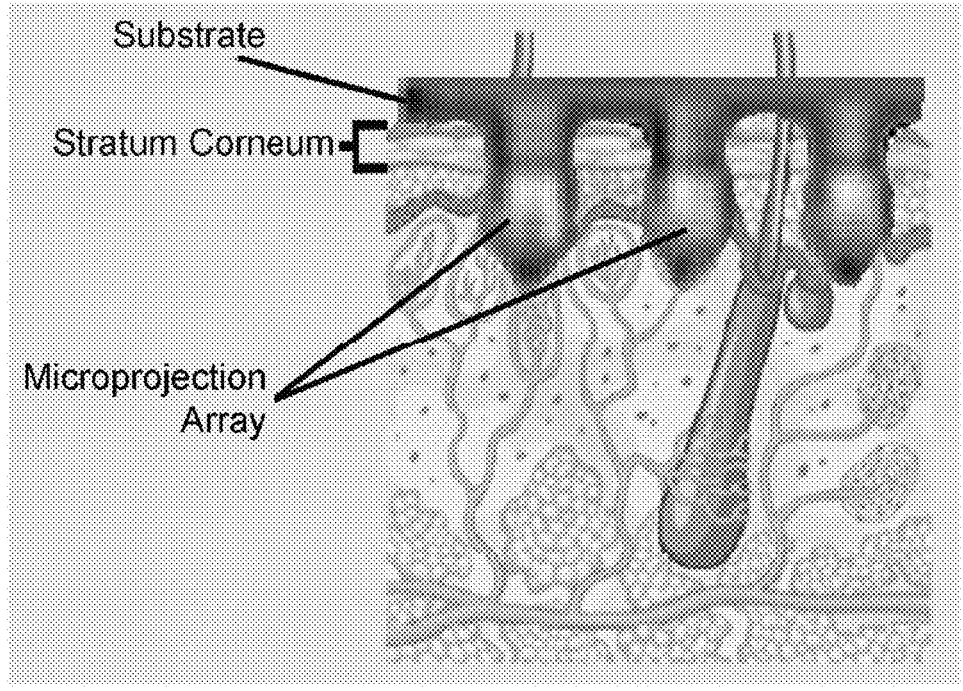
FIG. 31 depicts the interaction of microprojections with the skin, and, specifically, how the microprojections penetrate the stratum corneum for effective drug delivery.

A number of variables play a role in the type of array utilized for a particular active agent. For example, different shapes (e.g., shapes similar to an arrowhead as shown in FIG. 31, hook, conical, or the Washington monument, FIG. 1(A)-(B)) may enable higher drug loading capacity, while the length of the microprojections may be increased to provide more driving force for penetration. The stratum corneum has a thickness of about 10-40 μm, and microprojections must have an adequate size, thickness, and shape to penetrate and effect drug delivery through the stratum corneum. FIG. 31, not drawn to scale, demonstrates how an array interacts with the skin, such that the microprojections penetrate the stratum corneum and the substrate interfaces with the surface of the skin. It is advantageous to achieve a thicker coating on the microprojections, which will penetrate the stratum corneum, while avoiding applying coating to the substrate or the base ("streets") of the array, which will not penetrate the stratum corneum. A larger surface area allows for a thicker coating without extending to the base or streets of the array. The coating is applied only to the microprojections. Further, the higher penetration force required for a more bulky projection with coating may be compensated by a longer length and lower density of projections per cm$^2$.

Exemplary intracutaneous delivery systems that may be used in the present disclosure include the drug delivery technologies described in U.S. Pat. Nos. 6,083,196; 6,091,975; 6,050,988; 6,855,131; 8,753,318; 9,387,315; 9,192,749; 7,963,935; 7,556,821; 9,295,714; 8,361,022; 8,633,159; 7,419,481; 7,131,960; 7,798,987; 7,097,631; 9,421,351; 6,953,589; 6,322,808; 6,083,196; 6,855,372; 7,435,299; 7,087,035; 7,184,826; 7,537,795; 8,663,155, and U.S. Pub. Nos. US20080039775; US20150038897; US20160074644; and US20020016562. The disclosed systems and apparatus employ piercing elements of various shapes and sizes to pierce the outermost layer (i.e., the stratum corneum) of the skin, and thus enhance the agent flux. The piercing elements generally extend perpendicularly from a thin, flat substrate member, such as a pad or sheet. The piercing elements are typically small, some having a microprojection length of only about 25 to 400 microns and a microprojection thickness of about 5 to 50 microns. These tiny piercing/cutting elements make correspondingly small microslits/microcuts in the stratum corneum for enhanced transdermal/intracutaneous agent delivery. The active agent to be delivered is associated with one or more of the microprojections, preferably by coating the microprojections with a triptan- or zolmitriptan-based formulation to form a solid, dry coating, or optionally, by the use of a reservoir that communicates with the stratum corneum after the microslits are formed, or by forming the microprojections from solid triptan-based formulations that dissolve after application. The microprojections can be solid or can be hollow, and can further include device features adapted to receive and/or enhance the volume of the coating, such as apertures, grooves, surface irregularities or similar modifications, wherein the features provide increased surface area upon which a greater amount of coating can be deposited. The microneedles may be constructed out of stainless steel, titanium, nickel titanium alloys, or similar biocompatible materials, such as polymeric materials.

The present disclosure therefore encompasses patches and microneedle arrays having the following features:

Patch size: About 1 to 20 cm$^2$, or about 2 to 15 cm$^2$, or about 4 to 11 cm$^2$, or about 5 cm$^2$, or about 10 cm$^2$.

Substrate size: About 0.5 to 10 cm$^2$, or about 2 to 8 cm$^2$, or about 3 to 6 cm$^2$, or about 3 cm$^2$, or about 3.13 cm$^2$, or about 6 cm$^2$.

Array size: About 0.5 to 10 cm$^2$, or about 2 to 8 cm$^2$, or about 2.5 to 6 cm$^2$, or about 2.7 cm$^2$, or about 5.5 cm$^2$. or about 2.74 cm$^2$, or about 5.48 cm$^2$.

Density (microprojections/cm$^2$): At least about 10 microprojections/cm$^2$, or in the range of about 200 to 2000 microprojections/cm$^2$, or about 500 to 1000 microprojections/cm$^2$, or about 650 to 800 microprojections/cm$^2$, or approximately 725 microprojections/cm$^2$ Number of microprojections/array: About 100 to 4000, or about 1000 to 3000, or about or about 1500 to 2500, or about 1900 to 2100, or about 2000, or about 1987, or about 200 to 8000, or about 3000 to 5000, or about or about 3500 to 4500, or about 4900 to 4100, or about 4000, or about 3974.

Microprojection length: About 25 to 600 microns, or about 100 to 500 microns, or about 300 to 450 microns, or about 320 to 410 microns, or about 340 microns, or about 390 microns, or about 387 microns. In other embodiments, the length is less than 1000 microns, or less than 700 microns, or less than 500 microns. Accordingly, the microneedles penetrate the skin to about 25 to 1000 microns.

Tip length: About 100 to 250 microns, or about 130 to about 200 microns, or about 150 to 180 microns, or about 160 to 170 microns, or about 165 microns.

Microprojection width: About 10 to 500 microns, or about 50 to 300 microns, or about 75 to 200 microns, or about 90 to 160 microns, or about 250 to 400 microns, or about 300 microns, or about 100 microns, or about 110 microns, or about 120 microns, or about 130 microns, or about 140 microns, or about 150 microns Microprojection thickness: about 1 micron to about 500 microns, or about 5 microns to 300 microns, or about 10 microns to 100 microns, or about 10 microns to 50 microns, or about 20 microns to 30 microns, or about 25 microns.

Tip angle: about 10-70 degrees, or about 20-60 degrees or about 30 to 50 degrees, or about 35 to 45 degrees, or about 40 degrees.

Total active agent per array: About 0.1 mg to 10 mg, or about 0.5 mg to 5 mg, or about 1 mg to 4 mg, or about 1 mg, or about 1.9 mg, or about 3.8 mg.

Amount of inactive ingredient per array: About 0.1 to 10 mg, or about 0.2 to 4 mg, or about 0.3 mg to 2 mg, or about 0.6 mg, or about 0.63 mg, or about 1.3 mg, or about 1.26 mg. Alternatively, the amount of inactive ingredient is from one to three times less than the active agent, or from about 0.033 mg to about 3.33 mg.

Coating Thickness: about 100 µm to about 500 µm, or about 200 µm to about 350 µm, or about 250 µm to about 290 µm, or about 270 µm.

Active agent per microprojection: About 0.01 to about 100 µg, or about 0.1 to 10 µg, or about 0.5 to 2 µg, or about 1 µg, or about 0.96 µg.

A particularly preferred embodiment has a patch area of about 5 cm$^2$ adhered to a titanium substrate with an area of about 3.1 cm$^2$ and a thickness of about 25 µm. The substrate is comprised of a microprojection array with an area of about 2.74 cm$^2$ containing about 1987 microprojections at a density of about 725 microprojections/cm$^2$. The dry formulation contained on each microprojection may have the approximate shape of an American football with a thickness that tapers down from a maximum of about 270 µm and consists of about 0.96 µg of zolmitriptan and about 0.32 of tartaric acid, or about 1.9 mg of zolmitriptan and about 0.63 mg of tartaric acid per patch.

Figure 32:
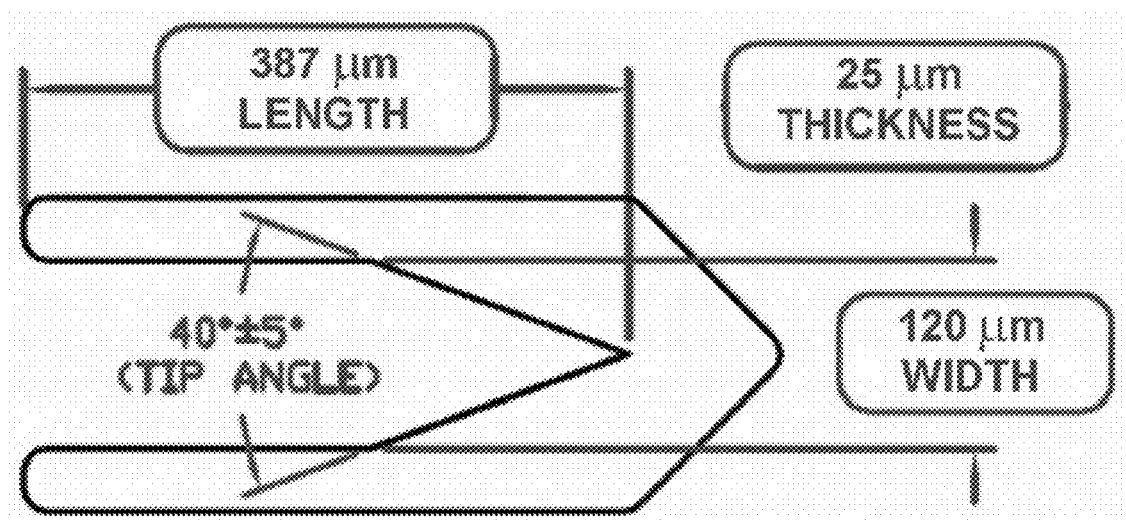
FIG. 32 demonstrates an embodiment of a microprojection with a shape and dimensions before the microprojection is bent outward from the substrate and coated with drug.

FIG. 32 demonstrates the shape of the microprojection, in a preferred embodiment, prior to bending (forming). Array forming is a process that bends the individual microprojections at right angles to the plane of the substrate. An array is placed over the forming tool, which contains cavities that are registered with the microprojections. An elastomeric forming disk is placed on top of the array and forced under pressure into the cavities in the forming tool. The elastomer flows into the cavities, causing the microprojections to be bent to the desired angle. The use of the elastomer has the advantage that no careful registration of the forming disk to the microprojections and the cavities is required in order to have effective array forming. As shown in FIG. 32, the microprojections may be substantially rectangular, with a width of about 120±13 µm and a thickness of about 25.4±2.5 µm. The microprojections end with a triangular tip to facilitate penetration. The tip has an angle of 40±5 degrees, and is about 165±25 microns long. Prior to bending (forming) out from the substrate, the microprojections have a length of about 387±13 µm, and after bending, they protrude perpendicular to the substrate about 340 µm.

Another preferred embodiment has a patch area of about 5 cm$^2$ adhered to a titanium substrate of about 6 cm$^2$ to and a thickness of about 25 µm. The substrate is comprised of an array with an area of about 5.5 cm$^2$ containing about 4000 microprojections at a density of about 725 microprojections/cm$^2$. The dry formulation contained on each microprojection is in the approximate shape of an American football with a thickness that tapers down from a maximum of about 270 and consists of about 0.96 µg of zolmitriptan and about 0.32 of tartaric acid, or about 3.8 mg of zolmitriptan and about 1.3 mg of tartaric acid per patch. The microprojections have a length of about 387±13 µm, a width of about 120±13 µm, and a thickness of about 25.4±2.5 µm. The microprojections are rectangular, with a triangular tip to facilitate penetration. The tip has an angle of 40±5 degrees, and is about 165±25 microns long.

The exact combination of bulk, length, and density that produces the desired penetration will vary, and may depend on the drug, its dose, the disease or condition to be treated and the frequency of administration. Thus, the drug delivery efficiency of a particular array (i.e., the amount of drug delivered to the bloodstream) will vary between about 40% to 100%, or about 40%, or about 50%, or about 60%, or about 70%, or about 80%, or about 90%, or about 100%.

B. Impact Applicator

As illustrated in FIGS. 4(A)-(B), 5(A)-(E), the intracutaneous drug delivery system of the present disclosure may further comprise an impact applicator having a body and a piston movable within the body, wherein the surface of the piston impacts the patch against the skin causing the microprojections to pierce the stratum corneum. The applicator is adapted to apply the microneedle array to the stratum corneum with an impact energy density of at least 0.05 joules per cm$^2$ in 10 milliseconds or less, or about 0.26 joules per cm$^2$ in 10 milliseconds or less, or about 0.52 joules per cm$^2$ in 10 milliseconds or less.

As illustrated in FIGS. 2(A) and 2(B), the intracutaneous delivery system comprises a patch having an adhesive backing on one surface and a shiny metal surface on the other side comprised of the array of drug-coated microneedles. The patch may be applied to the skin by pressing the shiny metal surface against the skin either manually, or preferably by an applicator. Preferably, the applicator applies the patch to the skin with an impact energy density of 0.26 joules per cm$^2$ in 10 milliseconds or less. As shown on FIGS. 2A, 2B, 3A and 3B, the patch may be connected to and supported by a retainer ring structure forming a patch assembly. The retainer ring is adapted to fit onto the impact adaptor and removably attach the patch to the applicator. The retainer ring structure may comprise an inner ring and outer ring, which are designed to receive the adhesive patch and microneedle array. FIGS. 5(A)-(E) demonstrate one embodiment of the claimed invention, in which the user facilitates the connection of the impact applicator to the retainer ring, which is already loaded with the patch and the microneedle array. As shown, once the retainer ring and impact applicator are connected, a user can unlock the impact applicator by twisting the applicator cap. FIG. 5(C) shows that the user may then press the applicator downward on the skin to dispense the patch and apply it to the skin. The patch will removably attach to the patient's skin, and the retainer ring remains attached to the applicator. As shown in FIGS. 4(A) and 4(B), the retainer ring reversibly attaches to the impact applicator such that the impact applicator can be reused during subsequent dosing events with additional patch assemblies and potentially for other active ingredients and disease states.

In another embodiment, the patch and applicator are supplied as a single, integrated unit, with packaging that ensures the stability and sterility of the formulation. The user removes the system from the packaging and applies the patch much as described above. The used applicator is then disposed of. This embodiment, while somewhat higher cost per dose, provides a system that is less complex, smaller, lighter, and easier to use.

The present disclosure can also be employed in conjunction with a wide variety of active transdermal systems (as opposed to passive, manual intracutaneous delivery devices described herein), as the disclosure is not limited in any way in this regard.

Some active transdermal systems utilize electrotransport. Illustrative electrotransport drug delivery systems are disclosed in U.S. Pat. Nos. 5,147,296; 5,080,646; 5,169,382 and 5,169,383, the disclosures of which are incorporated by reference herein in their entirety. One widely used electrotransport process, iontophoresis, involves the electrically induced transport of charged ions. Electroosmosis, another type of electrotransport process involved in the transdermal transport of uncharged or neutrally charged molecules (e.g., transdermal sampling of glucose), involves the movement of a solvent with the agent through a membrane under the influence of an electric field. Electroporation, still another type of electrotransport, involves the passage of an agent through pores formed by applying an electrical pulse, a high voltage pulse, to a membrane. In many instances, more than one of the noted processes may be occurring simultaneously to different extents. Accordingly, the term "electrotransport" is given herein its broadest reasonable interpretation, to include the electrically induced or enhanced transport of at least one charged or uncharged agent, or mixtures thereof, regardless of the specific mechanism(s) by which the agent is actually being transported with.

In addition, any other transport enhancing method, including but not limited to chemical penetration enhancement, laser ablation, heat, ultrasound, or piezoelectric devices, can be used in conjunction with the disclosure herein.

IV. Active Agents and Biocompatible Coating

The coating formulations applied to the microprojection member described above to form solid coatings are comprised of a liquid, preferably an aqueous formulation having at least one biologically active agent, which can be dissolved within a biocompatible carrier or suspended within the carrier. The biologically active agent may be a triptan, including zolmitriptan, sumatriptan, rizatriptan, naratriptan, eletriptan, almotriptan, frovatriptan, avitriptan, and donitriptan, and pharmaceutically acceptable salts, fragments, analogs, or prodrugs thereof. Preferably, the biologically active agent is zolmitriptan.

Examples of pharmaceutically acceptable salts include, without limitation, acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylate, malonate, adipate, citraconate, glutarate, itaconate, mesaconate, citramalate, dimethylolpropionate, tiglate, glycerate, methacrylate, isocrotonate, β-hydroxibutyrate, crotonate, angelate, hydracrylate, ascorbate, aspartate, glutamate, 2-hydroxyisobutyrate, lactate, malate, pyruvate, fumarate, tartrate, nitrate, phosphate, benzene sulfonate, methane sulfonate, sulfate and sulfonate.

The concentration of biologically active ingredient and excipients must be carefully controlled to achieve the desired amount of the active ingredient with an acceptable coating thickness, avoid wicking of the coating formulation onto the base of the microneedle array, maintain the uniformity of the coating, and ensure stability. In one embodiment, the active agent is present in the coating formulation at a concentration of between about 1% w/w to about 60% w/w, preferably between about 15% and 60%, or more preferably between 35% and 45%. The formulation may further comprise an acid at a concentration of between about 0.1% w/w to about 20% w/w. Such acid may be selected from tartaric acid, citric acid, succinic acid, malic acid, maleic acid, ascorbic acid, lactic acid, hydrochloric acid, either individually or in combination. In another embodiment, in the coating formulation, the active agent to acid ratio is about 1:1, about 2:1, about 3:1, about 4:1, or about 5:1. The present disclosure further encompasses a coating formulation comprising about 33% w/w zolmitriptan base and about 11% w/w tartaric acid. In some embodiments, the acid is one of tartaric acid, citric acid, succinic acid, malic acid or maleic acid, and is present in an amount of about 0.33% to 10% w/w, or about 8.33% to about 16.67% w/w, or about 13.33% w/w, or about 15% w/w, or about 6.67% w/w. In some embodiments, the coating formulation comprises 45% w/w of the active agent, 15% w/w of the acid, and 40% w/w of water.

Surfactants may be included in the coating formulation. Surfactants suitable for inclusion in the coating formulations include, but are not limited to, polysorbate 20 and polysorbate 80. Surfactants are commonly used to improve drug delivery as penetration enhancers. However, Applicant found that surfactants resulted in undulations in the coating formulation, which is indicative of an uneven film and is highly disadvantageous. Applicant found that the need for surfactants and other penetration enhancers can be avoided through the use of the claimed invention—specifically, through the claimed zolmitriptan transdermal delivery patches. Furthermore, Applicant surprisingly found that microneedle coating avoided wicking, and the coating sufficiently adhered to the microprojections during the manufacturing process of the microneedle arrays, despite the lack of a surfactant.

Antioxidants may be included in the coating formulation. Antioxidants suitable for inclusion in the coating formulations include, but are not limited to, methionine, ascorbic acid, and EDTA.

The coating formulation further comprises a liquid, preferably water, in an amount sufficient (qs ad) to bring the formulation to 100% prior to being dried onto the microneedles. The pH of the liquid coating formulation may be below about pH 8. In other cases, the pH is between about pH 3 and 7.4, or between about pH 3.5 to 4.5.

Representative examples of liquid coating formulations according to the present disclosure are set forth in Table 1 below. The coatings generally contain at least one acid.

TABLE 1

| Ingredient* | Coating Formulations | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Zolmitriptan | 25-50 | 1-30 | 45 | 40 | 45 | 40 | 45 | 40 | 45 | 40 |
| Tartaric acid | 0-16.67 | 0-10 | 0-15 | 0-13.33 | 0-15 | 0-13.33 | 0-15 | 0-13.33 | 0-15 | 0-13.33 |
| Citric acid | 0-16.67 | 0-10 | 0-15 | 0-13.33 | 0-15 | 0-13.33 | 0-15 | 0-13.33 | 0-15 | 0-13.33 |
| Succinic acid | 0-16.67 | 0-10 | 0-15 | 0-13.33 | 0-15 | 0-13.33 | 0-15 | 0-13.33 | 0-15 | 0-13.33 |

TABLE 1-continued

Coating Formulations

| Ingredient* | 1 | 2 | 3 | 4 | 5 | 6 | 7 | 8 | 9 | 10 |
|---|---|---|---|---|---|---|---|---|---|---|
| Malic acid | 0-16.67 | 0-10 | 0-15 | 0-13.33 | 0-15 | 0-13.33 | 0-15 | 0-13.33 | 0-15 | 0-13.33 |
| Maleic acid | 0-16.67 | 0-10 | 0-15 | 0-13.33 | 0-15 | 0-13.33 | 0-15 | 0-13.33 | 0-15 | 0-13.33 |
| Ascorbic acid | 0-5 | 0-5 | 0-5 | 0-5 | 0-5 | 0-5 | 0-5 | 0-5 | 0-5 | 0-5 |
| Lactic acid | 0-10 | 0-10 | 0-10 | 0-10 | 0-10 | 0-10 | 0-10 | 0-10 | 0-10 | 0-10 |
| Surfactants (e.g. polysorbate 20, polysorbate 80) | 0-0.2 | 0 | 0 | 0 | 0.2 | 0.2 | 0 | 0 | 0 | 0 |
| EDTA (Antioxidant Chelator) | 0-0.01 | 0 | 0 | 0 | 0 | 0 | 0.01 | 0.01 | 0 | 0 |
| Methionine (Antioxidant) | 0-1 | 0 | 0 | 0 | 0 | 0 | 0 | 0 | 1 | 1 |
| Deionized water | qs 100% | qs 100% | qs 100% | qs 100% | qs 100% | qs 100% | qs 100% | qs 100% | qs 100% | qs 100% |

*Ingredients are expressed in % w/w

The present disclosure contemplates that sumatriptan or other triptan may be substituted for zolmitriptan in similar amounts or proportions as described above.

The liquid coating formulations according to the present disclosure generally exhibit the ability to consistently coat the microneedles with adequate content and morphology, and result in a stable solid-state (dried) formulation, containing less than 5% water, preferably less than 3%. The liquid formulations are applied to the microneedle arrays and the microprojection tips thereof using an engineered coater which allows accurate control of the depth of the microprojection tips dipping into the liquid film. Examples of suitable coating techniques are described in U.S. Pat. No. 6,855,372, included herein by reference in its entirety. Accordingly, the viscosity of the liquid plays a role in microprojection member coating process as has been described. See Ameri, M.; Fan, S C.; Maa, Y F (2010); "Parathyroid hormone PTH(1-34) formulation that enables uniform coating on a novel transdermal microprojection delivery system;" Pharmaceutical Research, 27, pp. 303-313; see also Ameri M, Wang X, Maa Y F (2010); "Effect of irradiation on parathyroid hormone PTH(1-34) coated on a novel transdermal microprojection delivery system to produce a sterile product—adhesive compatibility;" Journal of Pharmaceutical Sciences, 99, 2123-34.

The coating formulations comprising zolmitriptan have a viscosity less than approximately 500 centipoise (cP) and greater than 3 cP, or less than approximately 400 cP and greater than 10 cP, or less than approximately 300 cP and greater than 50 cP, or less than 250 cP and greater than approximately 100 cP. In some embodiments, the viscosity of the liquid formulation prior to coating is at least 20 cP. In other embodiments, the viscosity is about 25 cP, or about 30 cP, or about 35 cP, or about 40 cP, or about 45 cP, or about 50 cP, or about 55 cP, or about 60 cP, or about 65 cP, or about 70 cP, or about 75 cP, or about 80 cP, or about 85 cP, or about 90 cP, or about 95 cP, or about 100 cP, or about 150 cP, or about 200 cP, or about 300 cP, or about 400 cP, or about 500 cP. In other embodiments, the viscosity is more than about 25 cP, or a more than about 30 cP, or more than about 35 cP, or more than about 40 cP, or more than about 45 cP, or more than about 50 cP, or more than about 55 cP, or more than about 60 cP, or more than about 65 cP, or more than about 70 cP, or more than about 75 cP, or more than about 80 cP, or more than about 85 cP, or more than about 90 cP, or more than about 95 cP, or more than about 100 cP, or more than about 150 cP, or more than about 200 cP, or more than about 300 cP, or more than about 400 cP, or less than about 500 cP.

In a preferred embodiment, the viscosity of the coating formulation is more than about 80 cP and less than about 350 cP; in another preferred embodiment, the viscosity is more than about 100 cP and less than about 350 cP; and, in another preferred embodiment, the viscosity is more than about 100 cP and less than about 250 cP.

Once applied to the microprojections, the coating formulation may have an average thickness of about 10 to about 400 microns, or from about 30 to about 300 microns, or from about 100 microns to about 175 microns, or from about 115 to about 150 microns, or about 135 microns, as measured from the microprojection surface. Although it is preferable that the coating formulation have a uniform thickness covering the microprojection, the formulation may vary slightly as a result of the manufacturing process. As shown in FIG. 31, the microprojections are generally coated uniformly because they penetrate the stratum corneum. In some embodiments, the microprojections are not coated the entire distance from the tip to the base; instead, the coating covers a portion of the length of the microprojection, measured from tip to the base, of at least about 10% to about 80%, or 20% to about 70%, or about 30% to about 60%, or about 40% to about 50% of the length of the microprojection.

The liquid coating formulation is applied to an array of microprojections so as to deliver a dose of the active agent in the amount of about 0.1 mg to 10 mg per array. In the case of zolmitriptan, the dose is about 0.25 mg to about 10 mg, or about 1 mg or more, or about 1.9 mg or more, or about 2 mg or more, or about 3 mg or more, or about 3.8 mg or more, or about 4 mg or more, or about 5 mg or more delivered to the stratum corneum per array (via a patch or other form). In one embodiment, the amount of the zolmitriptan contained in coating formulation is 1-1000 μg or 10-100 μg. In one embodiment, the array size is about 5.5 cm$^2$ comprising a dose of about 3.8 mg zolmitriptan, or the array size is about 3 cm$^2$ comprising a dose of about 3.8 mg, or the array size is about 3 cm$^2$, comprising a dose of about 1.9 mg. The amount of zolmitriptan or similar active agent per microprojection could range from about 0.001 to about 1000 μg, or about 0.01 to about 100 μg, or about 0.1 to about 10 μg, or about 0.5 to about 2 μg. In one embodiment, the amount of zolmitriptan or similar active agent per microprojection is about 1 μg. The microprojection shape and size has a significant bearing on the drug loading capacity and on the effectiveness of drug delivery.

Importantly, the formulations of the present disclosure do not primarily rely on penetration enhancers to facilitate absorption of the active agent into the bloodstream. Penetration enhancers, such as Azone® and fatty acids, often cause skin irritation and have other disadvantages. Thus, the systems of the present disclosure are either completely free of a penetration enhancer, or are substantially free thereof. In other embodiments, there is less than 15% w/w of penetration enhancer present, or less than 10% w/w, or less than 5% w/w, or less than 2.5% w/w, or less than 1% w/w present in the dried formulation.

The biologically active agent formulations are generally prepared as a solid coating by drying a coating formulation on the microprojection, as described in U.S. Application Pub. No. 2002/0128599. The coating formulation is usually an aqueous formulation. During a drying process, all volatiles, including water are mostly removed; however, the final solid coating may still contain about 1% w/w water, or about 2% w/w water, or about 3% w/w water, or about 4% w/w water, or about 5% w/w water. The oxygen and/or water content present in the formulations are reduced by the use of a dry inert atmosphere and/or a partial vacuum. In a solid coating on a microprojection array, the drug may be present in an amount of less than about 10 mg per unit dose or less than about 4 mg or less than about 3 mg or less than about 2 mg or less than about 1 mg. With the addition of excipients, the total mass of solid coating may be less than about 15 mg per unit dose.

The microprotrusion member is usually present on an adhesive backing, which is attached to a disposable polymeric retainer ring. This assembly is packaged individually in a pouch or a polymeric housing. In addition to the assembly, this package contains a dead volume that represents a volume of at least 3 mL. This large volume (as compared to that of the coating) acts as a partial sink for water. For example, at 20° C., the amount of water present in a 3 mL atmosphere as a result of its vapor pressure would be about 0.05 mg at saturation, which is typically the amount of residual water that is present in the solid coating after drying. Therefore, storage in a dry inert atmosphere and/or a partial vacuum will further reduce the water content of the coating resulting in improved stability.

According to the disclosure, the coating can be applied to the microprojections by a variety of known methods. For example, the coating may be only applied to those portions of the microprojection member or microprojections that pierce the skin (e.g., tips). The coating is then dried to form a solid coating. One such coating method comprises dip-coating. Dip-coating can be described as a method to coat the microprojections by partially or totally immersing the microprojections into a coating solution. By use of a partial immersion technique, it is possible to limit the coating to only the tips of the microprojections.

A further coating method comprises roller coating, which employs a roller coating mechanism that similarly limits the coating to the tips of the microprojections. The roller coating method is disclosed in U.S. Application Pub. No. 2002/0132054. As discussed in detail therein, the disclosed roller coating method provides a smooth coating that is not easily dislodged from the microprojections during skin piercing.

A further coating method that can be employed within the scope of the present invention comprises spray coating. Spray coating can encompass formation of an aerosol suspension of the coating composition. In one embodiment, an aerosol suspension having a droplet size of about 10 to 200 picoliters is sprayed onto the microprojections and then dried.

Pattern coating can also be employed to coat the microprojections. The pattern coating can be applied using a dispensing system for positioning the deposited liquid onto the microprojection surface. The quantity of the deposited liquid is preferably in the range of 0.1 to 20 nanoliters/microprojection. Examples of suitable precision-metered liquid dispensers are disclosed in U.S. Pat. Nos. 5,916,524; 5,743,960; 5,741,554; and 5,738,728; which are fully incorporated by reference herein.

Microprojection coating formulations or solutions can also be applied using ink jet technology using known solenoid valve dispensers, optional fluid motive means and positioning means which is generally controlled by use of an electric field. Other liquid dispensing technology from the printing industry or similar liquid dispensing technology known in the art can be used for applying the pattern coating of this invention.

In one embodiment of the disclosure, the thickness of the dried coating formulations comprising zolmitriptan range from about 10 to 100 microns as measured from the microprojection surface, or from about 20 to 80 microns, or from about 30 to 60 microns, or from about 40 to 50 microns. The desired coating thickness is dependent upon several factors, including the required dose and, hence, coating thickness necessary to deliver the dose, the density of the microprojections per unit area of the sheet, the viscosity, the solubility and concentration of the coating composition and the coating method chosen. The thickness of coating applied to microprojections can also be adapted to optimize stability of the zolmitriptan. Known formulation adjuvants can also be added to the coating formulations provided they do not adversely affect the necessary solubility and viscosity characteristics of the coating formulation nor the physical integrity of the dried coating.

The coating is applied to the microneedles, which protrude from the base, or streets, of the microneedle array. The coating is applied to the tips of the microneedles, and is not intended to cover the microneedles and the surface of the microneedle array. This reduces the amount of drug per transdermal patch, which is advantageous in light of FDA Guidance on the danger of residual drug on transdermal delivery systems, which suggests that the amount of residual drug in a system should be minimized. See FDA Guidance for Industry, Residual Drug in Transdermal and Related Drug Delivery Systems (August 2011). Applicant's strategy was to maximize drug release into skin per unit area, without using an excess of drug for coating.

After a coating has been applied, the coating formulation is dried onto the microprojections by various means. The coated microprojection member may be dried in ambient room conditions. However, various temperatures and humidity levels can be used to dry the coating formulation onto the microprojections. Additionally, the coated member can be heated, stored under vacuum or over desiccant, lyophilized, freeze dried or similar techniques used to remove the residual water from the coating.

Coating was conducted at ambient temperature utilizing a roller drum, rotating at 50 rpm, in a drug formulation reservoir (2 mL in volume) to produce a film of controlled thickness of around 270 µm in thickness. Further information about the coating process can be found in U.S. Pat. No. 6,855,372, incorporated herein in its entirety by reference. Microprojection arrays are dipped into the drug film, and the amount of coating is controlled by the number of dips (passes) through the drug film.

During the drying process, there may be issues related to forming a uniform coating the microprojection with a controlled and consistent thickness. One common issue in transdermal patch coating, called "dripping" or "teardrop" formations, occurs when the coating is drying and the coating accumulates at the end of the microprojections in a "teardrop" shape. This teardrop shape can blunt the sharp end of the microneedle, potentially impacting the effectiveness and uniformity of penetration. Uneven layers of formulation on the microprojections results in uneven, and sometimes inadequate drug delivery. Additionally, the issues in the drying process cause issues of quality control in formulation coating. Preferred liquid coating formulations comprise zolmitriptan in an amount of 30% w/w to about 60% w/w, preferably about 40% w/w to about 50% w/w, more preferably about 45% w/w, and tartaric acid in an amount of about 5% w/w to about 25% w/w, preferably about 10% w/w to about 20% w/w, more preferably about 15% w/w, in a liquid carrier, preferably water, more preferably deionized water. With these liquid coating formulations, Applicant surprisingly found that maintaining a viscosity of about 150 cP to about 350 cP, preferably about 200 cP to about 300 cP, more preferably about 250 centipoise, and a surface tension of about 50 $mNm^{-1}$ to about 72 $mNm^{-1}$, preferably about 55 $mNm^{-1}$ to about 65 $mNm^{-1}$, more preferably about 62.5 $mNm^{-1}$ was required to avoid dripping. Teardrop formation could be avoided while simultaneously allowing each dip of microprojections into the liquid coating formulation to pick up sufficient volume of liquid coating formulation, thereby achieving the desired drug dose with a minimum number of dips. When the viscosity and surface tension of the coating solution are high enough, the coated liquid does not quickly drip back or form a teardrop shape after dipping and before drying.

The products and methods described herein with respect to delivery of zolmitriptan in a method of rapidly achieving therapeutic concentrations of zolmitriptan for treatment of migraine or cluster headache also can be applied to other triptans, including sumatriptan, rizatriptan, naratriptan, eletriptan, almotriptan, frovatriptan, avitriptan, and donitriptan.

In one aspect, the route of administration of zolmitriptan is intramuscularly, intracutaneously, subcutaneously, intranasally, oral inhalation, transdermally, buccally, pulmonary, or sublingually. For example, a formulation designed for intramuscular or subcutaneous delivery would contain 1 mg of zolmitriptan (base) and 0.3 mg of tartaric acid in 1 mL of 0.9% w/v saline. Further, a formulation designed for pulmonary delivery would be in the form of zolmitriptan salt dissolved or suspended in water or a zolmitriptan powder generated using milling, supercritical fluid process, spray drying or spray freeze drying for inhalation delivery and would produce respirable particles with a controlled particle size of about 0.5-5.8 μm mass median aerodynamic diameter (MMAD) to ensure that a significant fraction of zolmitriptan would be deposited in the lung. The processes to produce zolmitriptan powder can be used directly by metering in from a powder reservoir or premetering into a dry powder inhaler (DPI) format, or the particulates may be suspended/dispersed directly into a suspending media, such as a pharmaceutically acceptable propellant e.g., hydrofluoralkanes (selected from the group consisting of: 1,1,1,2-tetrafluoroethane, 1,1,1,2,3,3,3-heptafluoro-n-propane and a mixture of 1,1,1,2-tetrafluoroethane and 1,1,1,2,3,3,3-heptafluoro-n-propane or a mixture of thereof), in a metered dose inhaler (MDI) format. The particles produced may be crystalline or may be amorphous depending on the process to generate the zolmitriptan powder. In one aspect, the zolmitriptan dose ranges from 0.5 to 4 mg, administered at the onset of migraine or cluster headache.

V. Packaging, Sterilization

Improved physical stability of the dry coated formulations provides not only the benefit of an increased storage or shelf life for the therapeutic agent itself, but enhances efficacy in that once stabilized in accordance with the compositions of and methods for formulating and delivering of the present invention, the therapeutic agents become useful in a greater range of possible formulations, and with a greater variety of therapeutic agent delivery means.

The present disclosure comprises an active agent formulation wherein the deterioration by oxygen and/or water is minimized and/or controlled by the manufacture and/or packaging of the active agent formulation in a dry inert atmosphere. The formulation may be contained in a dry inert atmosphere in the presence of a desiccant, optionally in a chamber or package comprising a foil layer.

The desiccant can be any known to those skilled in the art. Some common desiccants include, but are not limited to molecular sieve, calcium oxide, clay desiccant, calcium sulfate, and silica gel. The desiccant may be one that can be placed with the biologically active agent-containing formulation in the presence of an inert atmosphere in a package comprising a foil layer.

In another aspect, the active agent formulation is packaged in a chamber comprising a foil layer after the formulation is coated onto the microprojection array delivery device. In this embodiment, a desiccant is contained in the chamber, preferably attached to a chamber lid which comprises a foil layer, and the chamber is purged with dry nitrogen or other inert gas such as a noble gas prior to the delivery device-containing foil chamber being sealed by the foil lid. Any suitable inert gas can be used herein to create the dry inert atmosphere.

In one embodiment, the compositions of and methods for formulating and delivering zolmitriptan suitable for intracutaneous delivery utilize a patch assembly. This patch assembly is manufactured and/or packaged in a dry inert atmosphere, and in the presence of a desiccant. In one embodiment, the patch assembly is manufactured in a dry inert atmosphere and/or packaged in a chamber comprising a foil layer and having a dry inert atmosphere and a desiccant. In one embodiment, the patch assembly is manufactured and/or packaged in a partial vacuum. In one embodiment, the patch assembly is manufactured and/or packaged in a dry inert atmosphere, and a partial vacuum. In one embodiment, patch assembly is manufactured in a dry inert atmosphere under a partial vacuum and/or packaged in a chamber comprising a foil layer and having a dry inert atmosphere, a partial vacuum, and a desiccant.

Generally, in the noted embodiments of the present invention, the inert atmosphere should have essentially zero water content. For example, nitrogen gas of essentially zero water content (dry nitrogen gas) can be prepared by electrically controlled boiling of liquid nitrogen. Purge systems can be also used to reduce moisture or oxygen content. A range for a partial vacuum is from about 0.01 to about 0.3 atmospheres.

In an aspect of this embodiment, the zolmitriptan further comprises a biocompatible carrier. In another embodiment, there is an intracutaneous delivery system, adapted to deliver zolmitriptan, comprising: (a) a microprojection member including a plurality of microprojections that are adapted to pierce the stratum corneum of a patient; (b) a hydrogel formulation comprised of zolmitriptan, wherein the hydrogel formulation is in communication with the microprojection member; and (c) packaging purged with an inert gas and adapted to control environmental conditions sealed around the microprojection member, wherein the sealed package has been exposed to radiation to sterilize the microprojection member.

In another embodiment, there is an intracutaneous delivery system, adapted to deliver zolmitriptan, comprising: (a) a microprojection member including a plurality of microprojections that are adapted to pierce the stratum corneum of a patient; (b) a solid film disposed proximate the microprojection member, wherein the solid film is made by casting a liquid formulation comprising zolmitriptan, a polymeric material, a plasticizing agent, a surfactant and a volatile solvent; and (c) packaging purged with an inert gas and adapted to control environmental conditions sealed around the microprojection member, wherein the sealed package has been exposed to radiation to sterilize the microprojection member.

The present disclosure is also to a method for terminally sterilizing a patch assembly adapted to deliver zolmitriptan, comprising the steps of: (a) providing a microprojection member having a plurality of microprojections that are adapted to pierce the stratum corneum of a patient having a biocompatible coating comprising zolmitriptan disposed on the microprojection member; and (b) exposing the microprojection member to radiation selected from the group consisting of gamma radiation and e-beam, wherein the radiation is sufficient to reach a desired sterility assurance level. Such sterility assurance level may be $10^{-6}$ or $10^{-5}$. The method may further comprise sealing the microprojection member with a desiccant inside packaging purged with an inert gas and exposing the packaged microprojection member to radiation selected from the group consisting of gamma radiation and e-beam radiation, wherein the radiation is sufficient to reach a desired sterility assurance level.

In an aspect of this embodiment, the method further comprises the step of mounting a patch comprised of a microprojection member attached to an adhesive backing on a pre-dried retainer ring to form a patch assembly, and subsequently sealing the microprojection member inside the packaging. In an aspect of this embodiment, the system further comprises a desiccant sealed inside the packaging with the patch assembly, and/or the packaging is purged with nitrogen, and/or the packaging comprises a pouch comprised of a foil layer. Preferably, the foil layer comprises aluminum.

The step of exposing the microprojection member to radiation may occur at approximately −78.5 to 25° C., or the member may be exposed to radiation at ambient temperature. The radiation may be in the range of approximately 5 to 50 kGy, or approximately 10 to 30 kGy, or approximately 15 to 25 kGy, or approximately 21 kGy, or approximately 7 kGy. In one aspect of this embodiment, the radiation is delivered to the microprojection member at a rate of at least approximately 3.0 kGy/hr.

As described herein, Applicant developed a zolmitriptan formulation which, when coated on the microneedle members of the present disclosure, is stable and maintains its amorphous character for at least 6 months, or at least 9 months, or at least 12 months, or at least 18 months, or at least 24 months after being exposed to radiation as described above.

In one embodiment, the dried zolmitriptan formulation on the microneedles retains for at least 6 months approximately 100% of initial purity, or approximately 99% of initial purity, or approximately 98% of initial purity, or approximately 97% of initial purity, or approximately 96% of initial purity, or approximately 95% of initial purity, or approximately 90% of initial purity. In other aspects, such purity is retained for at least 9 months, or at least 12 months, or at least 18 months, or at least 24 months after packaging. In a further embodiment, the zolmitriptan coating on the microneedles retains its purity as described in this paragraph, and also substantially maintains its amorphous character for at least 6 months, or at least 9 months or at least 12 months, or at least 18 months, or at least 24 months after packaging.

In one embodiment, a method for manufacturing a patch assembly for an intracutaneous delivery system adapted to deliver a zolmitriptan, comprises the steps of: providing a microneedle member having a plurality of microneedles that are adapted to penetrate or pierce the stratum corneum of a patient having a biocompatible coating disposed on the microneedle member, the coating being formed from a coating formulation having zolmitriptan and disposed thereon; sealing the microneedle member with a desiccant inside packaging purged with nitrogen and adapted to control environmental conditions surrounding the microneedle and exposing the microneedle member to radiation selected from the group consisting of gamma radiation, e-beam and x-ray wherein the radiation is sufficient to reach a desired sterility assurance level.

In accordance with another embodiment of the invention, a method for delivering stable biologically active agent formulations comprises the following steps: (i) providing a microprojection member having a plurality of microprojections, (ii) providing a stabilized formulation of biologically active agent; (iii) forming a biocompatible coating formulation that includes the formulation of stabilized biologically active agent, (iv) coating the microprojection member with the biocompatible coating formulation to form a biocompatible coating; (v) stabilizing the biocompatible coating by drying; and (vi) applying the coated microprojection member to the skin of a subject.

Additionally, optimal stability and shelf life of the agent is attained by a biocompatible coating that is solid and substantially dry. However, the kinetics of the coating dissolution and agent release can vary appreciably depending upon a number of factors. It will be appreciated that in addition to being storage stable, the biocompatible coating should permit desired release of the therapeutic agent.

Encompassed herein is a method for terminally sterilizing a transdermal device adapted to deliver a zolmitriptan, comprising the steps of: providing a microprojection member having a plurality of microprojections that are adapted to penetrate or pierce the stratum corneum of a patient having a biocompatible coating disposed on the microprojection member, the coating being formed from a coating formulation having at least one triptan, preferably zolmitriptan, disposed thereon; and exposing the microprojection member to radiation selected from the group consisting of gamma radiation and e-beam, wherein the radiation is sufficient to reach a desired sterility assurance level. A further aspect of this method comprises the further step of sealing the microprojection member inside packaging adapted to control environmental conditions surrounding the microprojection member. In one aspect the packaging comprises a foil pouch. A further aspect of this method, comprises the further step of sealing a desiccant inside the packaging. Further, the method comprises the step of mounting the microprojection member on a pre-dried retainer ring prior to sealing the microprojection member inside the packaging. A further aspect of this method comprises the step of purging the packaging with an inert gas prior to sealing the packaging. In one embodiment, the inert gas comprises nitrogen.

VI. In Vivo Pharmacokinetics (PK)

The intracutaneous/transdermal systems of the present invention provide serum concentrations to the bloodstream faster and with less overall drug exposure as compared to oral doses of the same drug. For example, the absorption of intracutaneously administered zolmitriptan delivered via the systems of the present disclosure results in a $C_{max}$ of less than 50 mg/mL and the $T_{max}$ is between about 2 minutes and 30 minutes. In another embodiment, the plasma zolmitriptan AUC for the first 2 hours is greater than that seen following oral administration, but the plasma zolmitriptan $AUC_{(0-24\ hr)}$ is less than that seen after oral administration.

In another aspect, the absorption of the zolmitriptan results in an increase in the maximum plasma zolmitriptan, but the N-desmethyl zolmitriptan production ($AUC_{0-24\ hr}$) is reduced and thus has a lower likelihood for metabolite accumulation. The intracutaneous administration of triptans, including zolmitriptan, avoids the first pass metabolism in the liver found with oral administration, resulting in higher bioavailability. In particular, metabolism is significantly reduced resulting in at least about 20% less serum concentration of N-desmethyl zolmitriptan at time points (e.g., 1.5 hours, 2 hours, 5 hours, 10 hours) post-application than seen in oral products. Further, zolmitriptan plasma levels may be increased, but the N-desmethyl zolmitriptan production is reduced relative to that produced upon oral administration of a comparable dose of zolmitriptan. Therefore, there is a lower likelihood for metabolite accumulation. However, because N-desmethyl zolmitriptan is more active at the target sites than zolmitriptan, the present invention is surprisingly effective at treating migraine or cluster headache as detailed below. In addition, the apparent half-life of zolmitriptan is reduced compared to oral administration, such that the duration of side effects may be reduced.

In another aspect, the plasma concentration of N-desmethyl zolmitriptan is about 0.05 to 0.9 ng/ml after about 15 minutes after application, or about 0.1 to 1.4 ng/ml after about 30 minutes, or about 0.1 to 1.6 ng/ml after about 1 hour, or about 0.1 to 1.4 ng/ml after about 1.5 hours, or about 0.1 to 1.3 ng/ml after about 2 hours, or less than about 0.7 ng/ml after 5 hours, or less than about 0.2 ng/ml after 10 hours.

Further, the intracutaneously delivered biocompatible coating comprises a dose of the zolmitriptan in the range of approximately 0.2 to 10 mg, preferably 1 to 5 mg, more preferably approximately 1.9 or 3.8 mg, wherein intracutaneous delivery of the zolmitriptan results in a plasma $C_{max}$ of at least 2 ng/mL zolmitriptan, at least 3.6 ng/mL zolmitriptan, at least 4 ng/mL zolmitriptan, at least 6 ng/mL zolmitriptan, at least 9 ng/mL zolmitriptan, at least 10 ng/mL zolmitriptan, at least 12 ng/mL zolmitriptan, at least 14 ng/mL zolmitriptan, at least 16 ng/mL zolmitriptan, at least 18 ng/mL zolmitriptan, at least 20 ng/mL zolmitriptan, at least 25 ng/mL zolmitriptan, at least 30 ng/mL zolmitriptan, at least 40 ng/mL zolmitriptan, at least 45 ng/mL zolmitriptan, at least 50 ng/mL zolmitriptan, less than 50 ng/mL zolmitriptan, at least 55 ng/mL zolmitriptan, at least 60 ng/mL zolmitriptan or at least 65 ng/mL zolmitriptan after one application or two applications.

Also, the intracutaneous delivery of the zolmitriptan results in a plasma $T_{max}$ of no more than 1 minute, no more than 2 minutes, no more than 3 minutes, no more than 4 minutes, no more than 5 minutes, no more than 8 minutes, no more than 10 minutes, no more than 12 minutes, no more than 15 minutes, no more than 20 minutes, no more than 30 minutes, no more than 35 minutes, no more than 40 minutes, no more than 45 minutes, no more than 50 minutes, no more than 55 minutes, is between 2 minutes and 30 minutes, or is no more than 60 minutes after one application.

In one embodiment, the $T_{max}$ of intracutaneously administered zolmitriptan via the inventive systems occurs about 2 hours or more before conventional release oral zolmitriptan tablets, or about 1.8 hours or more before such tablets, or about 1.6 hours or more before such tablets, or about 1.4 hours or more before such tablets, or about 1.2 hours or more before such tablets, or about 1.0 hours or more before such tablets, or about 0.8 hours or more before such tablets, or about 0.6 hours or more before such tablets, or about 0.4 hours or more before such tablets, or about 0.2 hours or more before such tablets.

In another embodiment, the $T_{max}$ of intracutaneously administered zolmitriptan via the inventive systems occurs about 3 hours or more before ZOMIG® (zolmitriptan) orally disintegrating tablets, or about 2.5 hours or more before such tablets, or about 2.0 hours or more before such tablets, or about 1.5 hours or more before such tablets, or about 1.0 hours or more before such tablets, or about 0.5 hour before such tablets.

In further embodiments, the $T_{max}$ of intracutaneously administered zolmitriptan via the inventive systems occurs about 3 hours or more before zolmitriptan nasal spray, or about 2.5 hours or more before such spray, or about 2.0 hours or more before such spray, or about 1.5 hours or more before such spray, or about 1.0 hour or more before such spray, or about 0.5 hour or more before such spray.

In another embodiment, the elimination rate ($t_{1/2}$) for intracutaneously administered zolmitriptan via the inventive systems is about 0.75 hour, or 1.0 hour, or 1.1 hour, or 1.2 hour, or 1.3 hour, or 1.4 hour, or 1.5 hour, or 1.6 hour, or 1.7 hour, or 1.8 hour, or 1.9 hour, or 2.0 hours. Such elimination rate ($t_{1/2}$) is approximately three times the rate of zolmitriptan conventional tablets, or approximately twice the rate of zolmitriptan conventional tablets.

In further embodiments, the $C_{max}$ for intracutaneously administered zolmitriptan via the inventive systems is about 1 to about 8 times higher than the $C_{max}$ of conventional oral 2.5 mg zolmitriptan tablets, or about 1.5 to about 7 times higher, or about 2 to about 6 times higher, or about 3 to about 5 times higher, or about 4 times higher.

Further, the mean peak exposure ($C_{max}$) is about 2 to about 5 times higher for intracutaneous zolmitriptan relative to the oral tablets. In a further aspect, the mean peak exposure ($C_{max}$) for the intracutaneous zolmitriptan of the present invention is about 1.0 to about 40.0 mg/mL, or about 5.0 to about 35.0 mg/mL, or about 10.0 to about 30.0 mg/mL, or about 15.0 to about 25.0 mg/mL, or about 20.0 to about 30.0 mg/mL, or about 25 mg/mL.

Additionally, compared to conventional oral zolmitriptan 2.5 mg, intracutaneous zolmitriptan of the invention at doses ranging from about 0.5 mg to about 4.0 mg have a bioavailability of about 50% to about 100% of the oral bioavailability. In other embodiments, the bioavailability of intracutaneous is about 55% to about 95%, or about 60% to about 90%, or about 65% to about 85%, or about 70% to about 80%, or about 75% of the oral bioavailability.

Finally, the present invention encompasses formulations and devices that are bioequivalent to the M207 Intracutaneous Delivery System described herein. Thus, the disclosure covers products where bioequivalence is established by (i) a 90% Confidence Interval (CI) for AUC which is between 0.80 and 1.25; and (ii) a 90% CI for $C_{max}$ which is between 0.80 and 1.25.

VII. Methods of Treatment

The drug-device combinations of the present invention can be used to treat a variety of diseases and conditions, including migraine and cluster headache. In one embodiment of the present invention, there is a method for treatment or alleviation of migraine or cluster headache to an individual in need thereof, comprising administration of a therapeutically effective amount of a zolmitriptan-based agent, wherein the absorption of the zolmitriptan-based agent results in a plasma $C_{max}$ of less than 50 ng/mL. Doses include about 0.2 mg to about 10 mg zolmitriptan. The dose may also be 0.48 mg, 0.96 mg, 1.9 mg, and 3.8 mg zolmitriptan. Doses also include a single patch administration of either 1.0 mg, 1.9 mg, or 3.8 mg, or two patches of 1.9 mg. These doses can be delivered utilizing the patch(es) described herein and can be applied to the skin of any part of the body. In a preferred embodiment, the zolmitriptan dose(s) is delivered via the patch to the upper arm to treat a single migraine or cluster headache attack.

In certain embodiments, the methods of treatment of migraine or cluster headache as described herein result in improvement with respect to the following therapeutic endpoints: Migraine Pain freedom at 1 hour, 2 hours, or 4 hours after dosing; Cluster headache pain freedom at 15 or 30 minutes after dosing, most bothersome other migraine symptom freedom at 1 hour or 2 hours after dosing; freedom from a patient's previously identified most bothersome other cluster headache symptom at 15 or 30 minutes after dosing, migraine pain relief at 1 hour, 2 hours or 4 hours; Cluster headache pain relief at 15 or 30 minutes after dosing, pain relief at 30 minutes; photophobia freedom at 2 hours; phonophobia freedom at 2 hours; pain relief at 15 minutes; pain relief at 3 hours; pain relief at 4 hours; nausea freedom at 2 hours; pain freedom at 30 minutes; pain freedom at 24 hours; and pain freedom at 48 hours. Further, there is an improvement in terms of treated patients requiring rescue medication. Improvement as to pain, most bothersome other symptom, photophobia, phonophobia, nausea, and other bothersome symptoms, is assessed sequentially, in a fixed-sequential testing method.

Tables 45-48 demonstrate effectiveness of the claimed invention for reducing or eliminating pain from migraine or cluster headaches, as compared to triptans and alternative forms of zolmitriptan. These results are based on one embodiment of the claimed invention, but are not so limited.

Figure 25:
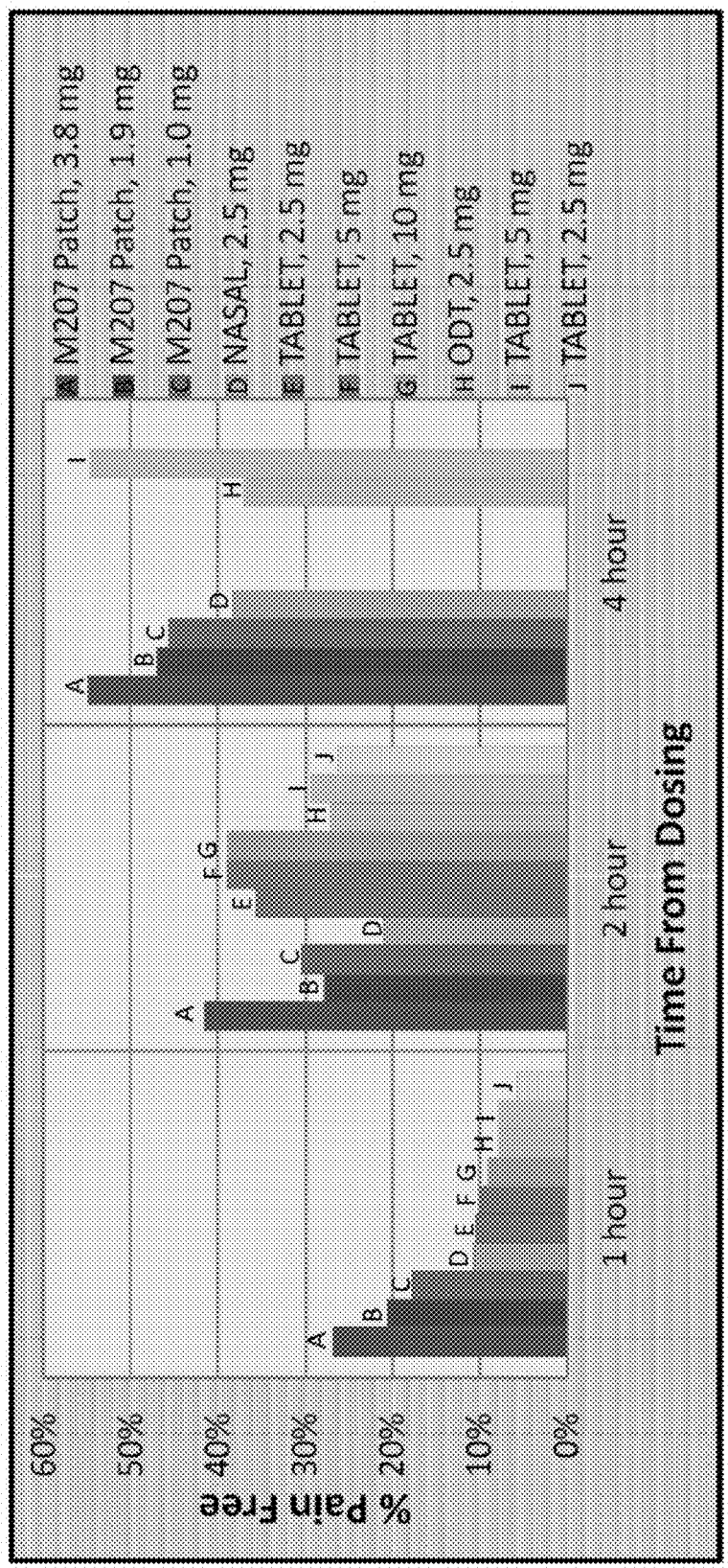
FIG. 25 is a graphical comparison of "% pain free" at 1, 2, and 4 hours after treatment.

Shown in Table 45, methods described herein demonstrate that the one embodiment of the claimed invention shows significant improvement in patients being pain free at 1 hour after dosing, as compared to a tablet of zolmitriptan. The results shown in Table 45 are merely one example of the significant efficacy that the claimed invention provides over the known methods for treating migraine or cluster headache with zolmitriptan. In one embodiment of the claimed invention, with a zolmitriptan dose of 1 mg, more than 15% of patients were pain free at 1 hour after treatment. In another embodiment (1.9 mg), more than 20% of patients were pain free at 1 hour. In a third embodiment (3.8 mg), more than 25% of patients were pain free at 1 hour. This shows improved efficacy over nasal treatment of zolmitriptan, with which it has been shown that only about 10% of patients are pain free at 1 hour. The current invention is also significantly more efficacious than 2.5 mg, 5 mg, and 10 mg tablets and 2.5 mg orally dissolving tablets, all of which only achieve pain freedom after 1 hour of 10% or less. The claimed invention also shows significant improvements in pain free results at 2 hours and 4 hours after treatment. In one embodiment, at 2 hours after treatment, more than thirty percent of patients were pain free. In another embodiment, at 2 hours, more than forty percent of patients were pain free. In a third embodiment, at 4 hours after treatment, more than fifty percent of patients were pain free. These are significant improvements over nasal treatments using zolmitriptan, in which less than twenty five and forty percent of patients are pain free after two and four hours from treatment, respectively. These results are also comparable to other zolmitriptan dosage forms and delivery routes, and at forty percent pain free at two hours better than all other zolmitriptan dosage forms and delivery routes. These results are also shown graphically in FIG. 25.

Figure 26:
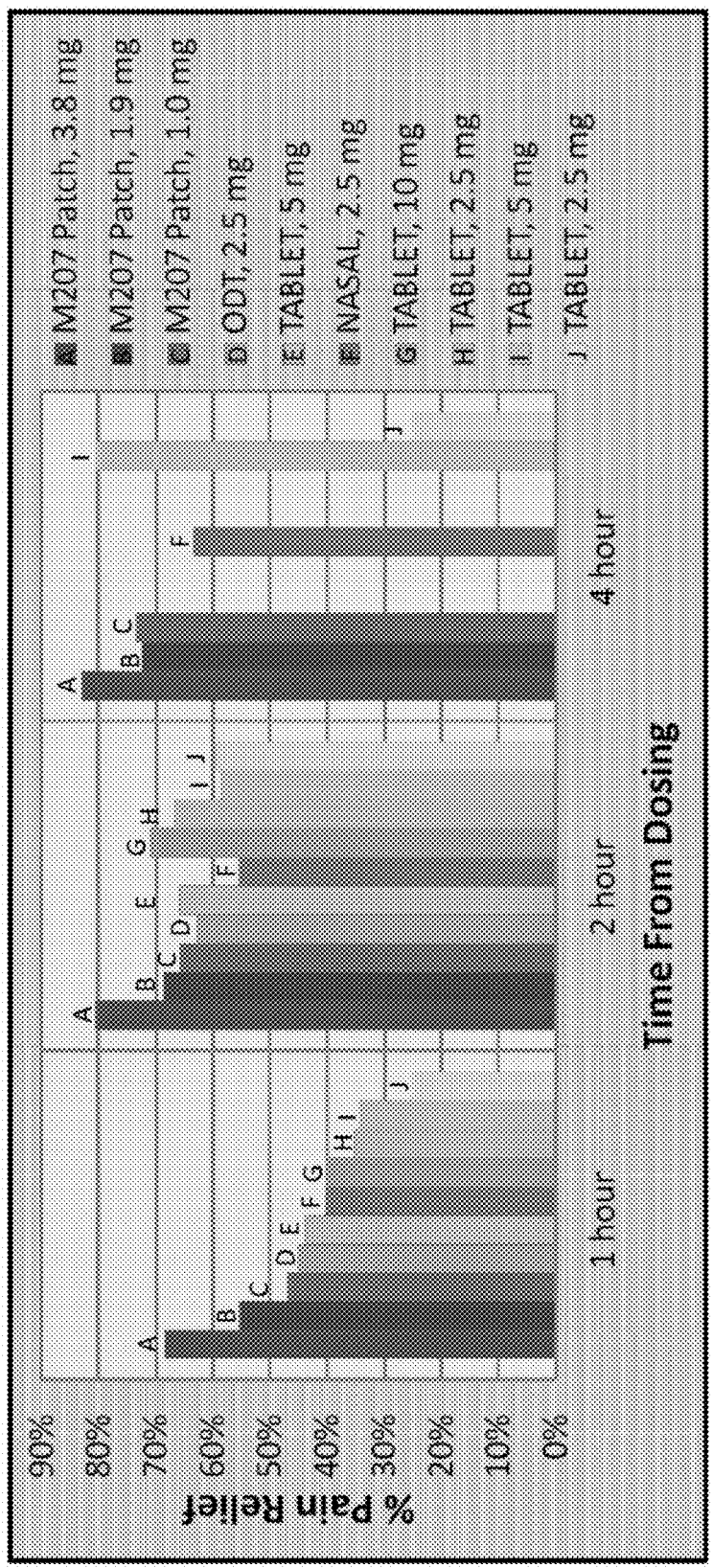
FIG. 26 is a graphical comparison of "% pain relief" at 1, 2, and 4 hours after treatment.

Table 46 provides a comparison of resulting pain relief between the claimed invention and the current methods for treating migraine or cluster headaches with zolmitriptan. In the 1 mg, 1.9 mg, and 3.8 mg embodiments, pain relief of over 45%, 55%, and 65% respectively was achieved at just one hour after dosing. More than 65%, 68%, and 80% respectively experienced pain relief at two hours after dosing. With the 3.8 mg embodiment, over 80% of patients experienced pain relief at four hours after dosing. All three embodiments demonstrated significant improvements in pain relief at 1 hour when compared to the other zolmitriptan dosage forms and delivery routes, and the 3.8 mg embodiment was also superior to the other zolmitriptan dosage forms at 2 and 4 hours. These results are also shown graphically in FIG. 26.

Figure 27:
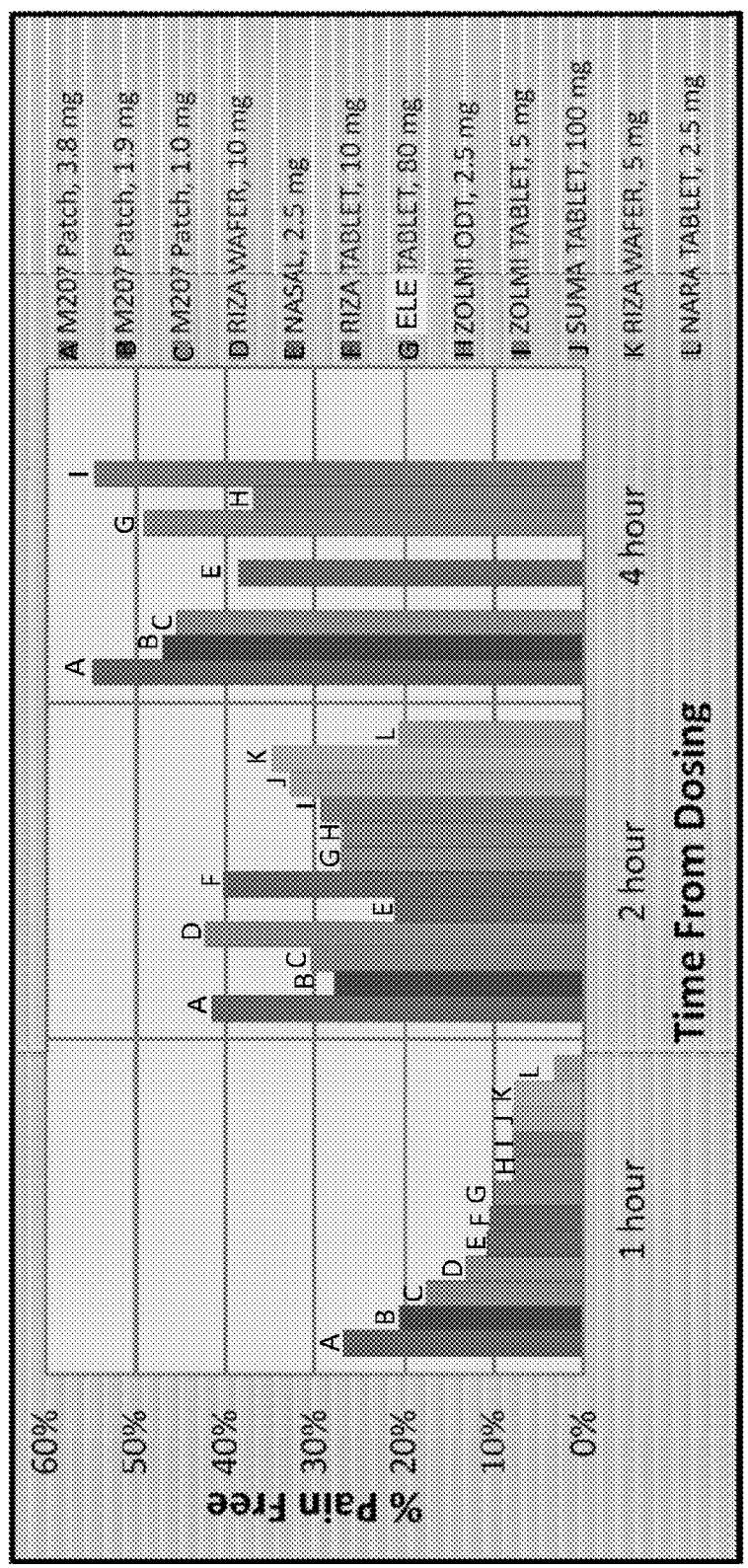
FIG. 27 is a graphical comparison of "% pain free" at 1, 2, and 4 hours after treatment.
Figure 28:
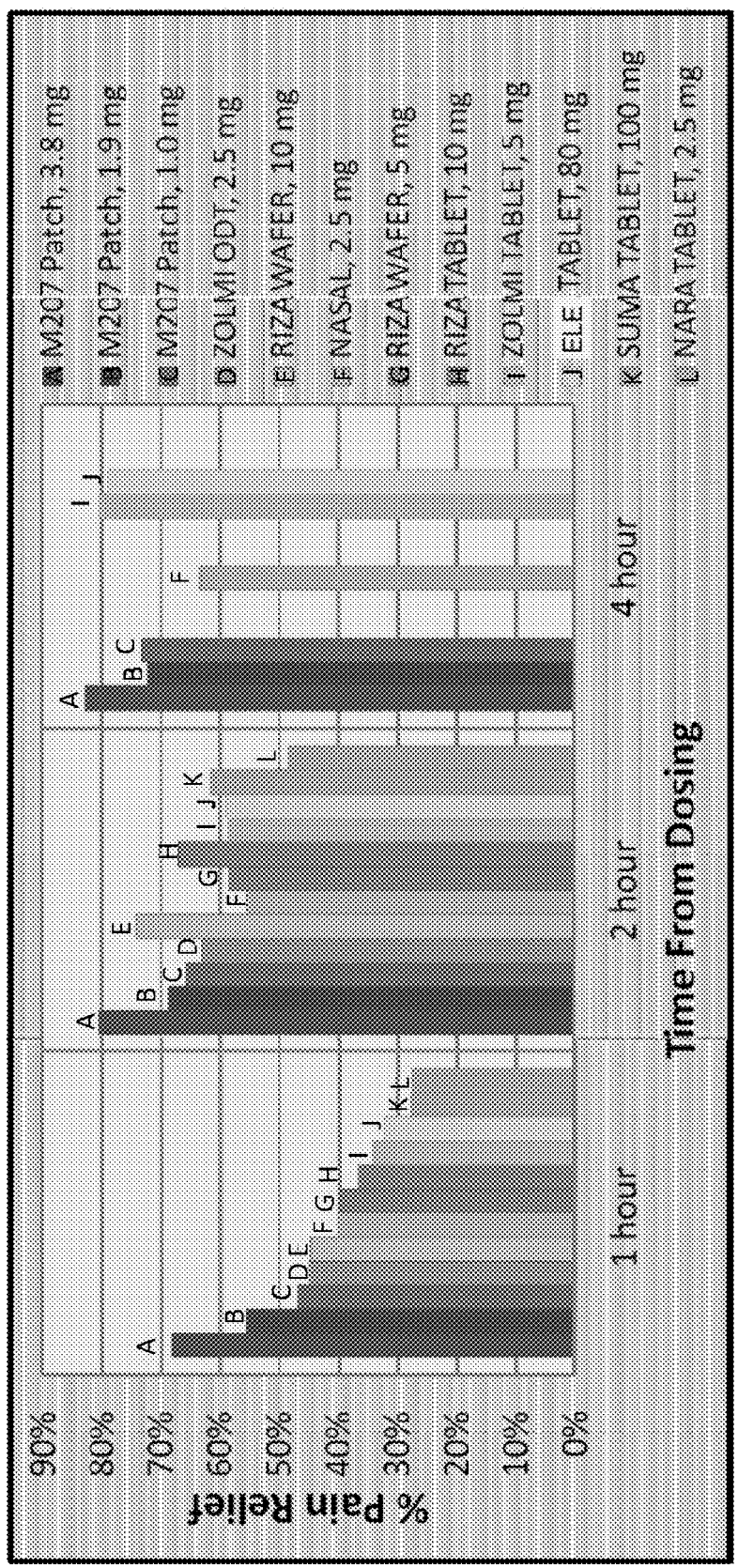
FIG. 28 is a graphical comparison of "% pain relief" at 1, 2, and 4 hours after treatment.
Figure 29:
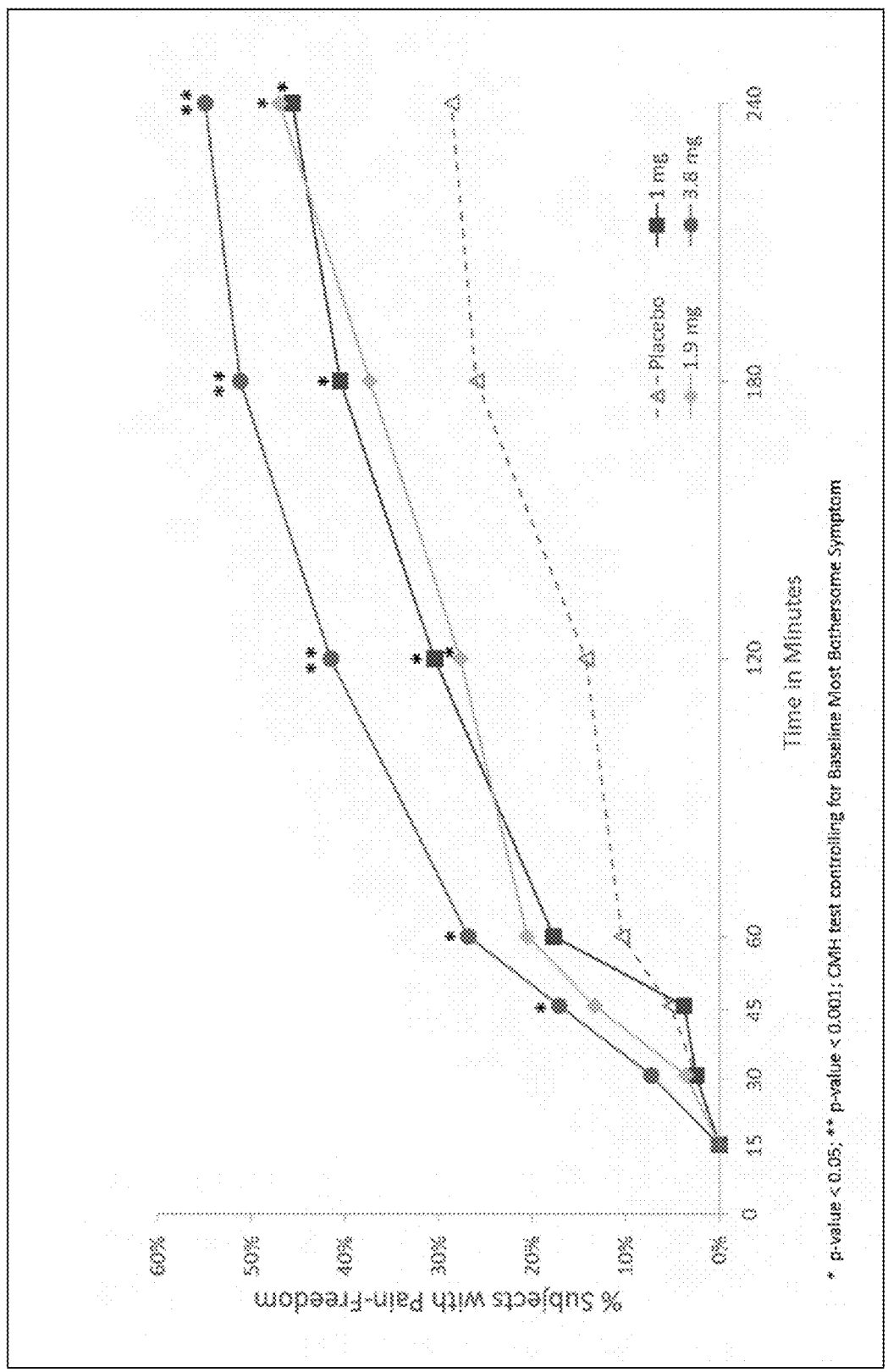
FIG. 29 is a graphical comparison of "% subjects with pain freedom" for up to 4 hours after treatment.

Tables 47 and 48 demonstrate the significant improvements of the claimed inventions over other triptans used for treating migraine or cluster headaches, for eliminating or reducing migraine or cluster headache pain. As shown in Table 47, the claimed invention shows significant improvements in pain free results over other triptans which are currently used in the art. At 17.7%, 20.5%, and 26.8% pain freedom at 1 hour for the 1 mg, 1.9 mg, and 3.8 mg embodiments respectively, all three strengths achieved higher levels of pain freedom than any of the other triptans. At 41.5 and 54.9% pain freedom at 2 and 4 hours, the 3.8 mg embodiment was still superior to all of the other triptans. These results are also shown graphically in FIG. 27. As shown in Table 48, the claimed invention shows significant improvements in pain relief results, over other triptans which are currently used in the art. At 46.8%, 55.4%, and 68.3% pain relief at 1 hour for the 1 mg, 1.9 mg, and 3.8 mg embodiments respectively, all three strengths achieved higher levels of pain relief than any of the other triptans. At 80.5% and 82.9% pain relief at 2 and 4 hours, the 3.8 mg embodiment was still superior to all of the other triptans. These results are also shown graphically in FIG. 28. In another aspect, the plasma $T_{max}$ of the administered zolmitriptan based agent is between about 2 minutes and 30 minutes. In one embodiment, administration of the zolmitriptan based agent is by transdermal or intracutaneous administration. Alternatively, the route of administration of a zolmitriptan based agent is intravenously, subcutaneously, orally, intranasally, oral inhalation, intracutaneously, transdermally, buccally, or sublingually.

In another embodiment, there is a method for treatment or alleviation of migraine or cluster headache in an individual in need thereof, comprising administering a therapeutically effective amount of a zolmitriptan based agent, wherein the plasma zolmitriptan AUC for the first 2 hours is greater than the plasma zolmitriptan AUC following oral administration of an equivalent dose of zolmitriptan, but the plasma zolmitriptan $AUC_{0-inf}$ following intracutaneous administration of a therapeutically effective amount of a zolmitriptan based agent is less than the plasma zolmitriptan $AUC_{0-inf}$ seen after the oral administration of an equivalent dose of zolmitriptan. In one aspect of this embodiment, administration of the zolmitriptan based agent is transdermal or intracutaneous administration. In one aspect of this embodiment, the route of administration of a zolmitriptan based agent is intravenously, subcutaneously, orally, intranasally, oral inhalation, intracutaneously, transdermally, buccally, or sublingually.

In another embodiment, there is a method for treatment or alleviation of migraine or cluster headache in an individual in need thereof, of a therapeutically effective amount of a zolmitriptan based agent, wherein, in comparison to oral administration of an equivalent dose of zolmitriptan, the zolmitriptan plasma levels are increased, but the N-desmethyl zolmitriptan production is reduced, thereby reducing the likelihood for metabolite accumulation. In one aspect of this embodiment, administration of the zolmitriptan based agent is transdermal or intracutaneous administration. In one aspect of this embodiment, the route of administration of a zolmitriptan based agent is intravenously, intramuscularly, intracutaneously, subcutaneously, orally, intranasally, oral inhalation, transdermally, buccally, or sublingually.

In another embodiment, there is a method for treatment or alleviation of migraine or cluster headache in an individual in need thereof, comprising the administration of a therapeutically effective amount of a zolmitriptan based agent, wherein, in comparison to oral administration of an equivalent dose of zolmitriptan, the apparent half-life of zolmitriptan is reduced, thereby indicating a likelihood of a reduced duration of side effects. In one aspect of this embodiment, administration of the zolmitriptan based agent is transdermal or intracutaneous administration. In one aspect of this embodiment, the route of administration of a zolmitriptan based agent is intravenously, intramuscularly, intracutaneously, subcutaneously, orally, intranasally, oral inhalation, transdermally, buccally, or sublingually.

In any of the embodiments disclosed herein, the route of administration of a zolmitriptan based agent is selected from the group consisting of intravenously, intramuscularly, intracutaneously, subcutaneously, orally, intranasally, oral inhalation, transdermally, buccally, and sublingually.

In an aspect of this embodiment, the intracutaneously administered zolmitriptan based agent provides a pharmacokinetic profile similar to the pharmacokinetic profile provided by subcutaneous administration of an equivalent dose to the intracutaneously administered sumatriptan based agent.

In one aspect of the method where the zolmitriptan is administered, the administration of the zolmitriptan is not associated with effects on blood pressure greater than those seen with oral zolmitriptan, despite faster absorption.

In one embodiment, there is a method for treatment or alleviation of migraine or cluster headache in an individual in need thereof, comprising administration of a therapeutically effective amount of a zolmitriptan based agent, wherein the time to achieve maximum plasma concentration ($T_{max}$) was comparable to or less than the $T_{max}$ of an equivalent oral dose of zolmitriptan. In one aspect of this embodiment, administration of the zolmitriptan based agent is transdermal or intracutaneous administration. In one aspect of this embodiment, the route of administration of a zolmitriptan based agent is intravenously, subcutaneously, orally, intranasally, oral inhalation, intracutaneously, transdermally, buccally, or sublingually. In one aspect of these embodiments, the generation of N-desmethyl zolmitriptan is reduced relative to the generation of N-desmethyl zolmitriptan resulting from an oral dose of an equivalent amount of the zolmitriptan based agent. In another aspect of these embodiments, the absorption of the intracutaneously administered zolmitriptan based agent results in a $C_{max}$ of less than 50 ng/mL.

VIII. Examples

The following examples are included to demonstrate certain embodiments of the invention. Those of skill in the art should, however, in light of the present disclosure, appreciate that modifications can be made in the specific embodiments that are disclosed and still obtain a like or similar result without departing from the spirit and scope of the invention. Therefore all matter set forth is to be interpreted as illustrative and not in a limiting sense.

In the examples below, unless stated otherwise, the microprojection arrays were fabricated by a photo/chemical etching and formed using a controlled manufacturing process. The method is substantially similar to that described in M. Cormier et al., "Device for enhancing transdermal agent delivery or sampling," EP0914178B1, incorporated herein by reference in its entirety. Drug formulation coating on the microprojection array was conducted at ambient temperature utilizing a roller drum, rotating at 50 rpm, in a drug formulation reservoir (2 mL in volume) to produce a drug coating formulation film of controlled thickness. The method is substantially similar to that described in J. C. Trautman et al., "Method and apparatus for coating skin piercing microprojections," U.S. Pat. No. 6,855,372; J. C. Trautman et al., "Method and apparatus for coating skin piercing microprojections," U.S. Pat. No. 7,435,299, incorporated herein by reference in their entirety. Microprojections are dipped into the film. The amount of coating is controlled by the number of dips (passes) through the drug film as well as the drug coating formulation properties. The time between each dip was a few seconds which was sufficient to dry the coated liquid formulation under ambient conditions. The reservoir was circulated with coolant to maintain a film temperature of 1° C. Since the reservoir is open to the ambient air, the coating apparatus was positioned inside a dew-point control system. Dew point control minimizes moisture condensation into or evaporation from the liquid formulation during coating. The zolmitriptan-coated microneedle arrays were assembled with adhesive backing to form a patch, and mounted on a retainer ring to form a patch assembly. The patch assembly was packaged in an aluminum pouch (Mangar, New Britain, Pa., USA), purged with dry nitrogen and heat-sealed with a Multivac heat sealer (model C400) (Multivac, Kansas City, Mo., USA).

Example 1—Zolmitriptan Coating Formulations, Characterization, Physical Properties Zolmitriptan is a weak base with a pKa of 9.6. Solubility measurements were conducted by adding excess zolmitriptan base to 0.5 ml of 0.1 M acid and rotating the suspension overnight at 2-8° C. The suspension was then centrifuged. The supernatant was then collected and subsequently the concentration of zolmitriptan dissolved was determined. Table 2 presents the solubility results of zolmitriptan in the various acids.

TABLE 2

Solubility of Zolmitriptan in Various Acids at 2-8° C.

| Aqueous Solvent | Solubility (mg/mL) |
| --- | --- |
| Citric acid | 88.6 |
| Tartaric acid | 63.3 |
| Maleic acid | 50.5 |
| Succinic acid | 59.1 |

TABLE 2-continued

Solubility of Zolmitriptan in Various Acids at 2-8° C.

| Aqueous Solvent | Solubility (mg/mL) |
|---|---|
| HCl | 33.3 |
| De-ionized water | 1.3 |

Zolmitriptan exhibits good solubility in the various acids. It was noted that the rheological behavior of the zolmitriptan solution was affected by the counterion in the formulation for pH control. Several weak acid buffers, including one triacid (citric acid), two diacids (maleic acid and tartaric acid) were tested. The zolmitriptan formulations that were prepared with citric, maleic and tartaric acids were at pH 5.2, 4.3 and 6.2 respectively, at the pKa of the acids. The viscosity profiles of formulations including these acids were measured as a function of time. Citric and maleic acid buffered formulations exhibited rheopectic behavior, i.e., an increase in viscosity as a function of time, while formulations buffered by tartaric acid maintained relatively uniform viscosity with time. Given the overall rheological effect, tartaric acid was selected as the counterion for pH adjustment.

A liquid coating formulation of 33% w/w zolmitriptan, 11% w/w tartaric acid and 56% w/w de-ionized water formulation was prepared at pH 4.5 and contact angle on titanium substrate was determined to be 65.8 degrees indicative of poorly wettable formulation. To improve wettability of formulation on titanium, polysorbate 20 at concentration of 0.2% w/w was added to the zolmitriptan formulation. Contact angle decreased to 51.6 degrees.

Static contact angle of drug solution formulations on titanium surface was determined using a FDS contact angle meter (Model OCA15) employing an optical contact angle method called "Sessile drop". For static contact angle measurement, a photo snapshot is taken once a drop of the solution (5 µL) is dispensed from the syringe and laid on a clean titanium foil surface. The angle between the baseline of the drop and the tangent at the drop boundary is measured on both sides. Complete measurement was obtained by averaging the two numbers. At least five readings were recorded for each sample.

Coating trials with 33% w/w zolmitriptan, 11% w/w tartaric acid, 0.2% w/w polysorbate 20, qs ad deionized water were conducted. Drug formulation coating on the microprojection array was conducted at ambient temperature utilizing a roller drum, rotating at 50 rpm, in a drug formulation reservoir (2 mL in volume) to produce a drug formulation film of controlled thickness. Microprojections were dipped into the drug film. The amount of coating was controlled by the number of dips (passes) through the drug coating formulation film. The time between each dip was only a few seconds which was sufficient to dry the coated liquid formulation under the ambient conditions. Since the reservoir was open to the ambient air, the coating apparatus was positioned inside a dew-point control system. The process is designed to match the drug film temperature to the air dew point, which prevents evaporation of the coating formulation over the duration of the manufacturing run. However, undulations in the zolmitriptan liquid formulation were noted visually, which is symptomatic of an uneven film. Concentration of zolmitriptan in the liquid formulation was increased up to 51% w/w (tartaric acid in the formulation was 17% w/w and 0.2% w/w polysorbate 20). Undulations in film were still noted with the higher solids content formulations. Subsequently, the polysorbate 20 was removed, and it was noted that the undulations were no longer present. This is a surprising and non-obvious result, because conventional teachings in pharmaceutics supported the use of surfactants to facilitate the production of a smooth, uniform coating.

In another coating embodiment, a 33% w/w zolmitriptan, 11% w/w tartaric acid and 56% w/w deionized water formulation caused high incidence of wicking on the particular microprojection array utilized, whereby the drug did not adhere to the microprojections. Although the viscosity of the formulation was 22 cP, the design of the microprojection (width of 120 µm, length 340 µm) and the thick drug film (calculated film thickness 270 µm) are such that, in each dip into the drug film the microprojections would pick a volume of liquid that cannot be dried fast enough, which leads to the drug film spreading onto the base of the microprojections. A higher solids content formulation 40% w/w zolmitriptan, 13.3% w/w tartaric acid and 46.7% w/w de-ionized water (M207), with a viscosity of 85 cP coated the microprojections uniformly and no wicking was noted. This formulation was utilized for further evaluation. Representative batch formulas are provided in Tables 3 and 4 for two strengths of microneedle array patches (internal product name M207), based on the nominal batch size of 45 g (zolmitriptan base).

TABLE 3

Batch Formula for M207 1 mg

| Component | Quantity (mg/patch) | Quantity (g/batch) |
|---|---|---|
| Zolmitriptan | 1 | 45 |
| Tartaric Acid | 0.3 | 15 |

TABLE 4

Batch Formula for M207 1.9 mg

| Component | Quantity (mg/patch) | Quantity (g/batch) |
|---|---|---|
| Zolmitriptan | 1.9 | 45 |
| Tartaric Acid | 0.6 | 15 |

Viscoelastic Properties

The 40% w/w zolmitriptan liquid formulation was evaluated for viscoelastic properties. Viscoelastic characterization of a fluid can be a useful tool for predicting the fluid's gelation tendency. H. A. Barnes, J. F. Hutton, and K. Walters, An Introduction to Rheology (Elsevier, New York, 1989). Measurement of viscoelasticity (i.e., elastic and viscous components) in a viscometer is based on a complex, theoretical model. Briefly subjecting the material to an oscillatory stress or strain, whose value is small enough not to destroy the material's structure, produces the output of phase angle. The phase angle is the ratio between the viscous modulus and the elastic modulus. A phase angle of 0 degrees corresponds to a fully elastic material, following Hooke's law of elasticity, hence suggesting a more rigid, and ordered structure. A phase angle of 90 degrees corresponds to a material with fully viscous behavior, indicating a less ordered structure which is less prone to gelation. The 40% w/w zolmitriptan liquid formulation exhibited high phase angle around 83 degrees indicating that the formulation is not susceptible to gelation.

Characterization of Mechanical Properties of ZP-Zolmitriptan Patches by Nanoindentation Mechanical properties of zolmitriptan coating such as hardness and toughness were evaluated by nanoindentation for M207 1.9 mg patches. Nanoindentation testing was performed on individual microprojections coated with zolmitriptan after the microprojections were broken off at the base of the titanium array. For hardness measurements, the coated microprojections were sampled from the center and two edge locations of the array and 10 indentation measurements were made for each of the three locations. Hardness and reduced elastic modulus were determined using a Berkovich indenter by a Nanomechanical Test System, TriboIndenter. Toughness was determined by fracture toughness using TriboIndenter with a cube corner indenter. Five indents were made for each patch sample.

TABLE 5

Nanoindentation results for gamma-irradiated M207 1.9 mg (L/N0203154-gamma)

| Stability Condition | avg H (MPa) | avg H S.D. (MPa) | avg $E_r$ (GPa) | avg $E_r$ S.D. (GPa) | $K_c$ (kPa * $m^{1/2}$) | $K_c$ S.D. (kPa * $m^{1/2}$) |
|---|---|---|---|---|---|---|
| T0 | 380.89 | 29.27 | 8.20 | 0.33 | 157.02 | 17.87 |
| T3M-25° C./60% RH | 357.85 | 6.27 | 8.19 | 0.33 | 135.76 | 2.94 |
| T3M-40° C./75% RH | 329.34 | 42.84 | 7.80 | 0.47 | 126.64 | 3.08 |
| T6M-25° C./60% RH | 279.89 | 8.70 | 9.09 | 0.89 | 117.67 | 12.03 |
| T12M-25° C./60% RH | 283.61 | 4.01 | 7.15 | 0.05 | 164.96 | 9.20 |

Dynamic Vapor Sorption

Water sorption and desorption isotherms of M207 1.9 mg patches were determined at 25° C. by DVS Intrinsic (Surface Measurement Systems, Ltd.). Each patch was exposed to a cycle of controlled relative humidity (RH) at incremental steps ascending from 0% to 65% and subsequently descending from 65% to 0%. The change in weight was continually measured by a microbalance with a 0.1 µg resolution. At each RH step the sample was allowed to reach equilibrium with dm/dt criterion of 0.0004 before moving to the next RH step. An uncoated patch was analyzed under the same conditions to determine background water uptake by the patch components other than the coated drug formulation.

Crystallinity

X-Ray diffraction (XRD) analysis was performed to characterize the solid state phases of dried zolmitriptan coating on patch for the M207 1.9 mg system. Non-irradiated and gamma-irradiated M207 patches were analyzed and compared to an uncoated patch of the same array design. For each patch sample to be analyzed, approximately 45-50 microprojections with zolmitriptan coating were broken off at the base of the titanium array and analyzed as bulk by XRD. XRD data was collected by a coupled Theta: 2-Theta scan on a Bruker D8 Vantec diffractometer equipped with a micro-focus copper x-ray tube with Montel optics monochromator, 0.5 mm collimator, a Vantec 500 2-D area detector and laser alignment system. XRD pattern of zolmitriptan coated microprojections were compared to that of uncoated microprojections. All the sharp peaks present in zolmitriptan coated patch samples were matched with those in the uncoated patch sample. Those sharp peaks were identified as titanium (Ti) metal based on the reference XRD data from ICDD/ICSD database, indicating the crystalline phase result from the Ti microprojection substrate. Zolmitriptan coated patches showed a broad, wide peak centered at about 18° 2-Theta, which is absent in the uncoated patch sample, indicating the drug coating is amorphous material for both non-irradiated and gamma-irradiated patches. Percent crystallinity was calculated with peak profile fitting, the results are summarized in Table 6, and was monitored on stability as described below.

TABLE 6

Phase Identification and Percent Crystallinity for M207 Patch Samples

| Sample | Phases Present | % Crystallinity |
|---|---|---|
| Non-irradiated M207 (LN 0203154-NI) | Ti•Titanium Hexagonal, S.G: P63/mmc (194) Phase Info | 100% (Ti) 0% drug coating |
| Gamma-irradiated M207 (LN 0203154-Gamma) | [01-089-3725] Amorphous material Ti•Titanium Hexagonal, S.G: P63/mmc (194) Phase Info [01-089-3725] Amorphous material | 100% (Ti) 0% drug coating |
| Uncoated Patch (Array Design: MF1663) | Ti•Titanium Hexagonal, S.G: P63/mmc (194) Phase Info [01-089-3725] | 100% (Ti) |

Mechanical properties of zolmitriptan coating were evaluated as function of time and storage condition. Mechanical properties such as hardness, which is a measure of a material's resistance to localized plastic deformation, elastic modulus a measure of material's resistance to being deformed elastically when a force is applied to it (measure of material's stiffness) and fracture toughness, which describes the ability of a material containing a crack to resist fracture, were evaluated. Multiple coated microprojections from different areas of individual ZP-Zolmitriptan patches were sampled for testing. Table 5 summarizes the results of nanohardness (H), reduced modulus elastic modulus ($E_r$), and fracture toughness ($K_c$) for gamma irradiated M207 1.9 mg patches stored at 25° C./60% RH for up to 12 months and at 40° C./75% RH for up to 3 months. The stability results suggest a decreasing trend in hardness and fracture toughness, and an increasing trend in the elastic modulus.

Zolmitriptan Purity and Content Quantitation

Purity of zolmitriptan was determined by the reverse phase high performance liquid chromatography (RPHPLC)

method (TM-601) at wavelength of 225 nm. Chromatography for the assay was performed using a Phenomenex Kinetex EVO C18, (4.6 mm ID×150 mm, 5 μm) maintained at 30° C. The mobile phase involved a gradient elution, with solvent A: Ammonium Dihydrogen Phosphate buffer:MeOH:Acetonitrile, 70:20:10 (v/v), and solvent B: Ammonium Dihydrogen Phosphate buffer:Acetonitrile, 30:70 (v/v), and was pumped at the flow rate of 0.6 mL/min on an HPLC system (Water Alliance 2695) equipped with a binary pump, a thermostatted autosampler, column compartment, and a PDA detector. Data were collected and analyzed using Empower Pro (Empower 2 software, Waters Corporation).

In Vitro Dissolution

In vitro dissolution of M207 1.9 mg patches were evaluated using standard USP Paddle over Disk apparatus (USP apparatus 5) with Distek 2100C 6-position dissolution tester. The paddle height was set at 25 mm above patch and rotated at 50 RPM. An USP vessel was filled with degassed 500 mL PBS dissolution medium and the temperature was controlled at 32° C. A full patch assembly containing the coated patch adhered to the center of an inner ring and then attached to an outer ring was inserted along the vessel wall into the vessel with the coated microprojections facing upright. The release of zolmitriptan from the coated patch was continually monitored via quantitation of zolmitriptan concentration of the dissolution medium by UV absorbance using Pion Rainbow 6-Ch Fiber Optic System with 14 cm dip probe and 10 mm pathlength.

M207 patches stored at room temperature and at 40° C./75% relative humidity for 10 months were evaluated. The results illustrated in FIGS. 6(A)-(C) and Table 7 show instantaneous release of zolmitriptan for all the patches tested with a steep slope reaching concentration plateau of complete dissolution in less than one minute.

TABLE 7

Concentration-Time of Dissolution of Zolmitriptan

| | Time (s) | Percent Dissolution (% D) |
|---|---|---|
| E-beam irradiated and stored at RT for 10 months | 0 | 0 |
| | 20 | 60-80 |
| | 40 | 90-100 |
| | 60 | 100 |
| | 80 | 100 |
| | 100 | 100 |
| Non-irradiated and stored at 40° C./75% RH for 10 months | 0 | 0 |
| | 20 | 0 |
| | 40 | 10-40 |
| | 60 | 90-100 |
| | 80 | 100 |
| | 100 | 100 |
| E-beam irradiated and stored at 40° C./75% RH for 10 months | 0 | 0 |
| | 20 | 5-10 |
| | 40 | 10-50 |
| | 60 | 50-100 |
| | 80 | 100 |
| | 100 | 100 |

Example 2—Ex Vivo Human Skin

The in vitro, Franz, human skin finite dose model is a tool for the study of percutaneous absorption of topically applied drugs. The model uses ex vivo, human torso skin mounted in specially designed diffusion cells allowing the skin to be maintained at a temperature and humidity that match typical in vivo conditions. A finite dose (for example, 2 mg/cm$^2$-10 mg/cm$^2$ of a semisolid, or a transdermal delivery system) of formulation is applied to the outer surface of the skin and drug absorption is measured by monitoring its rate of appearance in the receptor solution bathing the inner surface of the skin. Data defining total absorption, rate of absorption, as well as skin content can be determined in this model.

Dosing. The zolmitriptan patches were applied to the ex-vivo skin with use of an applicator. Following dosing, the patch and the skin were immediately mounted onto a Franz Diffusion Cell.

Dermal Receptor Medium. Normal phosphate buffered saline (pH 7.4±0.1) with 0.008% gentamicin sulfate (PBSg) solution was utilized when the diffusion cells were first mounted.

Diffusion Cell and Skin Preparation. Percutaneous absorption was measured using the in vitro, human skin, Franz finite dose technique. Ex vivo, dermatomed, human torso skin, without obvious signs of skin disease or damage was used in this study. The skin was provided to the testing facility as dermatomed, cryopreserved, and sealed in a water-impermeable bag with continuous storage at ~−70° C. Prior to use, it was thawed in ~37° C. water and then rinsed in distilled, de-ionized water (ddH2O) to remove any adherent blood or other material from the surface.

Skin from each donor was cut into multiple smaller sections large enough to fit on nominal 7 cm2 static Franz diffusion cells. The actual thickness of each skin section was measured in triplicate using a Digital Pocket Thickness Gauge (results in Table 2). Each skin section was then mounted onto a diffusion cell.

The dermal receptor compartment was filled to capacity with PBSg. The epidermal chamber (also known as the chimney or donor compartment) was left un-occluded with exposure to the ambient laboratory environment. The cells were then placed within a rack system and attached to a water circulation system from which the receptor solution was stirred magnetically at approximately 600 RPM, and its temperature was maintained to achieve a skin surface temperature of 32±1° C. (data on file). Skin was left to equilibrate for a minimum of 1 hour prior to the barrier integrity test.

One additional skin section per donor was prepared and underwent all study activities, but dosed with a placebo patch, to serve as a negative sample control.

Barrier Integrity Test. To ensure the barrier integrity of each skin section, its desorption of water was measured for trans-epidermal water loss (TEWL). A Delfin Vapometer probe was activated, placed onto the skin surface, and the TEWL value recorded. Skin mounted in diffusion cells in which TEWL was less than 25 g/m2/h were considered acceptable. Skin sections that were determined to be unacceptable for dosing may have been used as non-dosed negative sample control cells, if needed. After the barrier integrity test was complete, the receptor solution was replaced with the designated stock receptor solution of 0.1×PBSg.

Donor Demographics. The demographics of the skin donors are summarized in table 8.

TABLE 8

Donor Demographics

| Donor ID | Age | Race | Sex | Skin Thickness (mm) | Integrity Test (g/m$^2$/h) |
|---|---|---|---|---|---|
| NS021715 | 51 | Black | Male | 0.40 ± 0.08 | 8.78 ± 0.66 |
| SM081016 | 50 | Caucasian | Male | 0.49 ± 0.16 | 8.18 ± 2.63 |
| SG100316 | 50 | Black | Female | 0.50 ± 0.21 | 8.80 ± 0.29 |

Dose Administration and Sample Collection. Prior to administration of the patches to the skin sections, a pre-dose (0 hour) sample was collected as the entirety of the receptor solution volume was withdrawn with an approximate 5 mL aliquot of the collected sample saved for subsequent analysis. The receptor solution was replaced with the designated stock receptor solution of 0.1×PBSg. The chimney was then temporarily removed from the Franz diffusion cell to allow full access to the epidermal surface of the skin.

Immediately following patch application, the skin-patch combination and the donor compartment (chimney) were replaced onto the receptor compartment of the Franz diffusion cell.

At the scheduled sampling time points (3, 5, 10, 15, 30, 45, 60, 90, 120, 150, 180, 210, 240, 270, and 300 minutes), the receptor solution was removed in its entirety, refilled with stock receptor solution, and an approximate 5 mL aliquot of the collected sample was saved for subsequent analysis. For sample analysis, a 5 mL aliquot was lyophilized using vacuum centrifugation and reconstituted in 0.25 mL of ddH2O.

After the last receptor sample was collected, the patch was removed for subsequent extraction and analysis. The skin surface wash was performed using two successive refluxing washes of ddH2O. Each wash cycle consisted of at least 10 refluxes. The two wash volumes from each donor cell were pooled to generate a single surface wash sample for the diffusion cell.

Following the surface wash, the skin was allowed to dry for no less than 10 minutes. Subsequently, the skin was tape stripped with up to ten (10) sequential tapes (e.g. 3M Transpore® tape) to remove and collect the stratum corneum. Tape strips were extracted overnight in ddH2O. The skin was then dismounted from the cell and separated by manual dissection into epidermis and dermis for subsequent extraction and analysis. Skin sections were extracted overnight in ddH2O.

Sample Analysis. Quantification of zolmitriptan in the collected samples was accomplished using a validated HPLC method.

Samples were analyzed on a Shimadzu Series LC System. The HPLC UV/Vis method used a solvent system consisting of a mobile phase gradient using (Solvent A) 0.1% ammonium acetate with 0.1% acetic acid in H2O and (Solvent B) methanol and was run through a Phenomenex Luna C18(2) column, (100×4.6 mm, 3μ) at a flow rate of 0.5 mL/min for the analysis of zolmitriptan. The column was maintained at 40° C.

Figure 30:
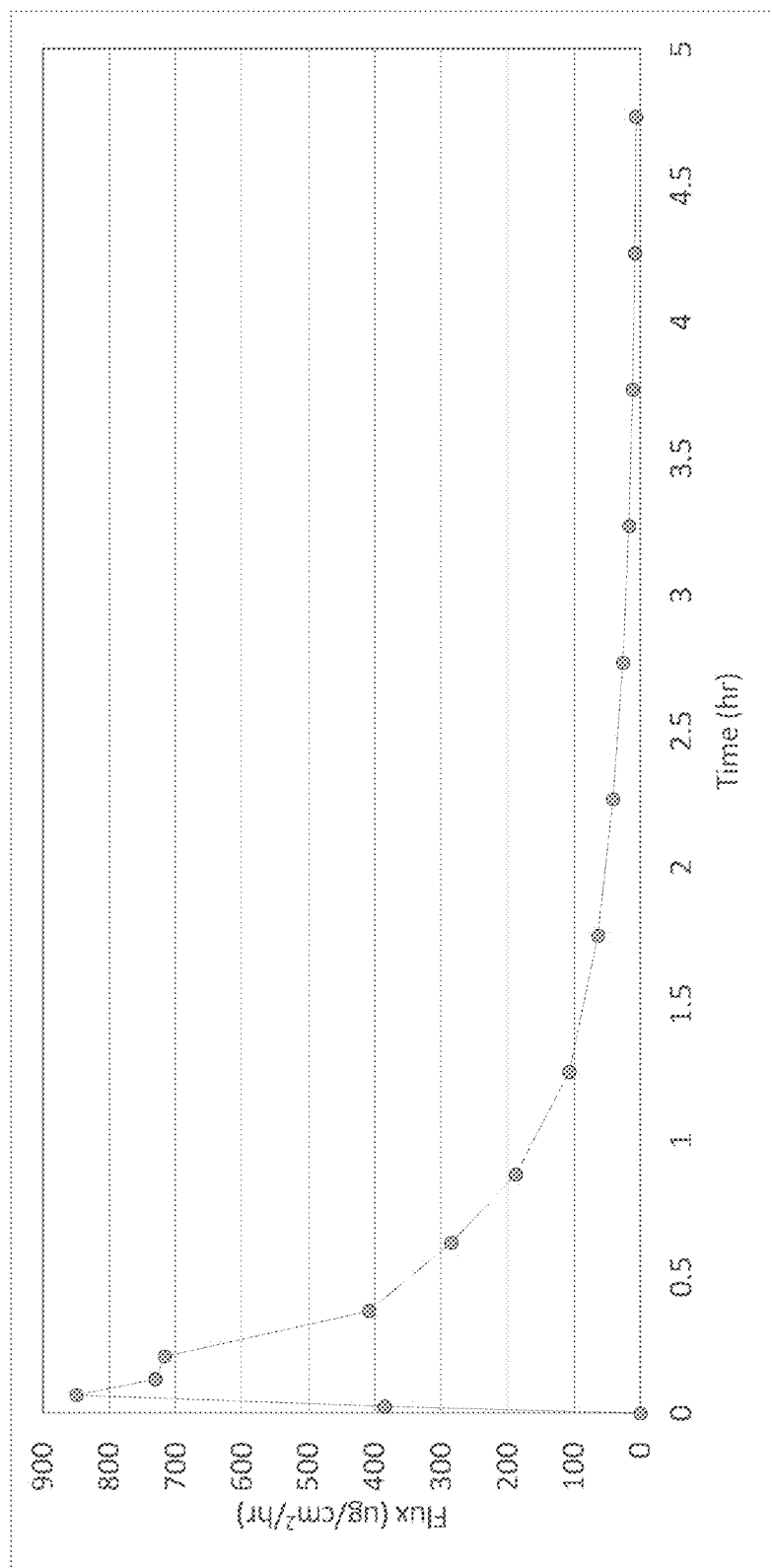
FIG. 30 is a graphical representation of the mean flux results from ex vivo human skin samples.

Mean Flux Results. Percutaneous absorption of zolmitriptan through ex vivo human torso skin over 300 minutes from a single application (Mean±SE). The mean flux ($\mu g/cm^2/hr$) is summarized in table 9 and in coordinating FIG. 30. This is an across donor summary, showing results of percutaneous absorption of zolmitriptan through ex vivo human torso skin over 300 minutes from a single application (Mean, N=3 donors).

TABLE 9

Mean Flux ($\mu g/cm^2/hr$) Results: Across Donor Summary

| Time (hr)* | ZP-Zolmitriptan 1.9 mg |
|---|---|
| 0.025 | 385.3 ± 95.9 |
| 0.067 | 849.4 ± 42.1 |
| 0.125 | 730.5 ± 41.7 |
| 0.208 | 716.5 ± 46.7 |
| 0.375 | 408.9 ± 26.1 |

TABLE 9-continued

Mean Flux ($\mu g/cm^2/hr$) Results: Across Donor Summary

| Time (hr)* | ZP-Zolmitriptan 1.9 mg |
|---|---|
| 0.625 | 284.8 ± 15.0 |
| 0.875 | 187.7 ± 11.8 |
| 1.250 | 107.3 ± 8.3 |
| 1.750 | 63.77 ± 3.70 |
| 2.250 | 41.34 ± 1.00 |
| 2.750 | 26.22 ± 0.34 |
| 3.250 | 17.14 ± 0.89 |
| 3.750 | 11.70 ± 1.22 |
| 4.250 | 8.333 ± 0.751 |
| 4.750 | 6.436 ± 0.819 |

Total Absorption and Mass Balance Results. Results of percutaneous absorption of zolmitriptan into and through ex vivo human, torso skin over 300 minutes, from a single application is summarized in table 10. Mean±SE as percent of applied dose (%) and total mass (μg).

TABLE 10

Total Absorption and Mass Balance Results across Donor Summary

| Parameter | ZP-Zolmitriptan 1.9 mg |
|---|---|
| Receptor (μg) | 1585 ± 25 |
| Dermis (μg) | 6.081 ± 0.460 |
| Epi (μg) | 6.054 ± 2.258 |
| St. Corn. (μg) | 0.929 ± 0.303 |
| S. Wash (μg) | 48.74 ± 20.74 |
| Patch (μg) | 62.11 ± 6.90 |
| Receptor (%) | 83.41 ± 1.33 |
| Dermis (%) | 0.320 ± 0.024 |
| Epi (%) | 0.319 ± 0.119 |
| St. Corn. (%) | 0.049 ± 0.016 |
| S. Wash (%) | 2.565 ± 1.092 |
| Patch (%) | 3.269 ± 0.363 |
| Total Recovery (%) | 89.94 ± 2.41 |

Conclusion and Discussion. Total absorbed zolmitriptan through the skin to the receptor solution was found to be 83.41±1.33% for the 1.9 mg patch. Peak flux occurred at approximately 4 minutes after application with a peak flux of 849.4±42.1 $\mu g/cm^2/hr$. Less than 1% of the zolmitriptan was recovered from the three skin layers at the end of the dose duration period. Mass balance was found to be approximately 90% of the applied dose.

Example 3—M207 Patch Stability

M207 patch assemblies were irradiated by e-beam and gamma irradiation up to 25 kGy dose. Subsequent irradiated patch assemblies were placed on stability at storage conditions of 25° C./60% RH and 40° C./75% RH. Results of the e-beam and gamma irradiated M207 patches are shown in Tables 11-17.

TABLE 11

Purity of non-irradiated and e-beam irradiated Zolmitriptan Patches
stored at 25° C./60% RH and 40° C./75% RH (L/N 203149)

| Treatment | Temperature (° C.) | Purity by RP-HPLC (%) | Time (Month) | | | | | | |
|---|---|---|---|---|---|---|---|---|---|
| | | | 0 | 1 | 3 | 6 | 9 | 12 | 18 |
| Control (Non-Irradiated) | 25 | avg ± std | 99.93 ± 0.03 | 100.00 ± 0.00 | 99.90 ± 0.06 | 99.91 ± 0.03 | 99.88 ± 0.03 | 99.92 ± 0.03 | 99.90 ± 0.01 |
| | 40 | avg ± std | 99.93 ± 0.03 | 100.00 ± 0.00 | 99.91 ± 0.01 | 99.91 ± 0.02 | | | |
| Irradiated | 25 | avg ± std | 99.89 ± 0.05 | 100.00 ± 0.00 | 99.93 ± 0.01 | 99.88 ± 0.02 | 99.84 ± 0.03 | 99.77 ± 0.02 | 99.82 ± 0.01 |
| | 40 | avg ± std | 99.89 ± 0.05 | 100.00 ± 0.00 | 99.93 ± 0.01 | 99.88 ± 0.01 | | | |

TABLE 12

ZP-Zolmitriptan content of non-irradiated and e-beam irradiated
Zolmitriptan Patches stored at 25° C./60% RH and 40° C./75% RH (L/N 203149)

| Treatment | Temperature (° C.) | Content (mg/patch) | Time (Month) | | | | | | |
|---|---|---|---|---|---|---|---|---|---|
| | | | 0 | 1 | 3 | 6 | 9 | 12 | 18 |
| Non-IR | 25 | avg | 1.709 | 1.698 | 1.740 | 1.771 | 1.701 | 1.758 | 1.870 |
| | | % RSD | 6.0 | 3.8 | 8.0 | 2.2 | 5.9 | 12.6 | 2.7 |
| | 40 | avg | 1.709 | 1.657 | 1.729 | 1.778 | | | |
| | | % RSD | 6.0 | 9.2 | 12.1 | 7.2 | | | |
| E-beam IR (19-24 kGy) | 25 | avg | 1.671 | 1.813 | 1.714 | 1.687 | 1.670 | 1.927 | 1.818 |
| | | % RSD | 7.9 | 8.6 | 5.8 | 10.1 | 5.3 | 5.6 | 5.4 |
| | 40 | avg | 1.671 | 1.686 | 1.801 | 1.781 | | | |
| | | % RSD | 7.9 | 7.7 | 4.3 | 5.3 | | | |

TABLE 13

Purity of gamma irradiated Zolmitriptan Patches stored at 25° C./60% RH
and 40° C./75% RH (L/N 203154)

| Treatment | Temperature (° C.) | Purity (%) | Time (Month) | | | | | |
|---|---|---|---|---|---|---|---|---|
| | | | 0 | 1 | 3 | 6 | 9 | 12 |
| Irradiated | 25 | avg ± std | 100.00 ± 0.00 | 99.95 ± 0.00 | 99.90 ± 0.01 | 99.87 ± 0.00 | 99.77 ± 0.02 | 99.79 ± 0.01 |
| | 40 | avg ± std | 100.00 ± 0.00 | 99.93 ± 0.01 | 99.90 ± 0.01 | 99.86 ± 0.00 | | |

TABLE 14

ZP-Zolmitriptan content of non-irradiated and γ-irradiated Zolmitriptan
Patches stored at 25° C./60% RH and 40° C./75% RH (L/N 203154)

| Treatment | Temperature (° C.) | Content (mg/patch) | Time (Month) | | | | | |
|---|---|---|---|---|---|---|---|---|
| | | | 0 | 1 | 3 | 6 | 9 | 12 |
| Gamma IR (25 kGy) | 25 | avg | 1.855 | 1.690 | 1.771 | 2.006 | 1.719 | 1.876 |
| | | % RSD | 4.2 | 23.5 | 2.4 | 1.8 | 13.5 | 4.5 |
| | 40 | avg | 1.855 | 1.895 | 1.818 | 1.817 | | |
| | | % RSD | 4.2 | 7.6 | 11.6 | 1.1 | | |
| Non-IR | 25 | avg | 1.918 | ND | 1.874 | 2.001 | 1.840 | 1.950 |
| | | % RSD | 10.0 | | 7.4 | 4.3 | 3.4 | 6.7 |
| | 40 | avg | 1.918 | | 1.955 | 1.895 | | |
| | | % RSD | 10.6 | | 5.1 | 7.5 | | |

ND = Not Determined.

TABLE 15

Total Impurity of non-irradiated and e-beam irradiated Zolmitriptan Patches stored at 25° C./60% RH and 40° C./75% RH (L/N 203122)

| Treatment | Temperature (° C.) | Total Impurities (%) | Time (Month) | | | | | |
|---|---|---|---|---|---|---|---|---|
| | | | 0 | 1 | 3 | 6 | 9 | 12 |
| Non-IR | 25 | avg ± std | 0.06 ± 0.02 | 0.06 ± 0.02 | 0.07 ± 0.02 | 0.01 ± 0.03 | 0.00 ± 0.00 | 0.00 ± 0.00 |
| | 40 | avg ± std | 0.06 ± 0.02 | 0.06 ± 0.03 | 0.05 ± 0.01 | 0.02 ± 0.04 | | |
| E-beam IR (21 kGy) | 25 | avg ± std | 0.06 ± 0.01 | 0.06 ± 0.00 | 0.06 ± 0.00 | 0.01 ± 0.03 | 0.00 ± 0.00 | 0.00 ± 0.00 |
| | 40 | avg ± std | 0.06 ± 0.01 | 0.09 ± 0.03 | 0.10 ± 0.04 | 0.02 ± 0.04 | | |

TABLE 16

ZP-Zolmitriptan content of non-irradiated and e-beam irradiated Zolmitriptan Patches stored at 25° C./60% RH and 40° C./75% RH (L/N 203122)

| Treatment | Temperature (° C.) | Content (mg/patch) | Time (Month) | | | | | |
|---|---|---|---|---|---|---|---|---|
| | | | 0 | 1 | 3 | 6 | 9 | 12 |
| Non-IR | 25 | avg | 1.194 | 1.235 | 1.198 | 1.343 | 1.286 | 1.326 |
| | | % RSD | 10.4 | 10.7 | 7.5 | 6.4 | 8.5 | 5.7 |
| | 40 | avg | 1.194 | 1.236 | 1.279 | 1.315 | | |
| | | % RSD | 10.4 | 7.5 | 8.7 | 5.7 | | |
| E-beam IR (21 kGy) | 25 | avg | 1.212 | 1.130 | 1.169 | 1.255 | 1.251 | 1.283 |
| | | % RSD | 6.0 | 3.3 | 6.3 | 7.7 | 7.7 | 4.9 |
| | 40 | avg | 1.212 | 1.181 | 1.191 | 1.144 | | |
| | | % RSD | 6.0 | 6.2 | 11.7 | 3.1 | | |

Solid-state physical stability was evaluated by XRD. Phase changes in amorphous vs. crystalline for zolmitriptan coating were examined by XRD analysis. M207 1.9 mg patches at initial time point (TO), 6 month and 12 month storage were analyzed. The drug coating was amorphous for both non-irradiated and gamma irradiated patches at TO. Gamma irradiated zolmitriptan patches stored at 25° C./60% RH for 12 months and 40° C./75% RH showed similar XRD pattern to that of TO patches. Percent crystallinity was calculated with peak profile fitting and the results are summarized in Table 16, below. No crystalline phase was detected for zolmitriptan formulation solids coated on gamma-irradiated patches stored under both intended (25° C./60% RH) and accelerated storage conditions (40° C./75% RH) for 12 and 6 months respectively.

TABLE 17

Phase identification and percent crystallinity for gamma-irradiated M207 1.9 mg (L/N0203154-gamma)

| Stability Condition | Phase Present | % Crystallinity |
|---|---|---|
| T0 | Ti•Titanium Hexagonal, S.G: P63/mmc (194) Phase Info [01-089-3725] Amorphous material (drug coating) | 100% (Ti) 0% (drug) |
| 6 months storage at 25° C./60% RH | Ti•Titanium Hexagonal, S.G: P63/mmc (194) Phase Info [01-089-3725] Amorphous material (drug coating) | 100% (Ti) 0% (drug) |
| 6 months storage at 40° C./75% RH | Ti•Titanium Hexagonal, S.G: P63/mmc (194) Phase Info [01-089-3725] Amorphous material (drug coating) | 100% (Ti) 0% (drug) |

TABLE 17-continued

Phase identification and percent crystallinity for gamma-irradiated M207 1.9 mg (L/N0203154-gamma)

| Stability Condition | Phase Present | % Crystallinity |
|---|---|---|
| 12 months storage at 25° C./60% RH | Ti•Titanium Hexagonal, S.G: P63/mmc (194) Phase Info [01-089-3725] Amorphous material (drug coating) | 100% (Ti) 0% (drug) |

As described herein, zolmitriptan coated microneedles were exposed to a dose of radiation in the range of approximately 7-30 kGy. More preferably in the range of 15-30 kGy to a sterility assurance level of $10^{-5}$ to $10^{-6}$. Table 17 shows 12 month stability results of irradiated and non-irradiated zolmitriptan patches that were stored at 25° C. and 40° C.

Example 4—Drug-Device Combination Product

A novel drug-device combination product (M207) was made according to the present disclosure. M207 is an intracutaneous delivery system comprising a disposable titanium microprojection member centered on an adhesive backing to form a patch. This patch was mounted in a plastic retainer ring to form a patch assembly. The patch is comprised of microneedles that are coated with the drug product formulation and dried. The retainer ring facilitates mounting of the patch to the bottom of a handheld applicator. This applicator ensures the patch is applied with a defined application energy to the site of administration. The combination of the patch assembly and the applicator comprises the intracutaneous delivery system. The applicator is held in one's hand to apply the patch. The applicator cap is twisted to unlock the applicator. When the applicator is pressed against the skin, a plunger pushes the patch out of the retainer ring and applies it to the skin.

When one applies the patch to the skin, the patch stays on the skin and the plastic ring stays on the applicator and is later detached and thrown away. The delivery system was designed to rapidly deliver a 1 mg, 1.9 mg, or 3.8 mg dose of zolmitriptan intracutaneously. The unit formulas for the M207 drug products are provided in Table 18.

TABLE 18

Unit Formula for M207 Drug Product

| Component | Amount per 1 mg Unit (mg/patch) | Amount per 1.9 mg Unit | Function |
|---|---|---|---|
| Zolmitriptan | 1 | 1.9 | Active |
| Tartaric acid | 0.3 | 0.6 | pH modifier |
| Nitrogen | N/A | N/A | Inert atmosphere for storage |

The zolmitriptan-coated titanium microneedle array is a 3 cm$^2$ array consisting of about 1987 or about 997 titanium microneedles for the 1.9 mg or 1 mg drug product, respectively. It is affixed to an approximately 5 cm$^2$ adhesive patch.

The patch may be mounted inside a polycarbonate plastic retainer ring with a co-molded desiccant. The desiccant may alternatively be attached to the lid of foil pouch. The completed patch assembly is packaged in a dry nitrogen-purged foil pouch. The user prepares the patch for application by pressing the handheld applicator onto the patch assembly. The applicator comprises a spring-loaded piston for applying the patch to the user's skin (FIGS. 4(A), 4(B), and 5(A)-(E)). The applicator is unlocked by twisting the outer grip relative to the base from the #1 position to #2 position (FIG. 5(C)). The user applies the patch by pressing the applicator mounted patch assembly onto the skin site. The applicator releases its piston at a sufficient impact energy, for example, about 0.26 Joules. The piston breaks the patch from the retainer ring and applies the patch to the skin with the prescribed impact energy density to ensure reproducible patch application. The applicator is designed to ensure that the same force is applied for each delivery and across different users.

The drug-coated microneedles penetrate or pierce the stratum corneum of the skin, enabling drug delivery. Upon administration, the solid zolmitriptan coating rapidly dissolves off of the microneedles in the interstitial fluid in the skin to form a solution and is available for absorption. The patch is removed after about 30 minutes.

The M207 system components are listed in Table 19:

TABLE 19

M207 System Components

| Component | Formulation Contact Material | Function |
|---|---|---|
| Patch Assembly and Pouch | | Primary Container Closure |
| Microneedle Array | Titanium | Microneedles hold drug formulation and pierce the stratum corneum to enable |
| Adhesive Patch | Acrylate adhesive with polyethylene backing | Affixes the microneedle array to the inner ring prior to delivery. Holds array in position |
| Inner Ring | None | Holds adhesive patch. Assembled to Outer |
| Outer Ring | None | Desiccant co-molded with the outer ring removes residual moisture from patch and maintains low-moisture environment during storage. Ring engages with applicator to |
| Pouch | None | Low oxygen and low vapor |
| Nitrogen | Nitrogen | Inert, low-moisture atmosphere for drug |
| Desiccant | | Maintains low moisture atmosphere |
| Applicator | | Provides consistent energy for repeatable patch application to a defined depth of |
| Top | None | Covers internal workings. |
| Upper Post | None | Limits travel of piston. Engages with cap to create ratchet mechanism for unidirectional |
| Twist Cup, Inner | None | Contains ledge for lockout function, and indexing cams which force rotation and align |
| Twist Cup, Outer | None | Grip surface for user interface. Contains |
| Doming Spring | None | Provides consistent force to dome skin and trigger the device. After patch application |
| Inner Cup | None | Provides structural support and bearing |
| Lower Post | None | Provides guidance for piston and holds the |
| Trigger | None | Latches on piston to retain during compression of piston spring. During user actuation, at point of full compression, the Engages with Outer Ring of Patch. Holds |
| Clear Bottom | None | Engages with Outer Ring of Patch. Holds |
| Piston Spring | None | Provides energy for application of Adhesive |
| Piston | None | Motive member which transfers energy from Piston Spring to Adhesive Patch, enabling |

Example 5—Human PK Clinical Trial

An evaluation in humans of the M207 product was performed. In this Phase 1 study, commercially available oral zolmitriptan tablet 2.5 mg and subcutaneous sumatriptan 6.0 mg were included as comparators. As described in the examples above, M207 consists of a titanium array of microneedles coated with zolmitriptan, administered intracutaneously via a patch applied by a specialized applicator. The aim of this trial was to provide information on the pharmacokinetics and tolerability of the M207 system. Assessment of the tolerability of various doses of intracutaneous zolmitriptan to a standard oral dose (2.5 mg) of zolmitriptan was also completed together with an assessment of reactions at the application site.

Specifically, the study compared single administrations of five regimens of M207, as well as 2.5 mg of oral zolmitriptan tablet and 6.0 mg of subcutaneous sumatriptan in a 7-way crossover design in 20 healthy volunteers. Analysis of the plasma samples for concentrations of zolmitriptan, N-desmethyl zolmitriptan and sumatriptan were performed at Quest Pharmaceutical Services in Groningen, Holland, by assays known in the art. In this study, the administration of M207 systems resulted in a rapid time to maximum concentration ($T_{max}$), comparable exposure to orally administered zolmitriptan, but displayed reduced exposure to the major metabolite, N-desmethyl zolmitriptan. The doses assessed in this study using the M207 system were 0.48 mg, 0.96 mg, 1.9 mg, and 3.8 mg.

The first 4 administrations of zolmitriptan utilized 5 cm² patches and a 0.26 Joule applicator in the intracutaneous microneedle system described herein. The final treatment administered was 3.8 mg on a 10 cm² patch using an applicator with 0.52 Joule of application energy in the intracutaneous microneedle system described herein. The products tested were:

M207 0.48 mg Patch Assembly: The zolmitriptan 0.48 mg patch consisted of a 3 cm² titanium array of microprojections that were nominally 340 μm in length coated with 0.48 mg of zolmitriptan. The array was applied to the center of a 5 cm² tan adhesive backing to form the patch. The patch was attached to the interior of a white to off-white polycarbonate ring co-molded with a desiccant, and this patch assembly was packaged in a foil pouch.

M207 1.9 mg Patch Assembly: The zolmitriptan 1.9 mg patch consisted of a 3 cm² titanium array of microprojections that were nominally 340 μm in length coated with 1.9 mg of zolmitriptan. The array was applied to the center of a 5 cm² tan adhesive backing to form the patch. The patch was attached to the interior of a white to off-white polycarbonate ring co-molded with a desiccant, and this patch assembly was packaged in a foil pouch.

M207 3.8 mg Patch Assembly: The zolmitriptan 3.8 mg patch consisted of a 5.5 cm² titanium array of microprojections that were nominally 340 μm in length coated with 3.8 mg of zolmitriptan. The array was applied to the center of a 10 cm² tan adhesive backing to form the patch. The patch was attached to the interior of a white to off-white polycarbonate ring co-molded with a desiccant, and this patch assembly was packaged in a foil pouch.

Study Design

This was a single-center, open-label, randomized five-way crossover study (Part 1) followed by a sequential study of two additional treatments (Parts 2 and 3). After obtaining informed consent and establishing eligibility, each subject received each of the seven study treatments once, followed by in-clinic monitoring and extensive blood sample collection for pharmacokinetic analysis. Dosing days in Part 1 occurred between 48-120 hours apart, until completion of dosing for Treatments A-E (see Table 20) in randomized order per the treatment sequence tables. Plasma samples from the initial dosing days were sent to the analytical laboratory for analysis, and tolerability for each of the dose levels was summarized. Tolerability was judged to be acceptable, and subjects returned for Part 2. During Part 2, subjects received intracutaneous administered zolmitriptan in 1.9 mg×2 patches (applied with the same 0.26 J applicator used in Part 1), and completed identical procedures to Part 1. During Part 3, subjects received a single 3.8 mg patch (applied with a 0.52 J applicator) and also completed identical procedures to the previous dosing days. After completion of the seven dosing days, subjects were assessed one final time and dismissed from the study.

The treatments used in the trial were as listed in Table 20 below:

TABLE 20

| Treatments Used In Trial |  |
| --- | --- |
| TREATMENTS | |
| Part 1 (Cross-Over Design) | |
| Treatment A | M207 intracutaneous system 0.48 mg |
| Treatment B | M207 intracutaneous system 0.48 mg × 2 |
| Treatment C | M207 intracutaneous system 1.9 mg |
| Treatment D | Zolmitriptan 2.5 mg oral |
| Treatment E | Sumatriptan 6.0 mg SC |
| Part 2 | |
| Treatment F | Zolmitriptan intracutaneous system 1.9 mg × 2 |
| Part 3 | |
| Treatment G | Zolmitriptan intracutaneous system 3.8 mg |

Twenty subjects were enrolled in the study, 10 males and 10 females. The subjects mean age was 29 years±3.5 years with a mean BMI of 24.4±3.5. With the exception of one subject who missed one treatment visit, all subjects completed all 7 treatment visits of the study, and received all 7 study treatments. In two subjects (#1010 in Treatment A and #2010 in Treatment D), very few post-dose blood samples were collected at one visit due to difficulties with venous access, but for all the rest of the subjects, virtually all of the scheduled pharmacokinetic blood samples (14 per visit) were collected for analyses.

Tolerability in Part 1 was considered acceptable, and following a review of the safety data and pharmacokinetic data from the first five dosing periods, and a discussion between the sponsor and the Principal Investigator, subjects proceeded to Parts 2 and 3 and completed those visits. The collected serum was analyzed for zolmitriptan and N-desmethyl zolmitriptan using methods well known in the art, such as using a liquid chromatography-mass spectrometry (LC-MS-MS) method.

Pharmacokinetics

The M207 patch was well-tolerated and rapid absorption was observed which were believed to potentially translate to fast pain relief for migraine or cluster headache patients. The Phase 1 results demonstrating the fast absorption of M207 that is characteristic of Zosano's microneedle patch and applicator system are illustrated below:

TABLE 21

| | M207 Characteristic of Zosano's Microneedle Patch | | | |
|---|---|---|---|---|
| | $C_{max}$ (SD) ng/ml | $T_{max}$ (range) min | $AUC_{0-2\,hr}$ (SD) ng/ml hour | $AUC_{0-last}$ (SD) ng/ml hour |
| A M207 0.48 mg | 1.8 (0.53) | 20 (2-30) | 2.1 (0.73) | 2.8 (1.36) |
| B M207 2 × 0.48 mg | 3.7 (1.05) | 20 (2-30) | 4.2 (0.95) | 6.5 (1.97) |
| C M207 1.9 mg | 6.8 (2.75) | 20 (2-30) | 7.4 (2.53) | 12.3 (4.31) |
| F M207 2 × 1.9 mg | 14.6 (4.46) | 17.5 (2-30) | 16.4 (5.34) | 27.8 (9.93) |
| G M207 3.8 mg | 22.6 (14.00) | 15 (2-30) | 19.3 (5.37) | 31.7 (8.35) |
| D Zolmitriptan 2.5 mg Oral Tablet | 3.8 (1.51) | 60 (30-240) | 4.7 (2.24) | 22.2 (10.79) |

The mean plasma concentration versus time data, for each of the six (6) zolmitriptan regimens administered are shown in FIGS. 7 and 8. FIG. 7 shows the results for the entire 24 hours sampling period and FIG. 8 shows the results for the first two hours post study drug administration only. Both figures include the subcutaneous sumatriptan concentration vs. time data (scaled for display purposes to illustrate time course). The results following SC sumatriptan were similar to several published studies of this dose and route of administration.

Figure 9:
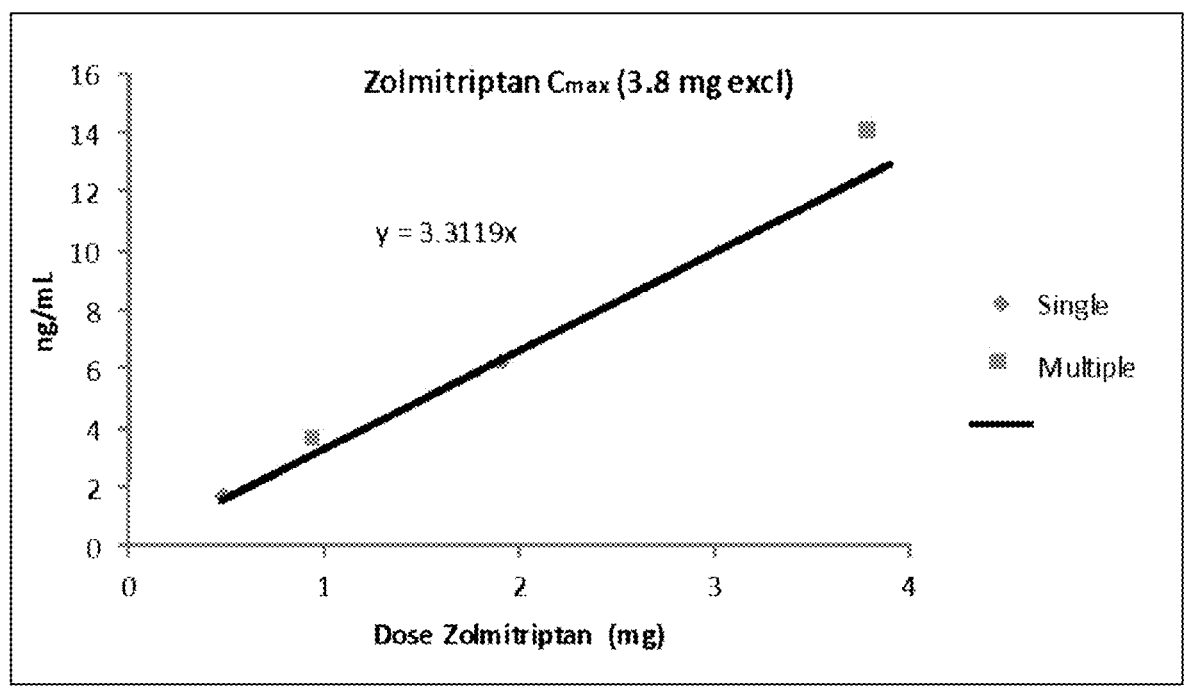
FIG. 9 is a line graph of dose linearity of M207 $C_{max}$, for single patch and multiple patches, excluding 3.8 mg.
Figure 10:
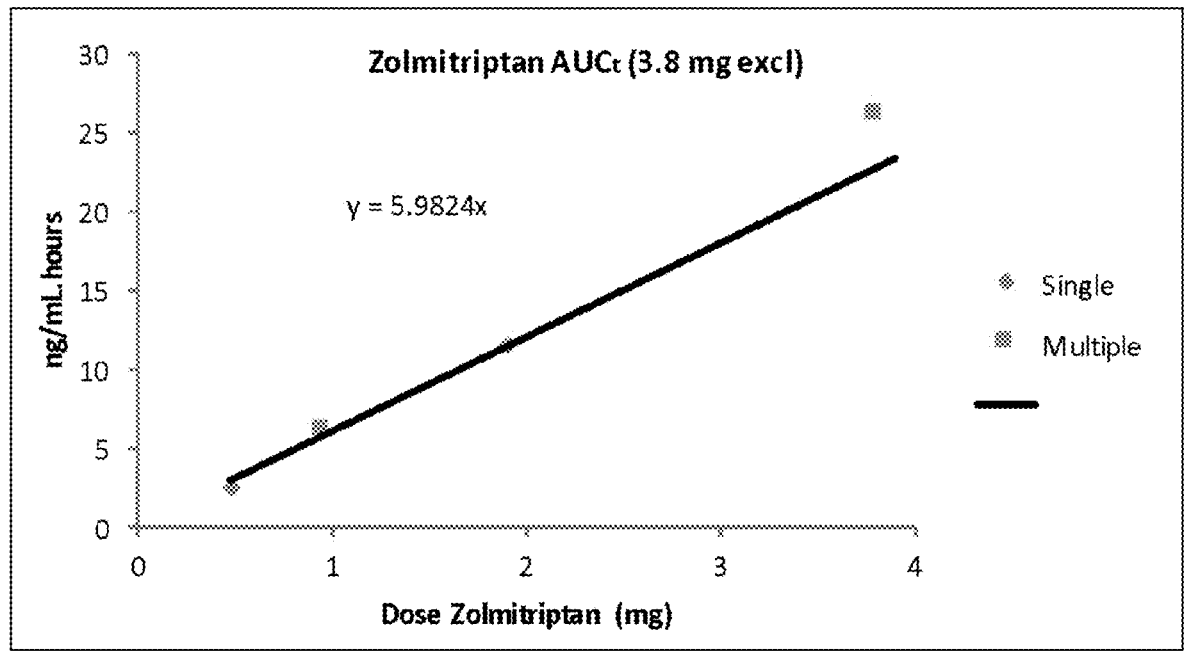
FIG. 10 is a line graph of dose linearity of M207 $AUC_t$, for single patch and multiple patches, excluding 3.8 mg.
Figure 18:
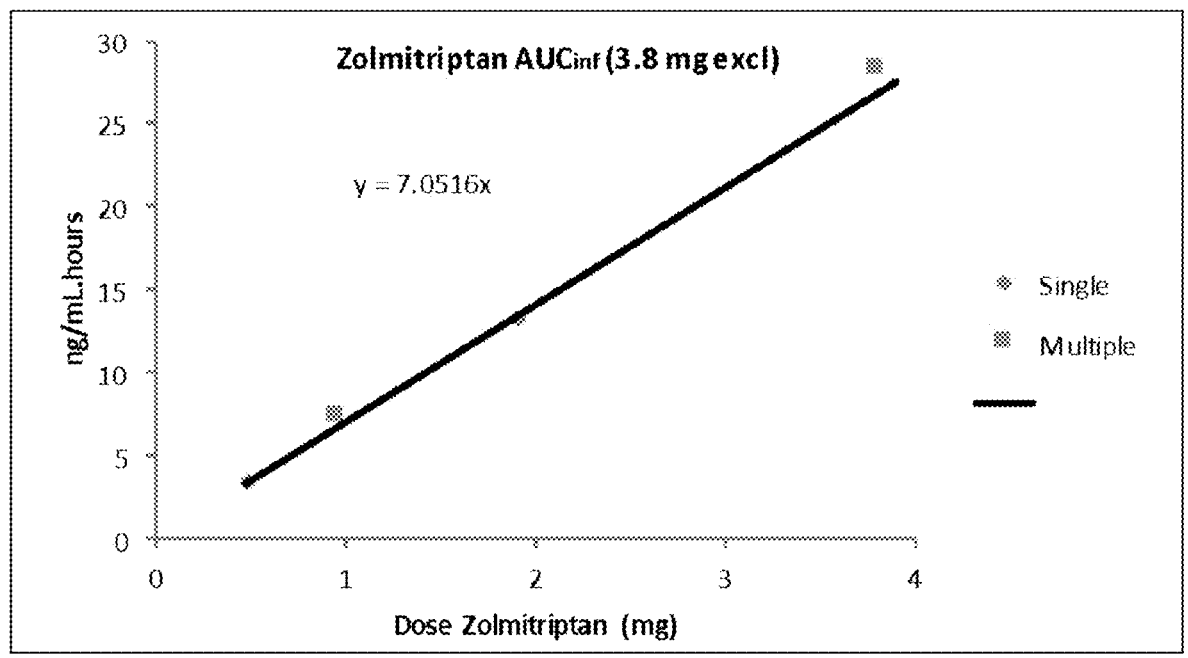
FIG. 18 is a line graph of dose linearity of M207 AUC$_{inf}$ for single patch and multiple patches, excluding 3.8 mg patch.
Figure 22:
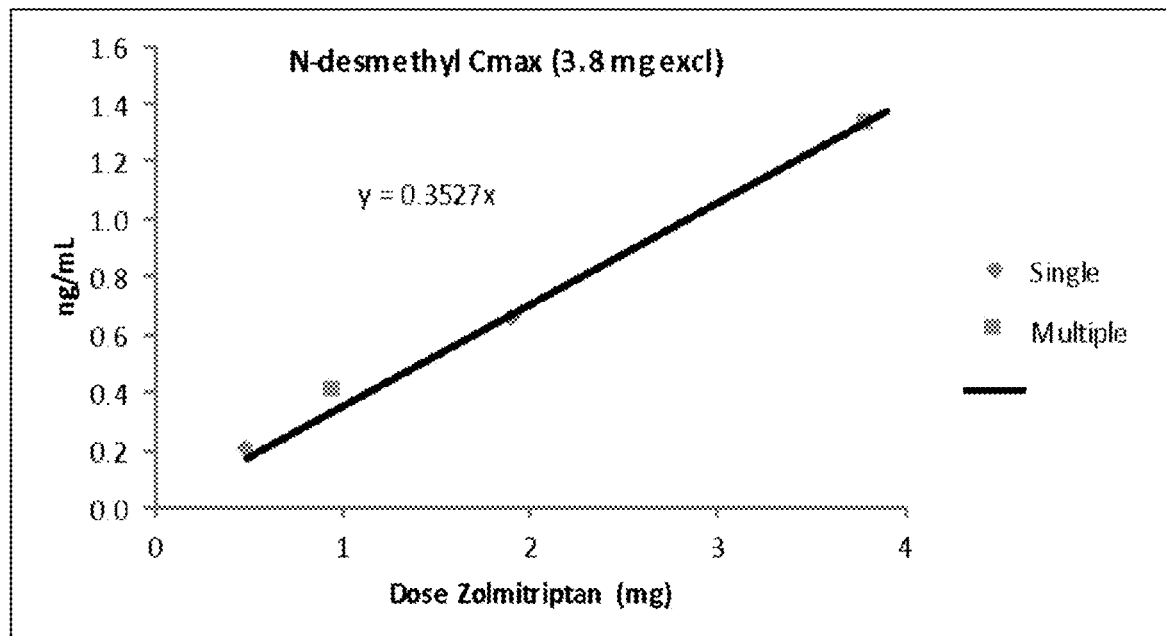
FIG. 22 is a line graph of N-desmethyl zolmitriptan dose linearity C$_{max}$ as a function of M207 dose for single patch and multiple patches, excluding 3.8 mg.
Figure 23:
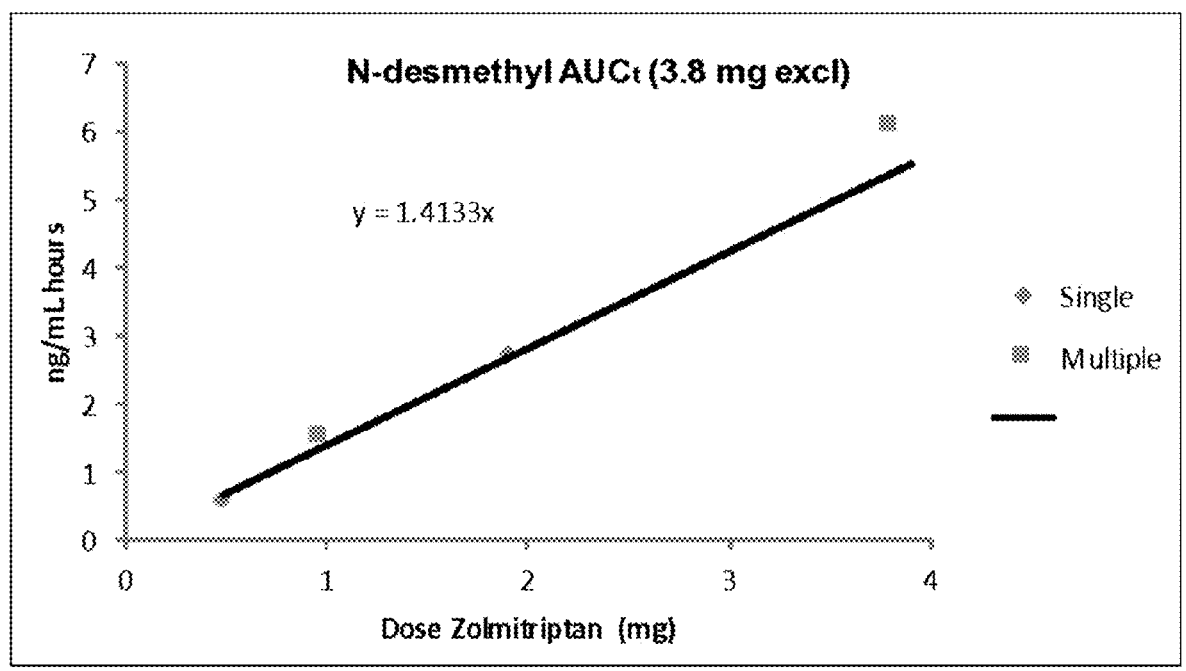
FIG. 23 is a line graph of N-desmethyl zolmitriptan dose linearity AUC$_t$ as a function of M207 dose, for single patch and multiple patches, excluding 3.8 mg.
Figure 24:
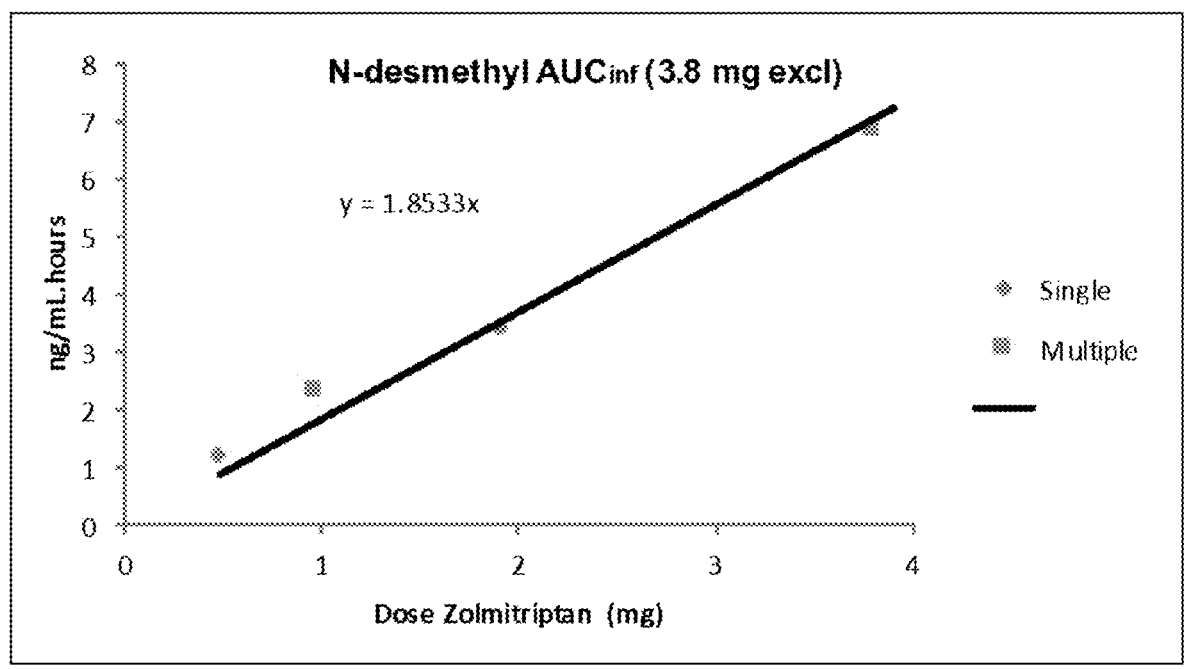
FIG. 24 is a line graph of N-desmethyl zolmitriptan dose linearity AUC$_{inf}$ as a function of M207 dose, for single patch and multiple patches, excluding 3.8 mg.

Based on the results presented in FIGS. 7 and 8, plasma levels of zolmitriptan following zolmitriptan intracutaneous application were dose-dependent, and the absorption following patch application was much faster than that seen following administration of the 2.5 mg tablet. The plasma levels seen after the single larger 3.8 mg patch were higher than those seen following 2×1.9 mg patches. Plots of dose linearity for zolmitriptan $C_{max}$, $AUC_t$, and $AUC_{inf}$ are shown in FIGS. 9, 10, and 18 (excluding the larger 3.8 mg patch). Plots of dose linearity for N-desmethyl zolmitriptan $C_{max}$, $AUC_t$, and $AUC_{inf}$ are shown in FIGS. 22-24 (excluding the larger 3.8 mg patch). Excellent dose linearity was observed over the range of doses evaluated. The calculated key mean (median for $T_{max}$) pharmacokinetic parameters for the zolmitriptan regimens and subcutaneous sumatriptan are shown in the following Table 22.

TABLE 22

| | | | | | | | |
|---|---|---|---|---|---|---|---|
| | Zolmitriptan Group PK values | | | | | | |
| GROUP | PARAMETER | $T_{max}$ | $t_{1/2}$ | $C_{max}$ | $AUC_t$ | $AUC_{inf}$ | $AUC_{2\,hrs}$ |
| A | N | 19 | 19 | 19 | 19 | 19 | 19 |
| (0.48 mg) | Mean | 17.32 | 69.06 | 1.84 | 2.81 | 3.81 | 2.11 |
| | (SD) | (12.10) | (16.26) | (0.53) | (1.36) | (1.46) | (0.73) |
| | Median | 20 | 64.62 | 1.8 | 2.78 | 3.78 | 2.11 |
| | Range | 2, 30 | 46.2, 101.46 | 0.64, 2.93 | 0.39, 6.23 | 1.37, 7.5 | 0.39, 3.53 |
| | CV % | 69.90% | 23.50% | 29.00% | 48.30% | 38.30% | 34.40% |
| B | N | 20 | 20 | 20 | 20 | 20 | 20 |
| (0.48 mg × 2) | Mean | 18.35 | 77.22 | 3.70 | 6.45 | 7.71 | 4.15 |
| | (SD) | (11.23) | (17.46) | (1.05) | (1.97) | (2.03) | (0.95) |
| | Median | 20 | 81.96 | 3.63 | 6.55 | 7.85 | 4.19 |
| | Range | 2, 30 | 41.76, 96.84 | 1.96, 6.32 | 3.16, 9.52 | 4.22, 10.98 | 2.46, 5.81 |
| | CV % | 61.20% | 22.60% | 28.40% | 30.50% | 26.30% | 22.90% |
| C | N | 20 | 20 | 20 | 20 | 20 | 20 |
| (1.9 mg) | Mean | 17.85 | 87.84 | 6.76 | 12.29 | 14.14 | 7.36 |
| | (SD) | (12.58) | (16.74) | (2.75) | (4.31) | (4.54) | (2.53) |
| | Median | 20.00 | 84.72 | 6.40 | 12.69 | 14.50 | 7.75 |
| | Range | 2, 30 | 61.20, 124.98 | 3.14, 13.20 | 5.01 19.59 | 6.55, 20.95 | 3.44, 11.46 |
| | CV % | 70.50% | 19.10% | 40.60% | 35.10% | 32.10% | 34.40% |
| D | N | 19 | 18 | 19 | 19 | 18 | 19 |
| (2.5 mg oral) | Mean | 107.37 | 196.44 | 3.77 | 22.20 | 27.19 | 4.72 |
| | (SD) | (76.37) | (48.18) | (1.51) | (10.79) | (11.34) | (2.24) |
| | Median | 60 | 196.8 | 3.7 | 22.65 | 27.1 | 4.92 |
| | Range | 30, 240 | 117.84, 288.72 | 1.66, 6.77 | 7.47, 46.85 | 14.33, 55.14 | 1.73, 9.97 |
| | CV % | 71.10% | 24.50% | 40.00% | 48.60% | 41.70% | 47.50% |
| F | N | 20 | 20 | 20 | 20 | 20 | 20 |
| (1.9 mg × 2) | Mean | 17.10 | 91.70 | 14.61 | 27.77 | 30.12 | 16.44 |
| | (SD) | (11.82) | (18.7) | (4.46) | (9.93) | (10.13) | (5.34) |
| | Median | 17.5 | 96.2 | 14.15 | 28.05 | 30.61 | 16.68 |
| | Range | 2, 30 | 60.90, 123.10 | 7.09, 25.50 | 13.24, 51.33 | 14.50, 53.38 | 7.38, 29.32 |
| | CV % | 69.10% | 20.40% | 30.50% | 35.70% | 33.60% | 32.50% |
| G | N | 20 | 20 | 20 | 20 | 20 | 20 |
| (3.8 mg) | Mean | 16.10 | 91.00 | 22.56 | 31.65 | 33.81 | 19.33 |
| | (SD) | (11.63) | (18.80) | (14.00) | (8.35) | (7.95) | (5.37) |
| | Median | 15 | 87.20 | 19.9 | 29.93 | 32.2 | 18.42 |
| | Range | 2, 30 | 60.90, 130.60 | 9.03, 70.4 | 16.90, 44.33 | 19.01, 46.41 | 9.96, 29.55 |
| | CV % | 72.20% | 20.60% | 62.10% | 26.40% | 23.50% | 27.80% |

Likely most relevant to the potential utility of this product for the treatment of migraine or cluster headache is the $T_{max}$ for the intracutaneous administered zolmitriptan regimens, showing much more rapid absorption of the zolmitriptan from intracutaneous administration, than from oral administration.

Figure 11:
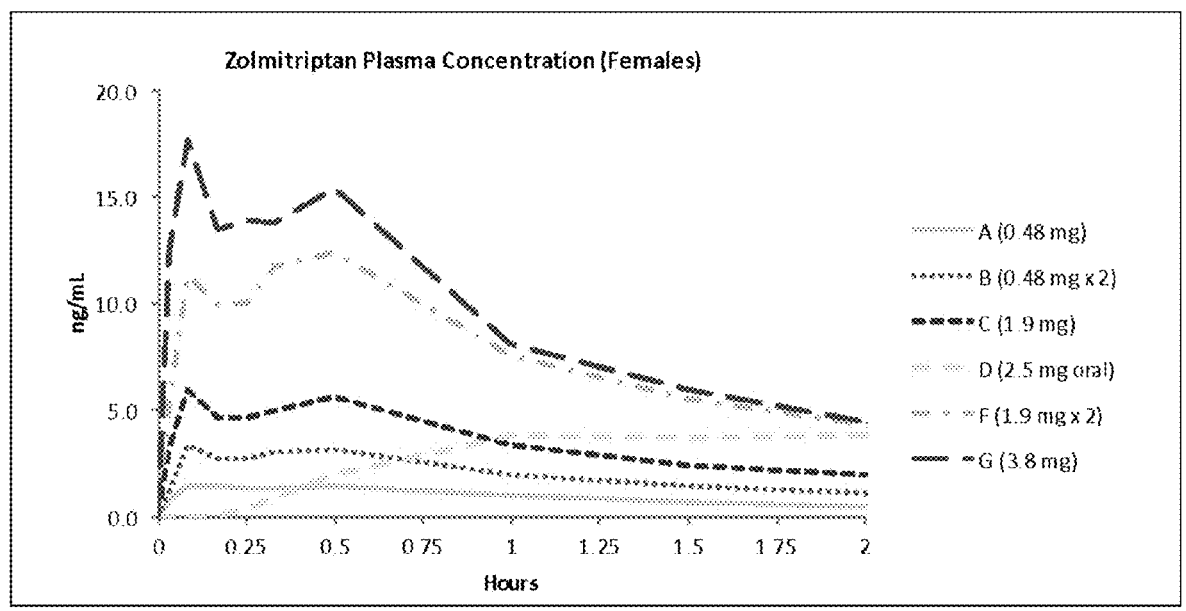
FIG. 11 is a line graph of mean plasma zolmitriptan concentrations in females over zero to two hours.
Figure 12:
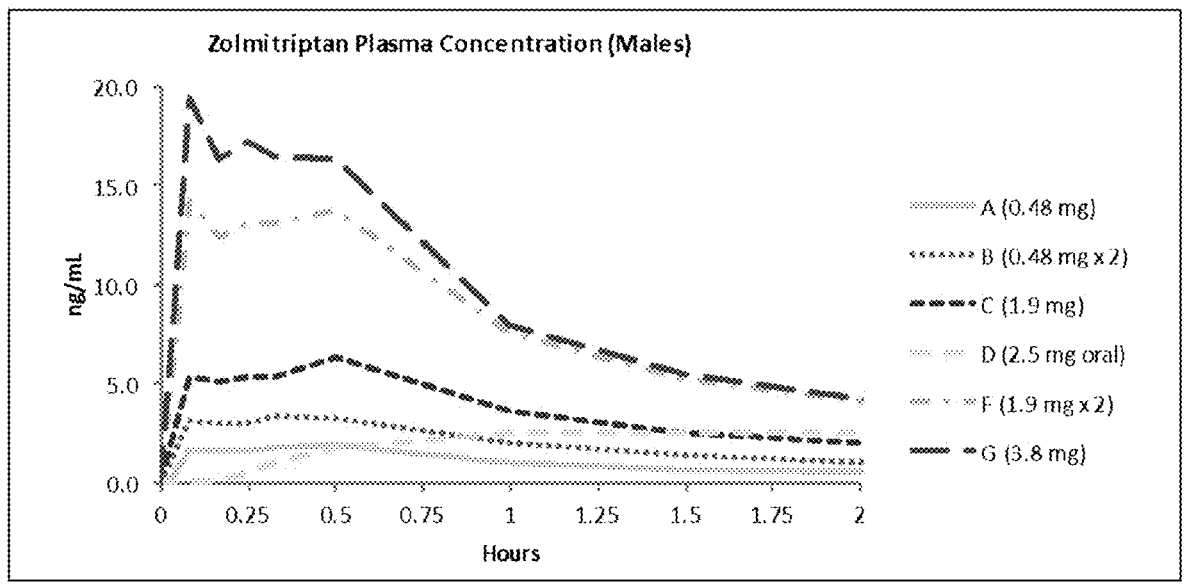
FIG. 12 is a line graph of mean plasma zolmitriptan concentrations in males over zero to two hours.

The pharmacokinetic parameters following intracutaneous administered zolmitriptan were on average very similar when comparing the results in male subjects with the results seen in female subjects, as shown in FIGS. 11 and 12.

The active metabolite, N-desmethyl zolmitriptan was detectable in all subjects dosed at the five higher dose regimens. The N-desmethyl zolmitriptan pharmacokinetic parameters for each of the zolmitriptan regimens are shown in the following Table 23.

dose linearity and proportionality of PK parameters ($AUC_t$, $AUC_{inf}$ and $C_{max}$) were compiled.

Rapid absorption of zolmitriptan was seen after intracutaneous patch application; mean peak plasma concentrations ($T_{max}$) occurred between 16.1 and 18.4 minutes. This was similar to sumatriptan SC injection (12.5±4.4 minutes) and considerably quicker than zolmitriptan tablets (107.4±76.4 minutes [1.8±1.27 hours]).

The mean (±SD) elimination half life (t1/2) for M207 systems was 1.15±0.27 hours up to 1.53±0.31 hours across the dose range of 0.48 mg to 3.8 mg, respectively. Elimination of zolmitriptan following zolmitriptan tablets (3.27±0.8 hours) was almost twice as slow as M207.

The mean (±SD) maximum plasma concentration ($C_{max}$) of zolmitriptan tablets was 3.77±1.51 ng/mL. The adminis-

TABLE 23

N-desmethyl Zolmitriptan Metabolite Group PK value

| GROUP | PARAMETER | $T_{max}$ | $t_{1/2}$ | $C_{max}$ | $AUC_t$ | $AUC_{inf}$ | $AUC_{2\,hrs}$ |
|---|---|---|---|---|---|---|---|
| A | N | 18 | 16 | 18 | 18 | 16 | 18 |
| (0.48 mg) | Mean (SD) | 65.00 | 198.41 | 0.22 | 0.70 | 1.38 | 0.31 |
|  |  | (18.55) | (98.20) | (0.05) | (0.31) | (0.476) | (0.10) |
|  | Median | 60.00 | 173.70 | 0.22 | 0.78 | 1.42 | 0.32 |
|  | Range | 30.00, 120.00 | 86.23, 511.18 | 0.14, 0.37 | 0.19, 1.26 | 0.68, 2.50 | 0.10, 0.51 |
|  | CV % | 28.5% | 49.5% | 24.6% | 44.5% | 34.5% | 31.8% |
| B | N | 20 | 20 | 20 | 20 | 20 | 20 |
| (0.48 mg × 2) | Mean (SD) | 57.75 | 196.71 | 0.42 | 1.56 | 2.43 | 0.62 |
|  |  | (14.00) | (104.70) | (0.11) | (0.57) | (0.78) | (0.17) |
|  | Median | 60.00 | 168.2 | 0.43 | 1.42 | 2.49 | 0.61 |
|  | Range | 15.00, 90.00 | 122.4, 592.5 | 0.23, 0.60 | 0.94, 3.39 | 1.44, 4.42 | 0.32, 0.94 |
|  | CV % | 24.2% | 53.2% | 27.0% | 36.4% | 31.9% | 26.9% |
| C | N | 20 | 20 | 20 | 20 | 20 | 20 |
| (1.9 mg) | Mean (SD) | 61.50 | 182.9 | 0.74 | 3.01 | 3.65 | 1.07 |
|  |  | (18.14) | (59.2) | (0.31) | (1.29) | (1.22) | (0.47) |
|  | Median | 60.00 | 165.7 | 0.81 | 3.03 | 3.62 | 1.12 |
|  | Range | 30.00, 90.00 | 87.3, 282.8 | 0.29, 1.12 | 1.10, 5.37 | 1.58, 5.91 | 0.41, 1.64 |
|  | CV % | 29.5% | 32.3% | 42.8% | 42.8% | 33.4% | 44.3% |
| D | N | 19 | 19 | 19 | 19 | 19 | 19 |
| (2.5 mg oral) | Mean (SD) | 162.63 | 192.9 | 2.08 | 13.71 | 14.55 | 2.31 |
|  |  | (77.02) | (68.1) | (0.50) | (2.91) | (3.06) | (0.93) |
|  | Median | 120.00 | 164.6 | 2.04 | 13.76 | 14.31 | 2.24 |
|  | Range | 60.00, 240.00 | 127.9, 348.9 | 1.40, 3.40 | 9.39, 19.90 | 9.90, 20.58 | 0.73, 4.64 |
|  | CV % | 47.4% | 35.3% | 24.1% | 21.3% | 21.0% | 40.3% |
| F | N | 20 | 20 | 20 | 20 | 20 | 20 |
| (1.9 mg × 2) | Mean (SD) | 63.00 | 169.0 | 1.41 | 6.50 | 7.22 | 2.15 |
|  |  | (13.42) | (27.3) | (0.46) | (2.30) | (2.34) | (0.72) |
|  | Median | 60.00 | 162.2 | 1.62 | 6.75 | 7.52 | 2.24 |
|  | Range | 30.00, 90.00 | 117.1, 215.3 | 0.65, 2.05 | 2.68, 10.74 | 3.43, 11.45 | 0.92, 3.45 |
|  | CV % | 21.3% | 16.1% | 32.4% | 35.4% | 32.5% | 33.3% |
| G | N | 20 | 20 | 20 | 20 | 20 | 20 |
| (3.8 mg) | Mean (SD) | 54.74 | 162.0 | 1.77 | 7.55 | 8.17 | 2.66 |
|  |  | (16.11) | (31.30) | (0.63) | (1.98) | (1.96) | (0.83) |
|  | Median | 60.00 | 155.3 | 1.78 | 7.48 | 8.16 | 2.69 |
|  | Range | 20.00, 90.00 | 111.1, 239.1 | 0.77, 3.54 | 3.39, 10.56 | 3.84, 11.18 | 1.19, 4.64 |
|  | CV % | 29.4% | 19.3% | 35.5% | 26.3% | 24.0% | 31.0% |

The levels of N-desmethyl zolmitriptan were significantly lower after M207 zolmitriptan intracutaneous administration than those seen following oral administration (Treatment D).

PK parameters were summarized by treatment group using descriptive statistics (arithmetic means, standard deviations, coefficients of variation, sample size, minimum, maximum, and median). In addition, geometric means and 95% confidence intervals (CIs) were calculated for $AUC_{2\,hrs}$, $AUC_t$, $AUC_{inf}$ and $C_{max}$. For each of the zolmitriptan treatments, the ratio of $AUC_{inf}$ N-desmethyl zolmitriptan/$AUC_{inf}$ zolmitriptan was calculated for each subject; a group mean was determined.

Dose proportionality was evaluated for the three doses of M207; dose proportionality was not based solely on a strict statistical rule. The relationship between dose and PK parameters of zolmitriptan were examined using a graphical approach and by descriptive statistics. Graphs of apparent tration of 2×0.48 mg patches provided an almost equivalent maximum concentration of 3.70±1.05 ng/mL; $C_{max}$ for Group C (1.9 mg) administered as a single patch was almost double (6.76±2.75 ng/mL). Groups F and G produced maximum plasma concentrations 3.9 times (14.61±4.46 ng/mL) and 6 times (22.56±14.0 ng/mL) that of zolmitriptan tablets, respectively.

Mean (±SD) total exposure ($AUC_{inf}$) was 3.81±1.46 ng·H/mL for M207 0.48 mg and 33.81±7.95 ng·H/mL for M207 3.8 mg applied as single patches. Treatment with M207 patches in Groups F and G produced a similar exposure ($AUC_{inf}$) to zolmitriptan tablets (30.12, 33.81 ng·H/mL, respectively). The mean exposure ($AUC_{inf}$) for M207 was proportional (y=8.31) to the dose for single patch administration. The concentration-time curve over zero to two hours for all treatments is displayed in FIG. 8 and zero to twenty-four hours in FIG. 7.

Plasma concentrations were slightly higher in males than females for the higher doses, Group F (2×1.9 mg) and Group G (3.8 mg). There did not appear to be a difference between genders at lower doses (Groups A [0.48 mg] to C [1.9 mg]).

The relative bioavailability of M207 systems was compared to zolmitriptan tablets using the following formula:

$$F_{rel} = \frac{AUC_{inf}(M207) \times \text{Dose(Group } D)}{AUC_{inf}(\text{Group } D) \times \text{Dose}(M207)}$$

The mean total exposure for M207 intracutaneous microneedle systems was less, relative to zolmitriptan tablets (range: 0.70-0.86). However, the mean peak exposure was 2.35 to 3.73 fold higher for intracutaneous zolmitriptan compared to zolmitriptan tablets.

A summary of the key calculated pharmacokinetic parameters from the study are shown in Table 24.

TABLE 24

| Group Formulation (dose) | Parameter | $T_{max}$ (min) | $t_{1/2}$ (H) | $C_{max}$ (ng/mL) | $AUC_{inf}$ (ng·H/mL) | $AUC_t$ (ng·H/mL) | $AUC_{2\,hrs}$ (ng·H/mL) | $F_{rel}$ $AUC_{inf}$ | $F_{rel}$ $C_{max}$ |
|---|---|---|---|---|---|---|---|---|---|
| A ZP-Zolmitriptan (0.48 mg) N = 19 | Mean (SD) | 17.3 (12.1) | 1.15 (0.27) | 1.84 (0.53) | 3.81 (1.46) | 2.81 (1.36) | 2.11 (0.73) | 0.73 | 2.60 |
| B ZP-Zolmitriptan (0.48 mg × 2) N = 20 | Mean (SD) | 18.4 (11.2) | 1.29 (0.29) | 3.70 (1.05) | 7.71 (2.03) | 6.45 (1.97) | 4.15 (0.95) | 0.77 | 2.65 |
| C ZP-Zolmitriptan (1.9 mg) N = 20 | Mean (SD) | 17.9 12.6 | 1.46 (0.28) | 6.76 (2.75) | 14.14 (4.54) | 12.29 (4.31) | 7.36 (2.53) | 0.70 | 2.35 |
| D Zolmitriptan oral tablet (2.5 mg) N = 19 | Mean (SD) | 107.4 76.4 | 3.27 (0.80) | 3.77 (1.51) | 27.19 (11.34) | 22.20 (10.79) | 4.72 (2.24) | — | — |
| E Sumatriptan SC (6.0 mg/0.5 mL) N = 20 | Mean (SD) | 12.5 4.4 | 1.14 (0.31) | 88.80 (27.56) | 105.23 (23.14) | 100.88 (23.29) | 70.88 (14.15) | — | — |
| F ZP-Zolmitriptan (1.9 mg × 2) N = 20 | Mean (SD) | 17.1 (11.8) | 1.53 (0.31) | 14.61 (4.46) | 30.12 (10.13) | 27.77 (9.93) | 16.44 (5.34) | 0.74 | 2.63 |
| G ZP-Zolmitriptan (3.8 mg) N = 20 | Mean (SD) | 16.1 (11.6) | 1.52 (0.31) | 22.56 (14.00) | 33.81 (7.95) | 31.65 (8.35) | 19.33 (5.37) | 0.86 | 3.73 |

Approximately twice the amount of the active metabolite, N-desmethyl zolmitriptan was formed following zolmitriptan oral administration (mean 59.8±16%) compared to those seen following M207 (Table 25).

TABLE 25

N-desmethyl Zolmitriptan/Zolmitriptan Metabolite Ratio

| PARAMETER | GROUP | | | | | |
|---|---|---|---|---|---|---|
| | A | B | C | D | F | G |
| Metabolite ratio | (0.48 mg) | (0.48 mg × 2) | (1.9 mg) | (2.5 mg oral) | (1.9 mg ×) | (3.8 mg) |
| N | 16 | 20 | 20 | 18 | 20 | 20 |
| Mean (%) | 35.1 | 31.7 | 25.9 | 59.8 | 24.3 | 24.2 |
| (SD) | (10.1) | (5.8) | (3.6) | (16.0) | (4.2) | (3.8) |
| Median (%) | 33.6 | 31.1 | 25.2 | 56.9 | 23.4 | 24.0 |
| Range (min, max %) | 23.1, 61.9 | 22.4, 46.2 | 19.5, 35.7 | 29.9, 89.4 | 17.6, 34.1 | 19.0, 32.1 |

The relative bioavailability of the active metabolite, N-desmethyl zolmitriptan produced for M207 patches was compared to zolmitriptan tablets using the following formula:

$$F_{rel} = \frac{\text{N-desmethyl zolmitriptan } AUC_{inf}(M207) \times \text{Dose(Group } D)}{\text{N-desmethyl zolmitriptan } AUC_{inf}(\text{Group } D) \times \text{Dose}(M207)}$$

There was less conversion to the N-desmethyl zolmitriptan metabolite for M207 patches compared to zolmitriptan tabs ($F_{rel}$ AUC range: 0.32-0.46) and approximately 50% less rate of exposure for M207 patches compared to zolmitriptan tablets based the relative bioavailability of $C_{max}$.

Figure 13:
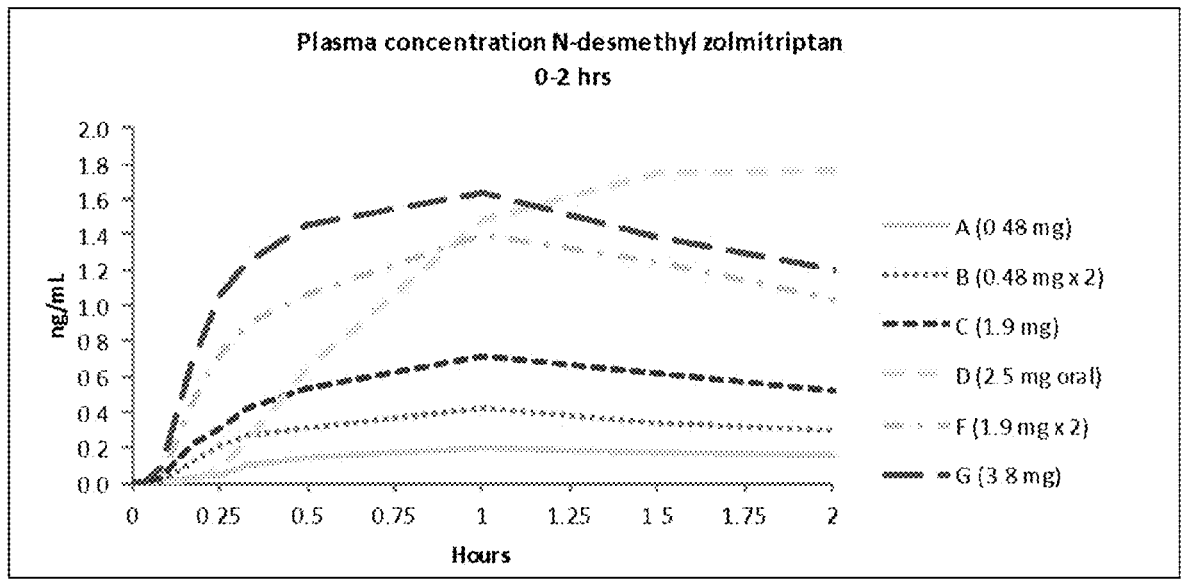
FIG. 13 is a line graph of mean plasma N-desmethyl zolmitriptan concentration over zero to two hours.
Figure 14:
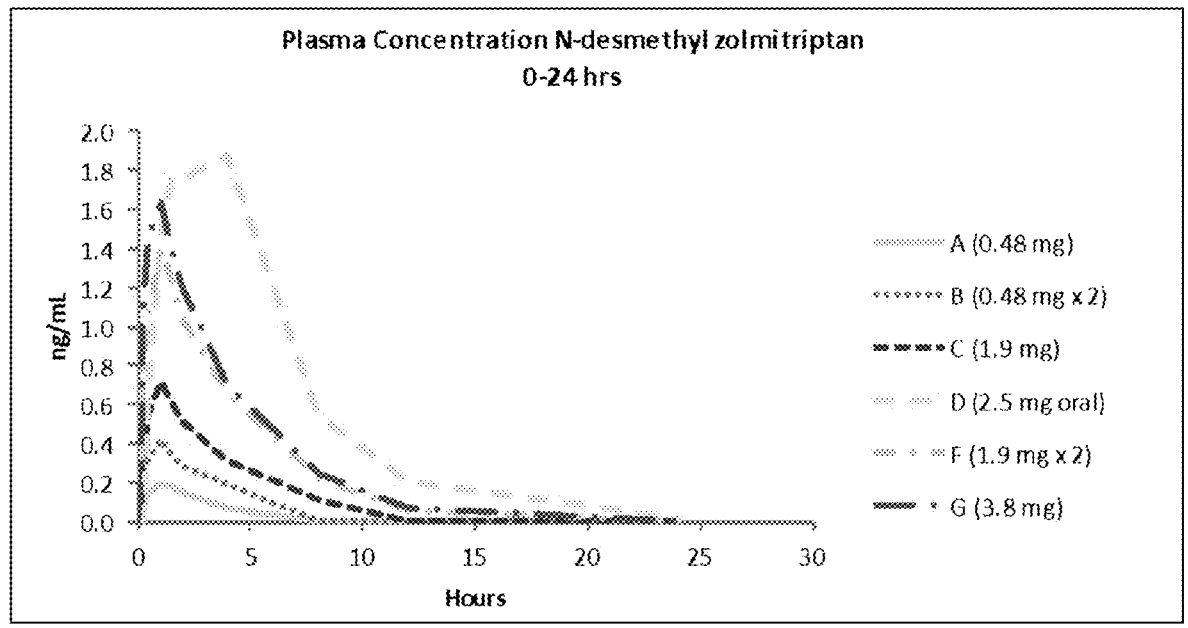
FIG. 14 is a line graph of mean N-desmethyl zolmitriptan plasma concentrations over zero to twenty-four hours.

Plasma concentrations of the N-desmethyl metabolite reached maximum at around 1 hour (range: 54.7-65.0 minutes) for M207 administered via the intracutaneous route compared to (162.6 minutes [2.71 H] for zolmitriptan tablets, FIG. 13. The elimination half life ($t_{1/2}$) for the metabolite was comparable for all treatments including oral administration (range 2.7 H to 3.31 H]). The concentration-time curve from 0-24 hours for N-desmethyl zolmitriptan is displayed in FIG. 14.

Figure 19:
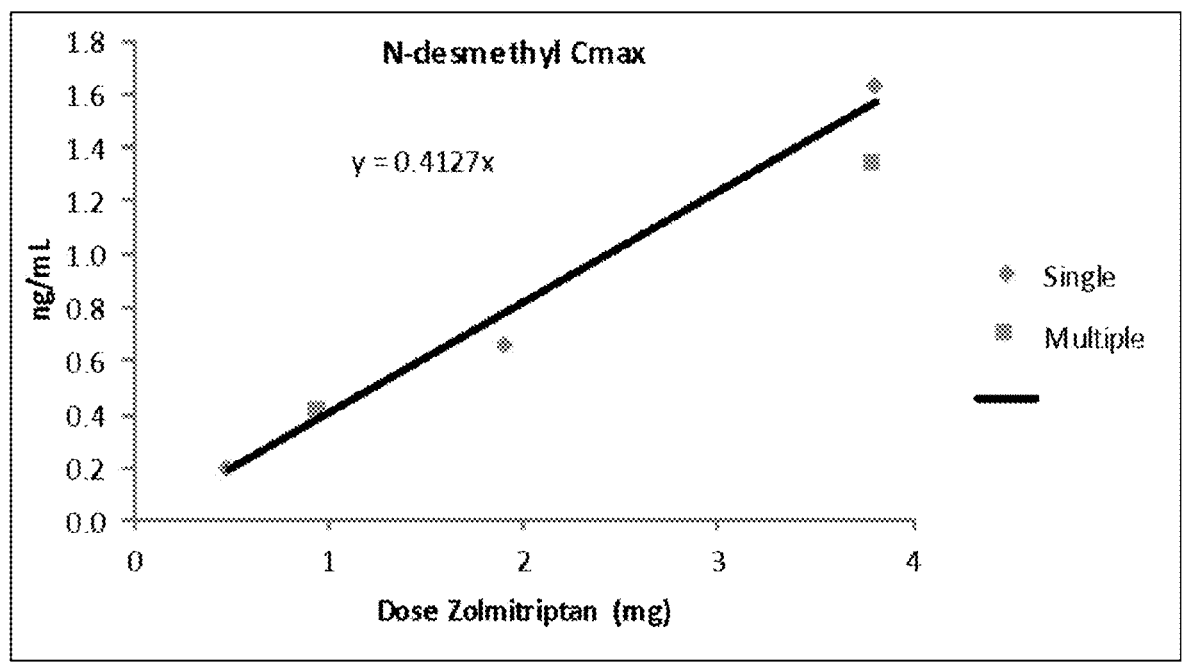
FIG. 19 is a line graph of N-desmethyl zolmitriptan dose linearity C$_{max}$ as a function of M207 dose for single patch and multiple patches.
Figure 21:
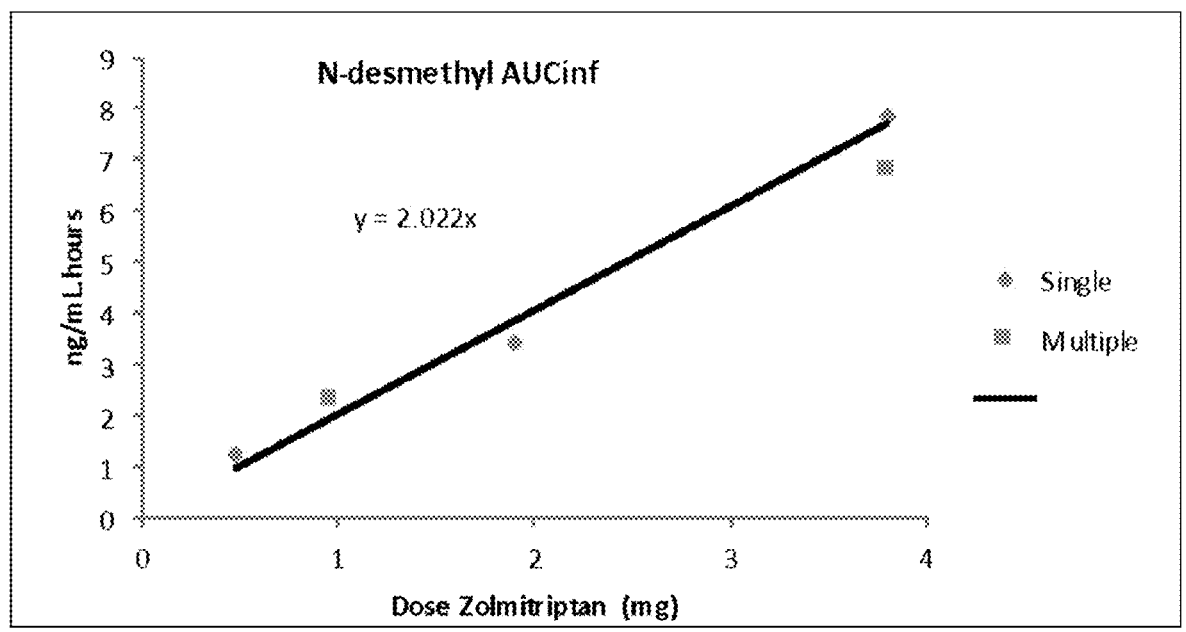
FIG. 21 is a line graph of N-desmethyl zolmitriptan dose linearity AUC$_{inf}$ as a function of M207 dose for single patch and multiple patches.

Mean maximum plasma concentration ($C_{max}$) for the M207 0.48 mg dose was 0.22 ng/mL and 1.77 ng/mL for the 3.8 mg strength compared to 2.08 ng/mL for zolmitriptan tablets. Mean $AUC_{inf}$ was 1.38 ng·H/mL for the 0.48 mg strength up to 8.17 ng·H/mL for the 3.8 mg strength versus 14.55 ng·H/mL for zolmitriptan tablets. The extent ($C_{max}$ and $AUC_{inf}$) of the N-desmethyl metabolite for M207 patches were directly proportional (y=0.4127 and 2.022, respectively) to the dose and considerably lower than that for zolmitriptan tablets. See FIGS. 19 and 21.

A summary of the mean pharmacokinetic parameters for N-desmethyl zolmitriptan is detailed in Table 26.

M207 also tended to have less intragroup variability (as indicated by the CV % s) for the $AUC_{inf}$ parameter compared to the zolmitriptan tablets.

Dose Linearity for M207 System Administration

Figure 15:
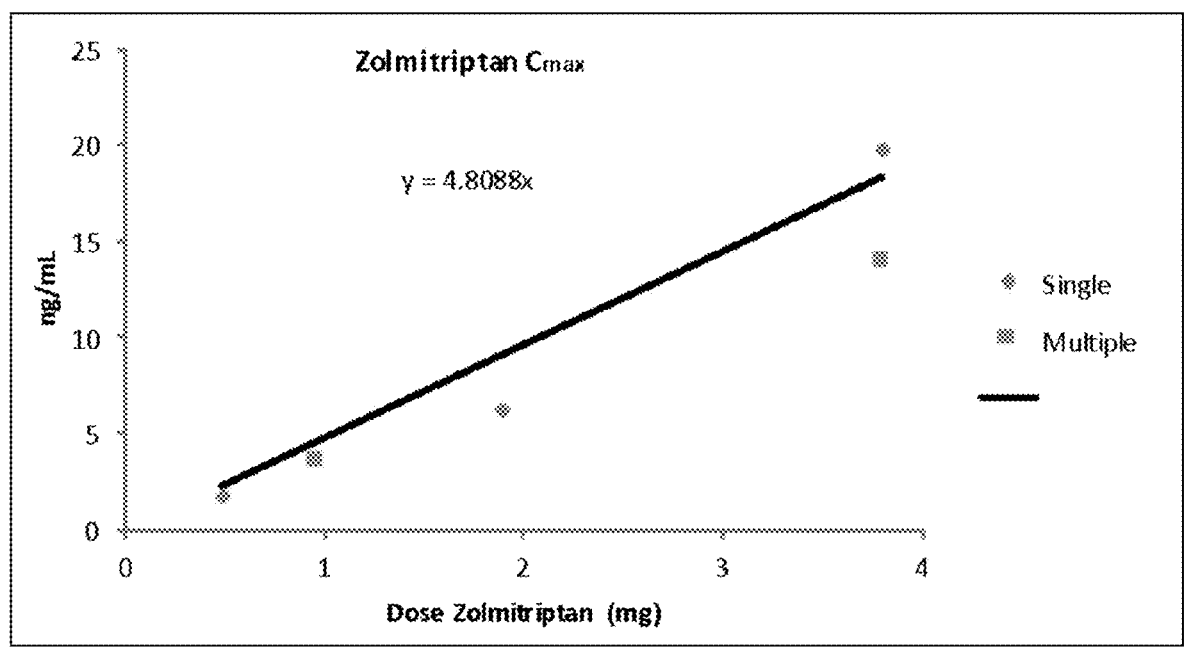
FIG. 15 is a line graph of dose linearity of M207 $C_{max}$ for single patch and multiple patches.
Figure 16:
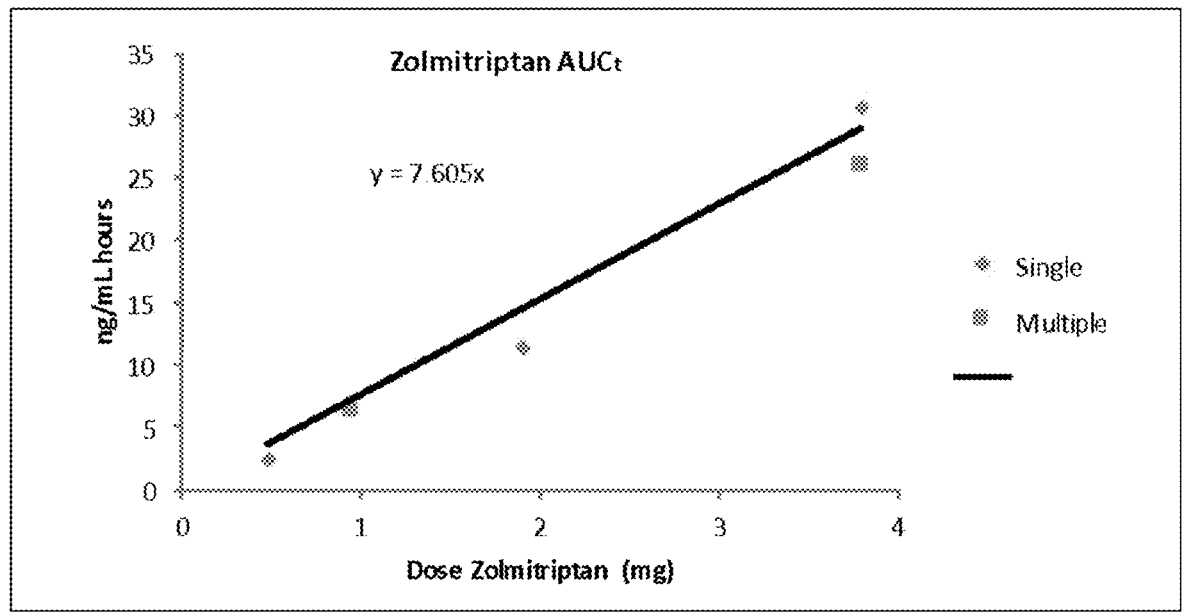
FIG. 16 is a line graph of dose linearity of M207 AUC$_t$ for single patch and multiple patches.
Figure 17:
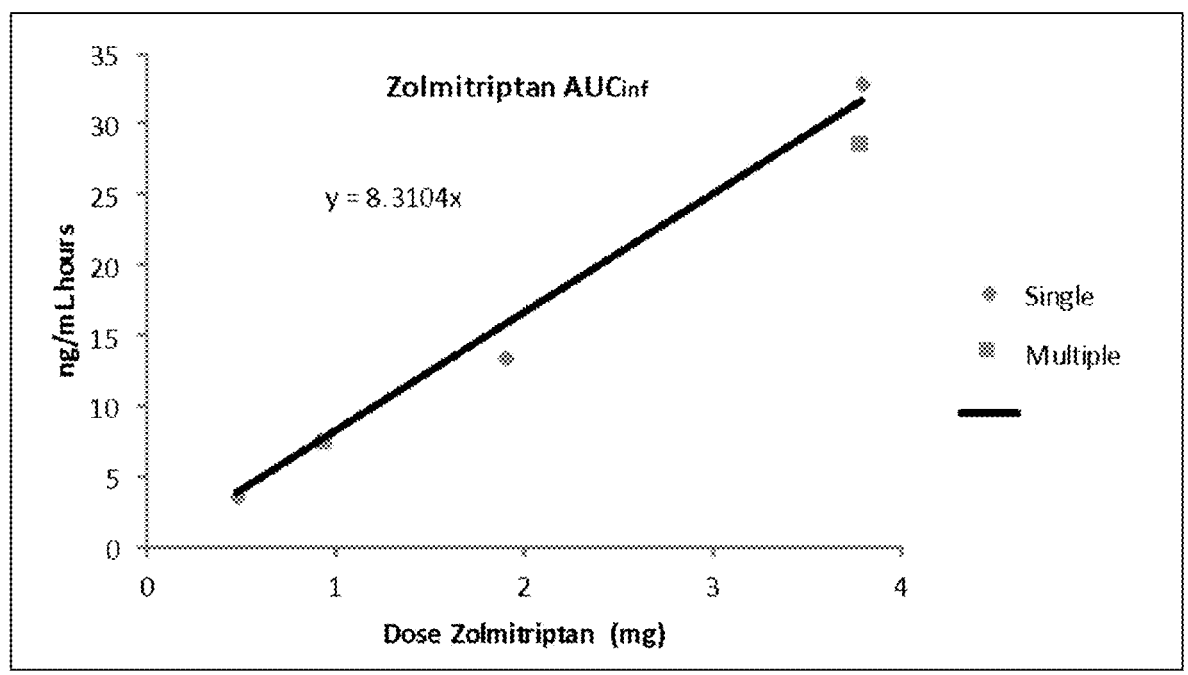
FIG. 17 is a line graph of dose linearity of M207 AUC$_{inf}$ for single patch and multiple patches.
Figure 20:
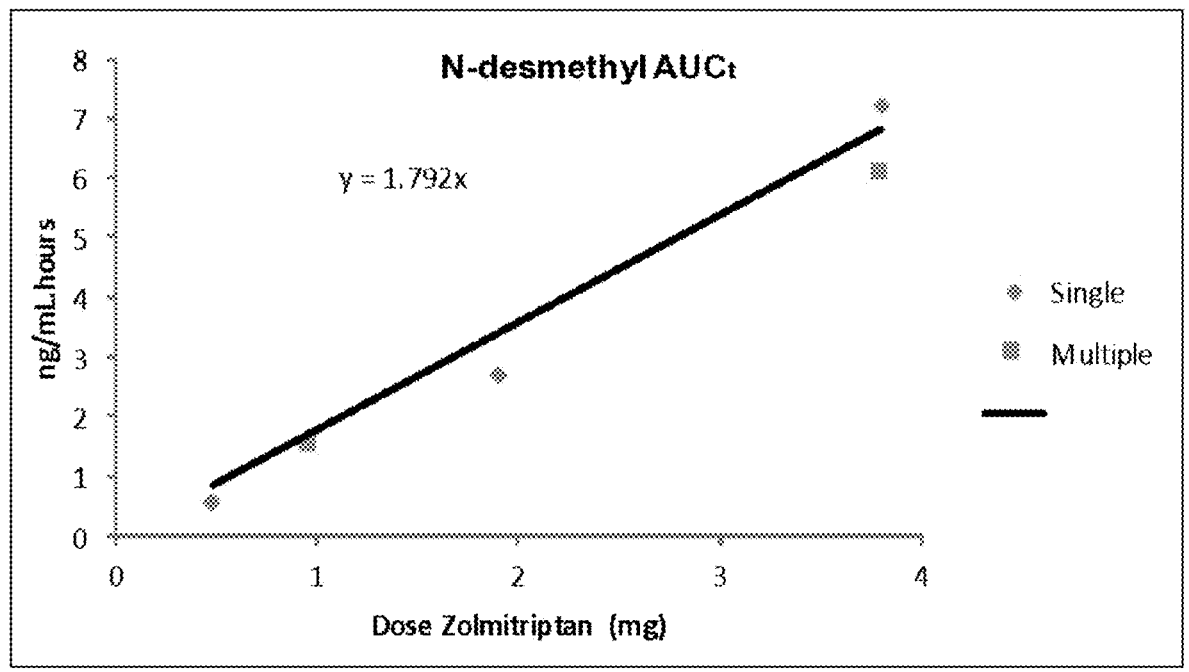
FIG. 20 is a line graph of N-desmethyl zolmitriptan dose linearity AUC$_t$ as a function of M207 dose for single patch and multiple patches.

A positive linear association and was seen for $C_{max}$ (y=4.81), $AUC_t$ (y=7.61) and $AUC_{inf}$ (y=8.31) for both single (0.48 mg, 1.9 mg and 3.8 mg) and multiple (0.48 mg×2 and 1.9 mg×2) system administration. See FIGS. 15-17. At the lower end of the dosing range (0.48 mg×2), concentrations of both the zolmitriptan and the N-desmethyl zolmitriptan metabolite were very comparable. However, at the highest dose (1.9 mg×2), plasma concentrations achieved with multiple patch administration were slightly less than that with a single patch (and the 0.52 J administration force) for both zolmitriptan and the N-desmethyl zolmitriptan. For N-desmethyl zolmitriptan, see FIGS. 19-21.

M207 patch administration resulted in rapid peak plasma concentrations ($T_{max}$) that occurred within 20 minutes of patch application. This compared favorably with 12.5 minutes for SC sumatriptan and offers a considerable improvement over conventional release oral zolmitriptan tablets (1.8 hours). Elimination rate ($t_{1/2}$) for M207 was shorter, approximately twice the rate of zolmitriptan tablets (1.2-1.5 hours versus 3.3 hours).

$C_{max}$ for zolmitriptan tablets was 3.77 ng/mL. Treatment with M207 patches in Groups C (1.9 mg), F (1.9 mg×2) and G (3.8 mg) produced 1.8, 3.9 and 6 times higher mean peak plasma concentration than zolmitriptan 2.5 mg tablets. Multiple patch administration with 2×0.48 mg M207 produced a comparable $C_{max}$ (3.70 ng/mL) to oral zolmitriptan tablets.

Treatment with M207 patches in Groups F and G produced a similar exposure ($AUC_{inf}$) to oral zolmitriptan tablets (30.12, 33.81 and 27.19 ng·H/mL, respectively). However, the mean total exposure ($AUC_{inf}$) for M207 patches was less (0.700-0.86) and the mean peak exposure ($C_{max}$) was 2.35 to 3.73 fold higher, relative to oral zolmitriptan tablets.

The time to peak plasma concentration of the N-desmethyl metabolite from M207 was considerably faster at

TABLE 26

Mean (SD) PK parameters for N-desmethyl zolmitriptan metabolite

| Group Formulation (dose) | Parameter | $T_{max}$ (min) | $t_{1/2}$ (H) | $C_{max}$ (ng/mL) | $AUC_{inf}$ (ng · H/mL) | $AUC_t$ (ng · H/mL) | $F_{rel}$ $AUC_{inf}$ | $F_{rel}$ $C_{max}$ |
|---|---|---|---|---|---|---|---|---|
| A ZP-Zolmitriptan (0.48 mg) | Mean | 65.0 | 3.31 | 0.22 | 1.38 | 0.70 | 0.46 | 0.52 |
| | SD | (18.6) | (1.64) | (0.05) | (0.48) | (0.31) | | |
| B ZP-Zolmitriptan (0.48 mg × 2) | Mean | 57.8 | 3.28 | 0.42 | 2.43 | 1.56 | 0.43 | 0.52 |
| | SD | (14.0) | (1.75) | (0.11) | (0.78) | (0.57) | | |
| C ZP-Zolmitriptan (1.9 mg) | Mean | 61.5 | 3.05 | 0.74 | 3.65 | 3.01 | 0.32 | 0.43 |
| | SD | (18.1) | (0.99) | (0.32) | (1.22) | (1.29) | | |
| D Zolmitriptan oral tablet (2.5 mg) | Mean | 162.6 | 3.22 | 2.08 | 14.55 | 13.71 | — | — |
| | SD | (77.0) | (1.14) | (0.50) | (3.06) | (2.91) | | |
| F ZP-Zolmitriptan (1.9 mg × 2) | Mean | 63.0 | 2.82 | 1.41 | 7.21 | 6.50 | 0.32 | 0.43 |
| | SD | (13.4) | (0.45) | (0.48) | (2.34) | (2.30) | | |
| G ZP-Zolmitriptan (3.8 mg) | Mean | 54.7 | 2.70 | 1.77 | 8.17 | 7.55 | 0.36 | 0.52 |
| | SD | (16.1) | (0.52) | (0.63) | (1.96) | (1.98) | | | around 1 hour versus 2.7 hours for oral zolmitriptan. However, the extent of metabolite produced from M207 was about 50% less than oral zolmitriptan tablets. The key PK findings are summarized in Table 27 below.

Adverse events (AE) were predominantly mild (87%), of a short (<24 hour) duration and the majority were consistent with events previously reported with zolmitriptan (88%). There were no severe or serious AEs. Transient changes in

TABLE 27

Key Pharmacokinetic Parameters

| | Dose (mg) | $C_{max}$ (SD) ng/mL | $T_{max}$ Med (Range) | $AUC_{0-2hr}$ (SD) ng/mL hour | $AUC_{0-last}$ (SD) ng/mL hour | $AUC_{0-last}$ Dose | BA v Oral |
|---|---|---|---|---|---|---|---|
| A (ZP Zolmi) | 0.48 | 1.8 (0.53) | 20 (2-30) | 2.1 (0.73) | 2.8 (1.36) | 5.8 | 67% |
| B (ZP Zolmi) | 0.48 × 2 | 3.7 (1.05) | 20 (2-30) | 4.2 (0.95) | 6.5 (1.97) | 7.5 | 87% |
| C (ZP Zolmi) | 1.9 | 6.8 (2.75) | 20 (2-30) | 7.4 (2.53) | 12.3 (4.31) | 6.5 | 76% |
| F (ZP Zolmi) | 1.9 × 2 | 14.6 (4.46) | 17.5 (2-30) | 16.4 (5.34) | 27.8 (9.93) | 7.3 | 85% |
| G (ZP Zolmi) | 3.8 | 22.6 (14.00) | 15 (2-30) | 19.3 (5.37) | 31.7 (8.35) | 8.3 | 97% |
| D (Oral Zolmi) | 2.5 | 3.8 (1.51) | 60 (30-240) | 4.7 (2.24) | 22.2 (10.79) | 8.6 | 100% |
| E (SC Suma) | 6.0 | 88.8 (27.56) | 10 (5-20) | 70.9 (14.15) | 100.9 (23.29) | 16.8 | |

Perhaps most relevant to the potential utility of this product for the treatment of migraine or cluster headache is the $T_{max}$ for the M207 regimens, showing much more rapid absorption of the zolmitriptan from intracutaneous administration, than from oral administration.

A comparison of exposure is provided in Table 28 below.

TABLE 28

Comparison of exposure - M207 vs. Oral Zolmitriptan (Phase 1 Study and Literature Comparisons)

| Treatment (Study) | $C_{max}$ (ng/ml) | $AUC_{0-last}$ (ng/ml * hr) |
|---|---|---|
| M207 0.96 mg (Study) | 3.73 | 6.5 |
| M207 1.9 mg (Study) | 6.40 | 12.3 |
| M207 2 × 1.9 mg (Study) | 14.6 | 27.8 |
| Zolmitriptan 2.5 mg oral (Study) | 3.8 | 22.2 |
| Zolmitriptan 10 mg oral (Seaber1997) | 16.6(M)-20.9(F) | 84.4(M)-108.6(F) |

There was excellent dose linearity observed for high and low dose for $C_{max}$ and $AUC_{inf}$. M207 was well-tolerated.

both systolic and diastolic blood pressure occurred, and for both systolic and diastolic blood pressure, the pressure values returned to pre treatment levels 1-2 hours after drug administration. No significant ECG changes occurred. Application of the patch was tolerated well with mostly mild to moderate reactions that resolved after 24 hours. Local tolerability of the 3.8 mg patch applied with greater force (0.52 J) was not as favorable as the other regimens.

The M207 intracutaneous delivery system offers pharmacokinetic advantages over zolmitriptan tablets that should result in a faster onset of action, comparable exposure and reduced first-pass metabolism with the lowered potential for drug interactions and adverse events. Importantly, delivery is via a method that does not involve the gastrointestinal route or the injection method. Further comparison to the zolmitriptan conventional oral tablet is set forth below in Tables 29 and 30.

TABLE 29

Ratios of M207 vs. Group D (oral zolmitriptan 2.5 mg tablets)

| PARAMETER | | GROUP (dose) | | | | |
|---|---|---|---|---|---|---|
| Ratios vs. Group D (2.5 mg) | | A (0.48 mg) | B (0.48 mg × 2) | C (1.9 mg) | F (1.9 mg × 2) | G (3.8 mg) |
| $C_{max}$ | Ratio vs. D | 0.50 | 1.02 | 1.79 | 4.00 | 5.56 |
| | 90% CI | 0.42, 0.60 | 0.85, 1.2 | 1.52, 2.13 | 3.23, 5.00 | 4.55, 7.14 |
| $AUC_1$ | Ratio vs. D | 0.12 | 0.31 | 0.58 | 1.32 | 1.55 |
| | 90% CI | 0.10, 0.15 | 0.25, 0.38 | 0.47, 0.71 | 1.09, 1.59 | 1.28, 1.87 |
| $AUC_{inf}$ | Ratio vs. D | 0.14 | 0.3 | 0.53 | 1.15 | 1.32 |
| | 90% CI | 0.12, 0.16 | 0.25, 0.35 | 0.45, 0.62 | 0.97, 1.35 | 1.12, 1.56 |
| $AUC_{2\ hrs}$ | Ratio vs. D | 0.46 | 0.96 | 1.63 | 3.69 | 4.41 |
| | 90% CI | 0.38, 0.55 | 0.80, 1.15 | 1.36, 1.96 | 3.04, 4.48 | 3.63, 5.36 |

TABLE 30

Ratios of N-desmethyl Zolmitriptan vs. Group D
(oral zolmitriptan 2.5 mg tablets)

| PARAMETER | | GROUP (dose) | | | | |
|---|---|---|---|---|---|---|
| Ratio vs. Group D (2.5 mg oral) | | A (0.48 mg) | B (0.48 mg × 2) | C (1.9 mg) | F (1.9 mg × 2) | G (3.8 mg) |
| $C_{max}$ | Ratio vs. D | 0.10 | 0.02 | 0.32 | 0.65 | 0.79 |
| | 90% CI | 0.09, 0.11 | 0.18, 0.23 | 0.26, 0.37 | 0.56, 076 | 0.68, 0.93 |
| $AUC_1$ | Ratio vs. D | 0.04 | 0.11 | 0.20 | 0.45 | 0.54 |
| | 90% CI | 0.04, 0.05 | 0.09, 0.13 | 0.17, 0.24 | 0.39, 0.53 | 0.46, 0.63 |
| $AUC_{inf}$ | Ratio vs. D | 0.09 | 0.16 | 0.24 | 0.48 | 0.55 |
| | 90% CI | 0.08, 0.10 | 0.14, 0.19 | 0.21, 0.28 | 0.42, 0.55 | 0.48, 0.63 |
| $AUC_{2\ hrs}$ | Ratio vs. D | 0.13 | 0.28 | 0.45 | 0.93 | 1.14 |
| | 90% CI | 0.11, 0.15 | 0.24, 0.32 | 0.38, 0.52 | 0.78, 1.13 | 0.95, 1.38 |

Example 6—In Vivo Pig Study

The M207 patch was tested in swine. Intravenously administered zolmitriptan was used as a control. The inner thigh of the swine was used as the site of administration.

Determination of Zolmitriptan by LC/MS/MS Method

The analysis for zolmitriptan from used patches, skin swabs and plasma PK samples was performed using established in-house LC/MS/MS methods. The low limit of quantitation (LLOQ) and high-limit of quantitation (HLOQ) were 0.1 and 1000 ng/mL, respectively. A four minute method utilizing high performance liquid chromatography-electrospray ionization-tandem mass spectrometry (HPLC-ESI-MS/MS) was developed for quantitation of zolmitriptan and its two major metabolites in HGP plasma. The instrumentation consist of Agilent® 1200 pumps, CTC PAL® Autosampler with cooling stack, AB Sciex® TurboV® ESI source, and API 4000® mass spectrometer.

All plasma samples and standards were first protein precipitated using 100% methanol and then diluted with 30% solution of acetonitrile at 1:2 ratio (Plasma: 30% ACN), 20 µL of this solution was injected into autosample. The autosample was equipped with a 100 µL syringe and a 100 µL loop. The syring and the loop were washed twice with solvent 1 (0.2% formic acid) and solvent 2 (0.2% formic acid in acetonitrile) between each injections.

A 10-port 2 position Valco® valve was placed in-line with the mass spectrometer equipped with a guard cartridge (Zorbax 300SB-C8, 12.5×4.6 mm) used for on-line solid phase extraction (SPE). This valve was setup such that in the "load" position, the sample was injected onto the cartridge and was washed with 10% mobile phase B for 30 seconds, next the valve was switched into the "inject" position, where the cleaned sample would eluted from the SPE cartridge in reversed direction onto the analytical column (Luna PFP(2), 100 A, 5 µm, 50×2 mm) and into the mass spectrometer.

The HPLC method used was a reversed phase gradient method (0.0 min, 10% B; 0.5 min, 10% B; 1.0 min, 40% B; 1.7 min, 40% B; 2.1 min, 10% B; 4.0 min, 10% B). HPLC mobile phases consist of 20 mM Ammonium Acetate as mobile phase A, and 80% acetonitrile in 20% 20 mM Ammonium Acetate as mobile phase B. The source setting for all analysis were the following: Collision gas (CAD)=12; Curtain gas (CUR)=25; Ion source gas 1 (GS1)=60; ion source gas 2 (GS2)=60; Ion spray Voltage (IS)=5500; Temperature (TEM)=600; interface Heater (ihe)=on. During the mass spectrometer acquisition, eleven MRM transitions were monitored. All eleven MRM transitions were used for data processing. The peak areas under each corresponding MRM transitions were summed and compared to that of spiked standard plasma samples to calculated concentration for each sample. A quadratic (1/x) fitting was used for all calculations.

Anesthesia

Animals were induced with Telazol intramuscular and maintained with isoflurane on a ventilator.

Blood Sample Collection for Pharmacokinetic Studies

Blood samples were collected from one or more of the following blood vessels in the animals: marginal ear veins/artery (left/right), saphenous veins (left/right), mammary veins (left/right), and femoral artery (left/right). Indwelling catheters/sheaths were placed to access the preferred blood vessel and were secured in place for the duration of the blood collection period. All procedures were performed by trained staff per approved protocols and SOPs at the Testing Facilities. A 5-mL blank blood collection was obtained from each animal prior to the first dosing. One-mL blood samples were collected up to 5 hours after patch application dosing. Heparinized microtainer tubes were used to collect all blood samples. Blood volume drawn was replaced with equal volume of heparinized saline with catheter's dead volume accounted. In general, blood collection on a daily basis did not exceed 3-5% of the animal's total blood volume.

Intravenous Dosing of Zolmitriptan

Zolmitriptan solution for IV dosing was prepared in-house with maximum zolmitriptan concentration of 3 mg/mL. Less than 3 mL of dosing volume was injected using a 28-30 G needle into a marginal ear vein of the animal. Pressure was applied momentarily with gauze immediately after injection to prevent bleeding at the site of injection.

Determination of Patch Delivery Performance

ZP-Zolmitriptan Delivery Determination Using Residual Drug Analysis

Zolmitriptan residual was determined from the used patch and swabbing from the treated skin site. Once peeled off the skin, the used patches were trimmed of the adhesive band outside the microprojection array area and saved for zolmitriptan residual analysis. To recover residual zolmitriptan from the treated skin site, three synthetic fiber swabs were used. The first swab was pre-wetted by insertion into a vial containing 1 mL of swab buffer. The first swab was applied over the patch treatment skin site with slight pressure (using rolling motion) in several directions and up to the periphery of the treatment site. The second and third swabs were dry and were used to capture all residual buffer from the skin site that was wetted by the first swab. All three swabs were placed in the original vial containing the swab buffer. The amounts of zolmitriptan left on the microprojection array and skin surface after each application were compared against the original coated amounts on the array, allowing for the determinations of total zolmitriptan Delivery and Delivery Efficiency. Equations to determine the total drug delivered and drug delivery efficiency are shown below as (1) and (2) respectively.

$$\text{Total Residual} = \text{Patch Residual} + \text{Skin Residual}$$

$$\text{Total Drug Delivered} = \text{Nominal Coated amount} - \text{Total Residual} \quad (1)$$

$$\text{Delivery Efficiency}(\%) = \left(\frac{(1)}{\text{Nominal Coated amount}}\right) * 100 \quad (2)$$

Study Design

Three prepubescent female Yorkshire swine were used in the studies. Naïve animals were purchased from approved vendors per Test Facilities' approved protocol and SOPs and quarantined for up to 7 days. Each group of animals was dosed up to 5 treatments (crossover) with a recovery/washout period of up to 5 days between treatments. At first dosing, animals had weight ranging from 18-25 kg and at last dosing, animals had weights ranging from 25-41 kg. In general, treatments per group included one to two controls and one to three ZP-Zolmitriptan dosing. Control included IV zolmitriptan. ZP-Zolmitriptan patch placement was rotated from the left and right ventral thighs of the hind limbs in each group of animals where more than one patch application treatments were conducted.

Results

TABLE 31

In vivo Zolmitriptan patch delivery results

| Coated amount (mg) (SD) | 1.89 (0.14) | 2.02 ± 0.0.6 |
|---|---|---|
| Mean Delivered amount (mg) (SD) | 1.72 (0.05) | 1.79 (0.12) |
| Mean Delivery Efficiency (%) | 90.4 | 88.7 |
| % CV | 3 | 7 |
| Min amount delivered (mg) | 1.68 | 1.68 |
| Max amount delivered (mg) | 1.78 | 1.92 |
| N | 3 | 3 |

Mean delivery was >1.7 mg for all coated both in vivo studies. Delivery efficiency were >85% and were consistent for both studies. Pharmacokinetic study was subsequently conducted with MF1663 array design coated with 1.9 mg. Table 32 summarizes the patch and IV results.

TABLE 32

PK parameters of zolmitriptan patch in animal studies

| PK parameters | IV | ZP-Zolmitriptan |
|---|---|---|
| Patch Coated Dose (mg) | N/A | 1.95 |
| Dose (mg/Kg) | 0.074 | 0.061 |
| $C_{max}$ (ng/mL) (Mean ± SE) | 251.7 ± 11.4 | 8.4 ± 1.7 |
| Median $T_{max}$ (min) | 1 | 15 (10-30) |
| $AUC_t$ (ng × h/mL) (Mean ± SE) | 27.4 ± 1.9 | 16.8 ± 1.5 |
| Absolute Bioavailability (%) (Mean ± SE) | N/A | 76.9 ± 8.2 |

In vivo evaluation showed rapid systemic absorption of zolmitriptan with patch administration. Plasma levels were maintained over 5 h with median $T_{max}$ of 15 minutes. Zolmitriptan patches had an absolute bioavailability of 77%. ZP-Zolmitriptan patch showed that the requisite amount of drug could be coated, high delivery efficiency consistently attained and coated zolmitriptan was well absorbed with fast time to $C_{max}$.

The study was repeated with a larger population of swine. Five animals were treated with adhesive dermally-applied microarray (ADAM) zolmitriptan and 9 were administered with IV zolmitriptan. An additional group of swine were tested with noncoated ADAM. The ADAM treatments were applied using a hand-held reusable applicator (total energy=0.26 Joules). The ADAM patches were worn for an hour. The IV zolmitriptan was applied at a dose of 0.074 mg/kg body weight.

The microprojections for the ADAM microarray was 340 µm long. The depth of penetration ("DOP") was measured for the microprojection penetration sites. The mean DOP for ADAM zolmitriptan measured at 105.4±3.6 µm and for noncoated ADAM was 123.9 4±4.8 µm. The DOP data indicated that most microprojections penetrated about 50% or less of their length and that DOP was reduced by approximately 15% in zolmitriptan-coated microprojections relative to the noncoated ones. About 96.2% of the ADAM zolmitriptan-coated microprojections penetrated the dermis, and about 11.4% of the DOP measurements showed penetrations deeper than 150 µm—none beyond 300 µm. Epidermal-dermal junctions begin at 60 µm below the skin surface.

The ADAM Zolmitriptan application had a high efficiency despite the DOP data indicating a depth of less than 50% of the microneedle's length. Mean residues on the worn ADAM were 10%, and on the treated skin sites after ADAM removal they were 5%. The bioavailability was 77%. The median $T_{max}$ for an ADAM Zolmitriptan of 1.9 mg was 15 minutes. Systematic zolmitriptan was detectable to the last sampling time point at 5 hours for ADAM Zolmitriptan and at 3 hours for IV Zolmitriptan.

| PK Parameter | IV | Zolmitriptan ADAM |
|---|---|---|
| Dose (mg/kg) | 0.074 ± 0.001 | 0.060 ± 0.004 |
| $AUC_{0-t}$, ng * h/mL | 27.4 ± 1.9 | 16.8 ± 1.5 |
| $C_{max}$ | 251.7 ± 11.4 | 8.4 ± 1.7 |
| $T_{max}$ | — | 15 (15-60) |
| F (absolute bioavailability), % | — | 77.3 ± 9.0 |
| Delivery efficiency | — | 85 ± 1.7 |

The bioavailability along with the DOP data indicates that with ADAM administration, 105 µm penetration depth (from the stratum corneum into the dermis) may be sufficient to achieve optimal therapeutic outcome. In addition, ADAM intracutaneous delivery may circumvent first-pass metabolism. A preliminary analysis of the plasma PK samples for n-desmethyl metabolite indicated an average of 6.5% conversion from the parent compound.

After a 1-hour wear, zolmitriptan delivery was efficient, with only 15% of residual zolmitriptan on the skin and patch after removal. Evidence of zolmitriptan diffusion within the skin was obtained by quantitative mass-spectrometry imaging. The zolmitriptan distribution is shown in the table below. Analyses of the surface area of the stratum corneum, epidermis, and dermis indicate that the largest amount of zolmitriptan localized to the dermis. This suggests that most of the absorbed zolmitriptan had diffused past the epidermis into the dermal/hypodermal capillary bed, as indicated by $C_{max}$, within the 1 hour of ADAM Zolmitriptan wear.

| Skin Layers | Percentage of Total Surface Area | Percentage of Total Zolmitriptan |
|---|---|---|
| Stratum corneum | 1.2 | 1.8 |
| Epidermis | 3.8 | 2.7 |
| Dermis/hypodermis | 95.0 | 95.5 |

Example 7—Human Efficacy Clinical Trial

The ZOTRIP pivotal efficacy study was a multicenter, double-blind, randomized, placebo-controlled trial comparing three doses of M207 (1.0 mg, 1.9 mg, and 3.8 mg) to placebo for the treatment of a single migraine attack. Subjects were enrolled in the ZOTRIP trial at 36 centers across the United States. Those recruited into the trial had a history of at least one year of migraine episodes with or without aura. Upon recruitment, the subjects entered a run-in period that ensured they met the key eligibility criteria of 2-8 migraine attacks per month, which was documented using an electronic diary or an app on their cell phone. Subjects also identified their most bothersome other symptom selected from nausea, photophobia, and phonophobia, and indicated the presence or absence of nausea, phonophobia or photophobia, during the episodes in the run-in period. Successfully screened subjects were then randomized into the treatment/dosing period in which they had 8 weeks to confirm and receive blinded treatment for a single migraine attack, termed "qualifying migraine," in which their previously identified most bothersome other symptom had to be present.

During a qualifying migraine, subjects scored the severity of pain on the 4-point headache pain scale, and the presence or absence of migraine associated symptoms (photophobia, phonophobia or nausea), starting pre-dose and then at several intervals over 48 hours post-dose. The co-primary endpoints for the study were those defined in the October 2014 FDA Draft Guidance—"*Migraine: Developing Drugs for Acute Treatment*" on pain and most bothersome other symptom freedom. Subjects recorded their migraine symptoms in a patient diary, prior to treatment, and at varying intervals following treatment, out to 48 hours. Safety was assessed by adverse events reported and other standard safety measures.

Five hundred and eighty nine (589) subjects were enrolled in this study, of which 365 were randomized. Of those randomized, 333 subjects were treated and were included in the safety analysis, and 321 qualified for the modified intent-to-treat (mITT) population. Fifty-one percent (51%) of the subjects randomized were found to have severe migraine pain pre-treatment. Also at the time of treatment, 70% reported nausea, 37% aura, and 51% waking up with their migraine (morning migraine). With the multiple doses and multiple endpoints in the trial, a sequential testing procedure was used beginning with the highest dose and the co-primary endpoints. Since statistical significance was not achieved for most bothersome other symptom in the 1.9 mg group, p-values for secondary endpoints should be considered nominal p-values.

All three doses of M207 (1 mg, 1.9 mg, and 3.8 mg) achieved statistically significant pain freedom at 2 hours. The 3.8 mg dose achieved both co-primary endpoints of pain freedom and most bothersome other symptom freedom at 2 hours. The 3.8 mg dose also achieved significance in the secondary endpoints of pain freedom at 45 minutes and 1 hour and showed durability of effect on pain freedom at 24 and 48 hours. Additionally, M207 was not associated with any Serious Adverse Events (SAEs).

The 3.8 mg dose of M207 achieved statistical significance for both co-primary endpoints at two hours, as shown in Table 33:

TABLE 33

| Primary Endpoint | | | |
|---|---|---|---|
| Primary endpoint | Placebo | 3.8 mg M207 | p-value |
| Pain freedom | 14.3% | 41.5% | 0.0001 |
| Most bothersome other symptom free | 42.9% | 68.3% | 0.0009 |

Furthermore, secondary endpoints measuring pain freedom at additional time points for the 3.8 mg dose of M207 showed M207 superior to placebo with a nominal p-value less than 0.05, as shown in Table 34:

TABLE 34

| Pain Freedom | | | |
|---|---|---|---|
| Pain Freedom | Placebo | 3.8 mg M207 | p-value* |
| Pain freedom at 45 minutes | 5.2% | 17.1% | 0.0175 |
| Pain freedom at 60 minutes | 10.4% | 26.8% | 0.0084 |
| Pain freedom at 24 hours | 39.0% | 69.5% | 0.0001 |
| Pain freedom at 48 hours | 39.0% | 64.6% | 0.0013 |

Overall, only 13 subjects (3.9%) reported pain at the application site; application site pain was reported as mild in all but three subjects. The most frequently reported adverse event was redness at the application site (18.3% of subjects). All cases of redness resolved. Further, five (1.5%) patients across M207-treated groups reported dizziness vs. 0% on placebo.

Additional data from the results of the clinical trial are set forth in the Tables below.

TABLE 35

| Co-Primary Endpoints: Primary Endpoint Analysis | | | | |
|---|---|---|---|---|
| | Treatment Group | | | |
| mITT Population (LOCF) | Placebo (N = 77) | 1 mg (N = 79) | 1.9 mg (N = 83) | 3.8 mg (N = 82) |
| Pain Freedom at 2 hours | | | | |
| % (n/N) | 14.3% (11/77) | 30.4% (24/79) | 27.7% (23/83) | 41.5% (34/82) |
| Difference from Placebo | | 16.1% | 13.4% | 27.2% |
| P-value | | 0.0149 | 0.0351 | 0.0001 |
| Freedom from most bothersome other symptom at 2 hours | | | | |
| % (n/N) | 42.9% (33/77) | 57.0% (45/79) | 53.0% (44/83) | 68.3% (56/82) |
| Difference from Placebo | | 14.1% | 10.2% | 25.4% |
| P-value | | 0.0706 | 0.1694 | 0.0009 |

In Table 35, above, the 3.8 mg dose group met both co-primary endpoints with a p-value <0.05. The 1.9 mg dose group met the pain freedom endpoint with a p-value <0.05. For the freedom from most bothersome other symptom at 2 hours endpoint, the 1.9 mg dose group had a p-value of ≥0.05. The 1 mg dose group met the pain freedom endpoint with a p-value <0.05. For the 1 mg dose group, the freedom from most bothersome other symptom endpoint at 2 hours had a p-value ≥0.05.

TABLE 36

Co-Primary Endpoints: Multiple Imputation

| mITT Population (LOCF) | Treatment Group | | | |
|---|---|---|---|---|
| | Placebo (N = 77) | 1 mg (N = 79) | 1.9 mg (N = 83) | 3.8 mg (N = 82) |
| Pain Freedom at 2 hours | | | | |
| Average % | 14.7% | 29.8% | 29.4% | 39.8% |
| Difference from Placebo | | 15.1% | 14.7% | 25.1% |
| P-value | | 0.0297 | 0.0344 | 0.0012 |
| Freedom from most othersome other symptom at 2 hours | | | | |
| % (n/N) | 42.6% | 59.9% | 56.5% | 68.2% |
| Difference from Placebo | | 17.3% | 13.9% | 25.6% |
| P-value | | 0.0294 | 0.0755 | 0.0013 |

Table 36, above, is consistent with co-primary endpoint analyses (mITT LOCF). Table 35, below, provides the fixed-sequence for testing each of the multiple endpoints that are described for migraines to assess whether the study was successful. For doses of 3.8 mg, 1.9 mg, and 1.0 mg, the efficacy of treatment was tested for the co-primary and secondary endpoints in Table 35. As shown, all endpoints at or after testing order 4 are not significant under the MCP methodology.

TABLE 37

CP2016-001: MCP - Fixed Sequential Testing

| Testing Order | Co-Primary/ Secondary | Efficacy Endpoint | Dose | P-value | Statistically significant Under MCP |
|---|---|---|---|---|---|
| 1 | co-primary | Pain free at 2 hours | 3.8 mg | 0.0001 | Yes |
| 2 | co-primary | Most bothersome other symptom free at 2 hours | 3.8 mg | 0.0009 | Yes |
| 3 | co-primary | Pain free at 2 hours | 1.9 mg | 0.0351 | Yes |
| 4 | co-primary | Most bothersome other symptom free at 2 hours | 1.9 mg | 0.1694 | No |
| 5 | secondary | Pain relief at 30 minutes | 3.8 mg | 0.1024 | No |
| 6 | secondary | Pain relief at 30 minutes | 1.9 mg | 0.8642 | No |
| 7 | secondary | Pain relief at 2 hours | 3.8 mg | 0.0013 | No |
| 8 | secondary | Pain relief at 2 hours | 1.9 mg | 0.1109 | No |
| 9 | co-primary | Pain free at 2 hours | 1.0 mg | 0.0149 | No |
| 10 | co-primary | Most bothersome other symptom free at 2 hours | 1.0 mg | 0.0706 | No |
| 11 | secondary | Pain relief at 30 minutes | 1.0 mg | 0.7839 | No |

Tables 38-46 provide results of a clinical study of treating with one embodiment of the claimed invention. In this embodiment, as shown in Tables 36-40, endpoints were evaluated sequentially, as described in Table 35, including pain freedom, pain relief, photophobia freedom, phonophobia freedom, and nausea freedom for treatment of 1 mg, 1.9 mg, and 3.8 mg at time points of 15 minutes, 30 minutes, 45 minutes, 1 hour, 2 hours, 3 hours, 4 hours, 12 hours, 24 hours, and 48 hours after treatment. As shown in Tables 41-44, investigators also made visual assessments of the skin after patch removal for adverse events like bruising, edema, and erythema.

TABLE 38

Pain Freedom

| | Pain Freedom (mITT/LOCF) Treatment Group | | | |
|---|---|---|---|---|
| Time-point | Placebo | 1 mg | 1.9 mg | 3.8 mg |
| 15 Minutes | 0% | 0% | 0% | 0% |
| 30 minutes | 2.6% | 2.5% | 3.6% | 7.3% |
| 45 minutes | 5.2% | 3.8% | 13.3% | 17.1%* |
| 1 hour | 10.4% | 17.7% | 20.5% | 26.8%* |
| 2 hour | 14.3% | 30.4%* | 27.7%* | 41.5%* |
| 3 hour | 26.0% | 40.5%* | 37.3% | 51.2%* |
| 4 hour | 28.6% | 45.6%* | 47.0%* | 54.9%* |
| 12 hours | 32.5% | 54.4%* | 53.0%* | 62.2%* |
| 24 hours | 39.0% | 59.5%* | 61.4%* | 69.5%* |
| 48 hours | 39.0% | 63.3%* | 66.3%* | 64.6%* |

*Indicates p-value < 0.05 however not significant under MCP

TABLE 39

Pain Relief

| Pain Relief (mITT/LOCF) | Treatment Group | | | |
|---|---|---|---|---|
| Time-point | Placebo | 1 mg | 1.9 mg | 3.8 mg |
| 15 Minutes | 14.3% | 12.7% | 16.9% | 23.2% |
| 30 minutes | 33.8% | 31.6% | 32.5% | 46.3% |

TABLE 39-continued

Pain Relief

| Pain Relief (mITT/LOCF) | Treatment Group | | | |
|---|---|---|---|---|
| Time-point | Placebo | 1 mg | 1.9 mg | 3.8 mg |
| 45 minutes | 45.5% | 44.3% | 45.8% | 56.1% |
| 1 hour | 53.2% | 46.8% | 55.4% | 68.3%* |
| 2 hour | 57.1% | 65.8% | 68.7% | 80.5%* |
| 3 hour | 51.9% | 75.9%* | 66.3% | 81.7%* |
| 4 hour | 51.9% | 73.4%* | 72.3%* | 82.9%* |
| 12 hours | 48.1% | 75.9%* | 72.3%* | 80.5%* |
| 24 hours | 46.8% | 72.2%* | 72.3%* | 78.0%* |
| 48 hours | 41.6% | 72.2%* | 71.1%* | 70.7%* |

*Indicates p-value < 0.05; however not significant under MCP

TABLE 40

Photophobia Freedom

| Pain Freedom (mITT/LOCF) | Treatment Group | | | |
|---|---|---|---|---|
| Time-point | Placebo | 1 mg | 1.9 mg | 3.8 mg |
| 15 Minutes | 9.1% | 11.4% | 9.6% | 11.0% |
| 30 minutes | 22.1% | 27.8% | 24.1% | 26.8% |
| 45 minutes | 24.7% | 43.0%* | 33.7% | 41.5%* |
| 1 hour | 33.8% | 48.1%* | 44.6% | 53.7%* |
| 2 hour | 41.6% | 60.8%* | 56.6%* | 69.5%* |
| 3 hour | 44.2% | 65.8%* | 61.4%* | 72.0%* |
| 4 hour | 45.5% | 65.8%* | 63.9%* | 74.4%* |
| 12 hours | 42.9% | 74.7%* | 66.3%* | 75.6%* |
| 24 hours | 42.9% | 72.2%* | 68.7%* | 73.2%* |
| 48 hours | 40.3% | 70.9%* | 67.5%* | 68.3%* |

*Indicates p-value < 0.05; however not significant under MCP

TABLE 41

Phonophobia Freedom

| Pain Freedom (mITT/LOCF) | Treatment Group | | | |
|---|---|---|---|---|
| Time-point | Placebo | 1 mg | 1.9 mg | 3.8 mg |
| 15 Minutes | 14.3% | 20.3% | 15.7% | 25.6% |
| 30 minutes | 35.1% | 34.2% | 28.9% | 45.1% |
| 45 minutes | 37.7% | 44.3% | 43.4% | 57.3%* |
| 1 hour | 46.8% | 48.1% | 57.8% | 61.0% |
| 2 hour | 55.8% | 58.2% | 61.4% | 69.5% |
| 3 hour | 54.5% | 63.3% | 71.1%* | 73.2%* |
| 4 hour | 57.1% | 69.6% | 69.9% | 74.4%* |
| 12 hours | 44.2% | 73.4%* | 68.7%* | 78.0%* |
| 24 hours | 42.9% | 69.6%* | 68.7%* | 76.8%* |
| 48 hours | 42.9% | 72.2%* | 68.7%* | 70.7%* |

*Indicates p-value < 0.05; however not significant under MCP

TABLE 42

Nausea Freedom

| Nausea Freedom (mITT/LOCF) | Treatment Group | | | |
|---|---|---|---|---|
| Time-point | Placebo | 1 mg | 1.9 mg | 3.8 mg |
| 15 Minutes | 36.4% | 39.2% | 41.0% | 32.9% |
| 30 minutes | 59.7% | 55.7% | 49.4% | 53.7% |
| 45 minutes | 63.6% | 58.2% | 66.3% | 62.2% |
| 1 hour | 63.6% | 68.4% | 71.1% | 76.8% |

TABLE 42-continued

Nausea Freedom

| Nausea Freedom (mITT/LOCF) | Treatment Group | | | |
|---|---|---|---|---|
| Time-point | Placebo | 1 mg | 1.9 mg | 3.8 mg |
| 2 hour | 63.6% | 75.9% | 74.7% | 81.7%* |
| 3 hour | 58.4% | 78.5%* | 74.7%* | 79.3%* |
| 4 hour | 54.5% | 78.5%* | 73.5%* | 79.3%* |
| 12 hours | 45.5% | 75.9%* | 71.1%* | 80.5%* |
| 24 hours | 44.2% | 72.2%* | 74.7%* | 79.3%* |
| 48 hours | 41.6% | 72.2%* | 72.3%* | 70.7%* |

*Indicates p-value < 0.05; however not significant under MCP

TABLE 43

Investigator: Visual Dermal Assessment: PRSPB

| Patch-Related Superficial Punctate Bruising (PRSPB) | Treatment Group | | | |
|---|---|---|---|---|
| | Placebo (N = 83) | 1 mg (N = 78) | 1.9 mg (N = 84) | 3.8 mg (N = 83) |
| None | 82 (98.8%) | 73 (93.6%) | 72 (85.7%) | 74 (89.2%) |
| <=25% ZP patch application site has punctate bruising spots | 1 (1.2%) | 5 (6.4%) | 9 (10.7%) | 4 (4.8%) |
| >=26% to <50% ZP patch application site has punctate bruising spots | 0 (0.0%) | 0 (0.0%) | 2 (2.4%) | 2 (2.4%) |
| >50% ZP patch application site has punctate bruising spots | 0 (0.0%) | 0 (0.0%) | 1 (1.2%) | 3 (3.6%) |

Note:
Investigator assessment occurs at End-of Study;
Day 2-8 (treatment on Day 1)

TABLE 44

Investigator: Visual Dermal Assessment: Edema

| Edema | Treatment Group | | | |
|---|---|---|---|---|
| | Placebo (N = 83) | 1 mg (N = 78) | 1.9 mg (N = 84) | 3.8 mg (N = 83) |
| None | 83 (100.0%) | 77 (98.7%) | 81 (96.4%) | 82 (98.8%) |
| Slight Edema | 0 (0.0%) | 1 (1.3%) | 3 (3.6%) | 1 (1.2%) |
| Moderate Edema | 0 (0.0%) | 0 (0.0%) | 0 (0.0%) | 0 (0.0%) |
| Severe Edema | 0 (0.0%) | 0 (0.0%) | 0 (0.0%) | 0 (0.0%) |

Note:
Investigator assessment occurs at Visit 4;
End-of Study

TABLE 45

Investigator: Visual Dermal Assessment: Erythema

| Erythema | Treatment Group | | | |
|---|---|---|---|---|
| | Placebo (N = 83) | 1 mg (N = 78) | 1.9 mg (N = 84) | 3.8 mg (N = 83) |
| None | 78 (94.0%) | 71 (91.0%) | 71 (84.5%) | 64 (77.1%) |
| Mild Redness | 5 (6.0%) | 7 (9.0%) | 10 (11.9%) | 16 (19.3%) |

TABLE 45-continued

Investigator: Visual Dermal Assessment: Erythema

| Erythema | Placebo (N = 83) | 1 mg (N = 78) | 1.9 mg (N = 84) | 3.8 mg (N = 83) |
|---|---|---|---|---|
| Well-defined Redness | 0 (0.0%) | 0 (0.0%) | 3 (3.6%) | 3 (3.6%) |
| Beet Redness | 0 (0.0%) | 0 (0.0%) | 0 (0.0%) | 0 (0.0%) |

Note:
Investigator assessment occurs at Visit 4;
End-of Study

TABLE 46

General Disorders/Administration Disorders TEAEs

| System Organ Class/Preferred Term N (%) of Subjects | Placebo | 1 mg | 1.9 mg | 3.8 mg |
|---|---|---|---|---|
| General disorders and administration site conditions | 12 (14.5%) | 23 (28.8%) | 31 (35.6%) | 38 (45.8%) |
| Application site erythema | 9 (10.8%) | 13 (16.3%) | 17 (19.5%) | 22 (26.5%) |
| Application site bruise | 3 (3.6%) | 5 (6.3%) | 12 (13.8%) | 12 (14.5%) |
| Application site pain | 1 (1.2%) | 2 (2.5%) | 2 (2.3%) | 8 (9.6%) |
| Application site hemorrhage | 0 (0.0%) | 3 (3.8%) | 5 (5.7%) | 4 (4.8%) |
| Application site swelling | 3 (3.6%) | 1 (1.3%) | 3 (3.4%) | 2 (2.4%) |
| Application site edema | 0 (0.0%) | 1 (1.3%) | 3 (3.4%) | 2 (2.4%) |
| Application site discoloration | 1 (1.2%) | 1 (1.3%) | 1 (1.1%) | 1 (1.2%) |

Note:
TEAEs occurring in >1 active treated subject

Tables 47-50 and FIGS. 25-28 demonstrate the efficacy of one embodiment of the claimed invention against published results of treatments that are currently used in the art. Until the claimed invention, the state of the art included nasal treatments and standard and orally dissolving tablets.

TABLE 47

Pain Free Zolmitriptan
ZOLMITRIPTAN COMPARISON, % PAIN FREE

| Dosage Form | Dose | 1 hour | 2 hour | 4 hour | Reference |
|---|---|---|---|---|---|
| M207 Patch | 3.8 mg | 26.8% | 41.5% | 54.9% | |
| M207 Patch | 1.9 mg | 20.5% | 27.7% | 47.0% | |
| M207 Patch | 1.0 mg | 17.7% | 30.4% | 45.6% | |
| NASAL | 2.5 mg | 10.6% | 21.0% | 38.4% | Charlesworth et al, 2003 |
| TABLET | 2.5 mg | 10.4% | 35.6% | | Pascual et al, 2000 |
| TABLET | 5 mg | 10.0% | 39.0% | | Dahlof et al 1998 |
| TABLET | 10 mg | 9.0% | 39.0% | | Dahlof et al 1998 |
| ODT | 2.5 mg | 7.8% | 27.0% | 37.0% | Dowson et al, 2002 |
| TABLET | 5 mg | 7.8% | 29.3% | 54.6% | Geraud et al, 2000 |
| TABLET | 2.5 mg | 5.7% | 26.3% | | Steiner et al, 2003 |

TABLE 48

Pain Relief Zolmitriptan
ZOLMITRIPTAN COMPARISON, % PAIN RELIEF

| Dosage Form | Dose | 1 hour | 2 hour | 4 hour | Reference |
|---|---|---|---|---|---|
| M207 Patch | 3.8 mg | 68.3% | 80.5% | 82.9% | |
| M207 Patch | 1.9 mg | 55.4% | 68.7% | 72.3% | |
| M207 Patch | 1.0 mg | 46.8% | 65.8% | 73.4% | |
| ODT | 2.5 mg | 45.0% | 63.0% | | Dowson et al, 2002 |
| TABLET | 5 mg | 44.0% | 66.0% | | Dahlof et al 1998 |
| NASAL | 2.5 mg | 40.2% | 55.4% | 63.4% | Charlesworth et al, 2003 |
| TABLET | 10 mg | 40.0% | 71.0% | | Dahlof et al 1998 |
| TABLET | 2.5 mg | 35.3% | 66.8% | | Pascual et al, 2000 |
| TABLET | 5 mg | 34.2% | 58.7% | 80.5% | Geraud et al, 2000 |
| TABLET | 2.5 mg | 25.1% | 59.6% | 25.1% | Steiner et al, 2003 |

TABLE 49

Pain Free Triptans
COMPARISON TO OTHER TRIPTANS, % PAIN FREE

| Drug | Dosage Form | Dose | 1 hour | 2 hour | 4 hour | Reference |
|---|---|---|---|---|---|---|
| Zolmitriptan | ZSAN Patch | 3.8 mg | 26.8% | 41.5% | 54.9% | |
| Zolmitriptan | ZSAN Patch | 1.9 mg | 20.5% | 27.7% | 47.0% | |
| Zolmitriptan | ZSAN Patch | 1.0 mg | 17.7% | 30.4% | 45.6% | |
| Rizatriptan | WAFER | 10 mg | 13.0% | 42.2% | | Ahrens et al, 1999 |
| Zolmitriptan | NASAL | 2.5 mg | 10.6% | 21.0% | 38.4% | Charlesworth et al, 2003 |

TABLE 49-continued

Pain Free Triptans
COMPARISON TO OTHER TRIPTANS, % PAIN FREE

| Drug | Dosage Form | Dose | 1 hour | 2 hour | 4 hour | Reference |
|---|---|---|---|---|---|---|
| Rizatriptan | TABLET | 10 mg | 10.4% | 40.3% | | Tfelt-Hansen et al, 1998 |
| Eletriptan | TABLET | 80 mg | 10.0% | 27.0% | 49.0% | Sheftell et al 2003 |
| Zolmitriptan | ODT | 2.5 mg | 7.8% | 27.0% | 37.0% | Dowson et al, 2002 |
| Zolmitriptan | TABLET | 5 mg | 7.8% | 29.3% | 54.6% | Geraud et al, 2000 |
| Sumatriptan | TABLET | 100 mg | 7.8% | 32.8% | | Tfelt-Hansen et al, 1998 |
| Rizatriptan | WAFER | 5 mg | 7.7% | 34.8% | | Ahrens et al, 1999 |
| Naratriptan | TABLET | 2.5 mg | 3.3% | 20.7% | | Bomhof et al, 1999 |

TABLE 50

Pain Relief Triptans
COMPARISON TO OTHER TRIPTANS, % PAIN RELIEF

| Drug | Dosage Form | Dose | 1 hour | 2 hour | 4 hour | Reference |
|---|---|---|---|---|---|---|
| Zolmitriptan | ZSAN Patch | 3.8 mg | 68.3% | 80.5% | 82.9% | |
| Zolmitriptan | ZSAN Patch | 1.9 mg | 55.4% | 68.7% | 72.3% | |
| Zolmitriptan | ZSAN Patch | 1.0 mg | 46.8% | 65.8% | 73.4% | |
| Zolmitriptan | ODT | 2.5 mg | 45.0% | 63.0% | | Dowson et al, 2002 |
| Rizatriptan | WAFER | 10 mg | 44.9% | 74.1% | | Ahrens et al, 1999 |
| Zolmitriptan | NASAL | 2.5 mg | 40.2% | 55.4% | 63.4% | Charlesworth et al, 2003 |
| Rizatriptan | WAFER | 5 mg | 39.8% | 58.6% | | Ahrens et al, 1999 |
| Rizatriptan | TABLET | 10 mg | 36.6% | 67.0% | | Tfelt-Hansen et al, 1998 |
| Zolmitriptan | TABLET | 5 mg | 34.2% | 58.7% | 80.5% | Geraud et al, 2000 |
| Eletriptan | TABLET | 80 mg | 32.0% | 59.0% | 79.0% | Sheftell et al 2003 |
| Sumatriptan | TABLET | 100 mg | 27.9% | 61.8% | | Tfelt-Hansen et al, 1998 |
| Naratriptan | TABLET | 2.5 mg | 27.7% | 48.4% | | Bomhof et al, 1999 |

The ZOTRIP Phase 2/3 clinical study of ADAM™ zolmitriptan for the acute treatment of migraine achieved statistically significant and clinically meaningful results of primary endpoints which included 41.5% pain freedom at two hours compared to placebo and 68.3% relief of most bother symptom at two hours compared to placebo. 81% of subjects achieved pain relief at two hours and was sustained through 24 hours. The most commonly reported adverse events were application site erythema which generally resolved within 48 hours and bruising.

Example 8—Analysis of Ligand-Receptor Kinetics of Zolmitriptan, its Primary Metabolite, and Sumatriptan The triptans, including zolmitriptan and sumatriptan are cornerstones of acute migraine treatment. Triptans are agonists of serotonin (5-hydroxytryptamine [5-HT]) receptor subtypes $1_B$ and $1_D$ and are thought to exert their therapeutic effect through 5-HT receptor-mediated cranial vessel constriction and inhibition of pro-inflammatory neuropeptide release.

Zolmitriptan's primary metabolite is N-desmethyl zolmitriptan (NDZ), which is purported to have a potency that is two- to six-fold higher than that of zolmitriptan.[1] However, there is a paucity of peer-reviewed literature regarding receptor binding and activity for this molecule.

Figure 33:
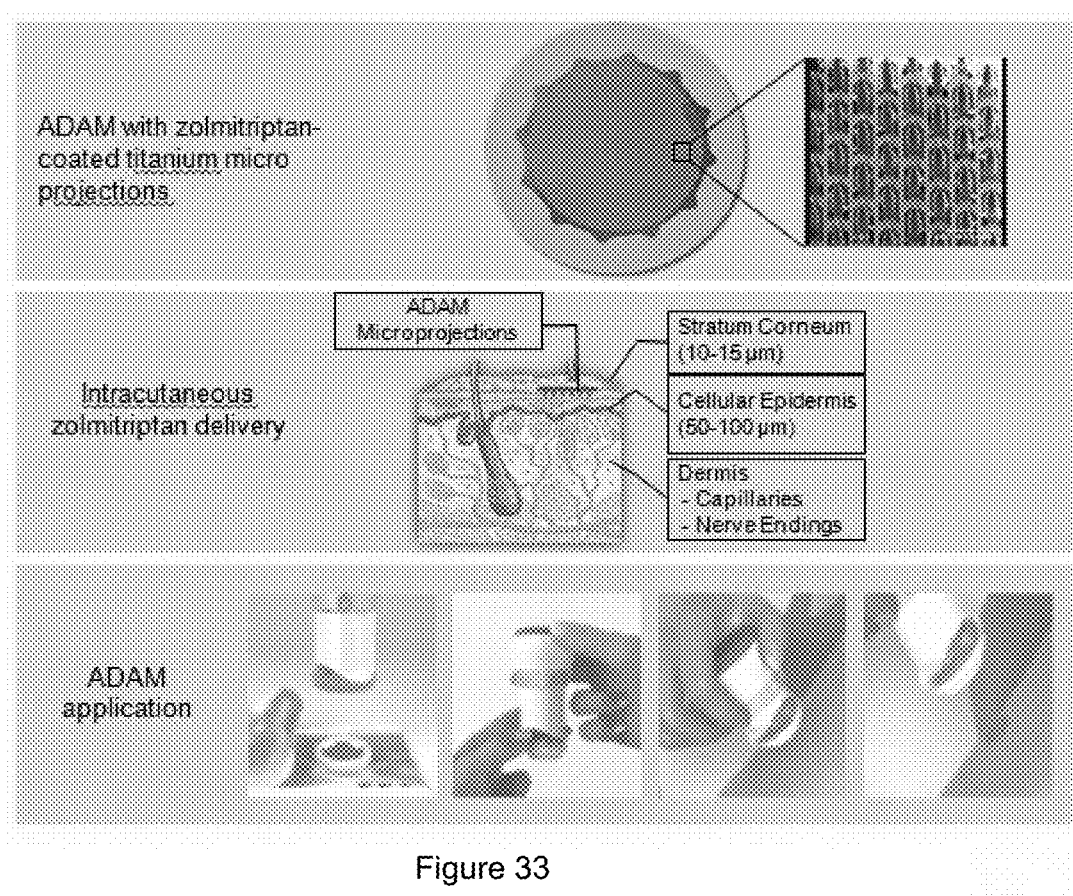
FIG. 33 depicts the ADAM system for intracutaneous zolmitriptan delivery.

ADAM is an investigational system that provides intracutaneous drug administration (FIG. 33).

Figure 34:
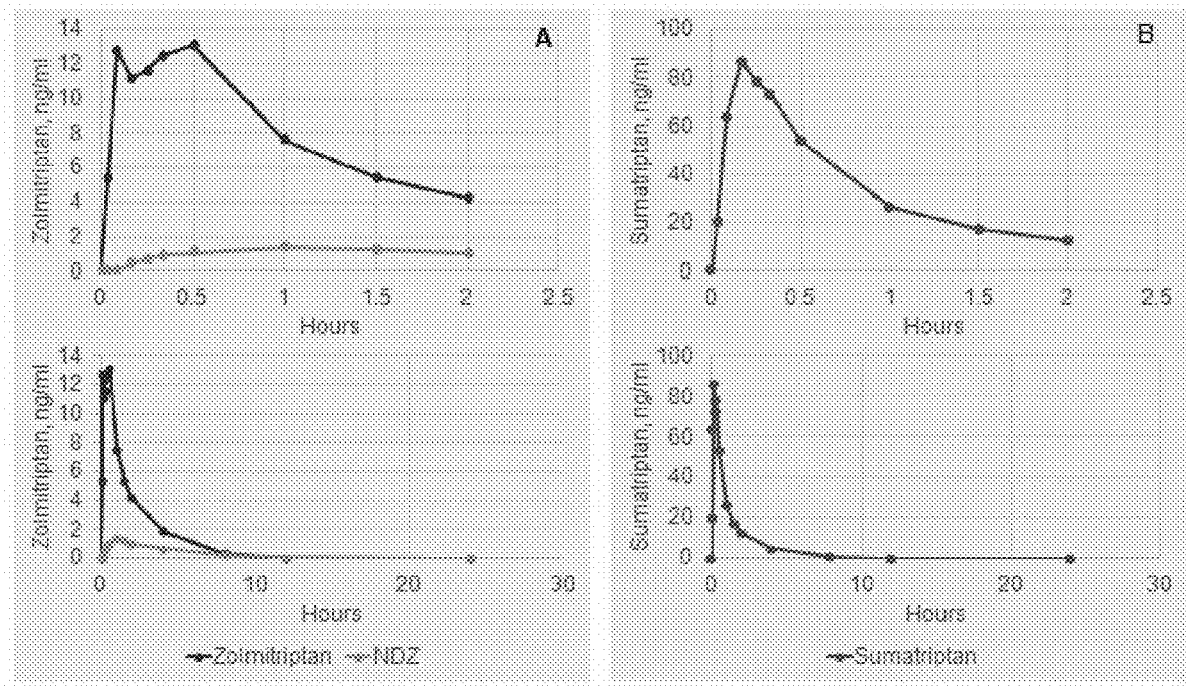
FIG. 34 is a graphic representation of plasma concentration over time of A) zolmitriptan and N-desmethyl zolmitriptan (NDZ) following delivery using ADAM zolmitriptan 2×1.9 mg, and B) sumatriptan following subcutaneous injection 6.0 mg/0.5 ml.

A previously published phase 1 study evaluated the pharmacokinetics of orally administered zolmitriptan, zolmitriptan delivered with ADAM, and subcutaneously administered sumatriptan. Absorption was considerably faster for intracutaneous zolmitriptan, and subcutaneous sumatriptan, than for oral zolmitriptan, with higher exposure in the first two hours[2] (Table 51, FIG. 34).

TABLE 51

| Plasma Pharmacokinetic Parameters* | | | | | |
|---|---|---|---|---|---|
| | $t_{max}$ (min) Median (Range) | $t_{1/2}$ (h) Mean (SD) | $C_{max}$ (ng/mL) Mean (SD) | $AUC_{inf}$ (ng·h/mL) Mean (SD) | $AUC_{2\ hrs}$ (ng·h/mL) Mean (SD) |
| ADAM Zolmitriptan 2 × 1.9 mg | | | | | |
| Zolmitriptan | 18 (2-30) | 1.53 (0.3) | 14.61 (4.5) | 30.12 (10.1) | 16.44 (5.3) |
| N-desmethyl zolmitriptan | 60 (30-90) | 2.82 (0.5) | 1.41 (0.5) | 7.21 (2.3) | 2.15 (0.7) |
| Zolmitriptan tablet 2.5 mg | | | | | |
| Zolmitriptan | 60 (30-240) | 3.27 (0.8)[a] | 3.77 (1.5)[b] | 27.19 (11.3)[a] | 4.72 (2.2)[b] |
| N-desmethyl zolmitriptan | 120 (60-240)[b] | 3.22 (1.1)[b] | 2.08 (0.5)[b] | 14.55 (3.1)[b] | 2.31 (0.9)[b] |

TABLE 51-continued

| | Plasma Pharmacokinetic Parameters* | | | | |
|---|---|---|---|---|---|
| | $t_{max}$ (min) Median (Range) | $t_{1/2}$ (h) Mean (SD) | $C_{max}$ (ng/mL) Mean (SD) | $AUC_{inf}$ (ng · h/mL) Mean (SD) | $AUC_{2\ hrs}$ (ng · h/mL) Mean (SD) |
| Sumatriptan succinate 6.0 mg/0.5 mL for subcutaneous injection | | | | | |
| Sumatriptan | 10 (5-20) | 1.14 (0.3) | 88.80 (27.6) | 105.23 (23.1) | 70.88 (14.15) |

*Note that ADAM zolmitriptan was also tested at doses of 0.48 mg, 0.96 mg, and 1.9 mg. Results are shown here only for the 2 × 1.9 mg dose, which met primary endpoints in the pivotal efficacy and safety trial.[3]

AUC, area under the concentration-time curve. $C_{max}$, peak plasma concentration. ND, not determined. SD, standard deviation. $t_{1/2}$, half life. $t_{max}$, time to reach $C_{max}$. [a]n=19, [b]n=18

In a pivotal phase 2b/3 trial, ADAM zolmitriptan provided significantly higher rates of pain-freedom and freedom from most bothersome other symptom compared with placebo in patients with moderate to severe acute migraine.[3] Pain relief and pain freedom were both rapid and sustained.[3,4]

Among those who were pain-free at 2 hours post-dose, 24% of those receiving ADAM zolmitriptan 3.8 mg and 27% of those receiving placebo had migraine recurrence within 24 hours (P=NS).

In a different trial, 24-hour recurrence rates among those who achieved headache resolution were 38% and 18% in those receiving sumatriptan 6 mg and placebo, respectively (P<0.02).[5]

Additional data concerning sustained pain relief in this trial are presented at this meting.[4]

In this study we investigate the binding parameters for zolmitriptan, NDZ, and sumatriptan to human 5-$HT_{1B}$ and 5-$HT_{1D}$ receptors and explore how these factors might influence the human pharmacokinetics and pharmacodynamics of these molecules, particularly as they pertain to onset and duration of effect.

Methods

Membrane preparations were derived from transfected CHO-K1 cells expressing recombinant human 5-$HT_{1B}$ and 5-$HT_{1D}$ receptors. Binding of test compounds (zolmitriptan, NDZ, sumatriptan) to the membrane preparations was evaluated in duplicate in the presence of 0.6 nM $^3$H-5-carboxamidotryptamine maleate. After incubating for various lengths of time, membranes were washed by filtration and residual $^3$H counts were determined on a microplate scintillation counter. On-rate constant ($k_{on}$), off-rate constant ($k_{off}$), and equilibrium dissociation constant ($K_D$) were determined using nonlinear regression on Prism 4 (GraphPad), and Xlfit (IDBM) software. The following formulae were used in calculating additional parameters using previously derived[2] pharmacokinetic data in healthy human volunteers. Residence time for each ligand on 5-$HT_{1B}$ and 5-$HT_{1D}$ receptors=1/$k_{off}$.

Results a. Ligand Binding Data

The receptor residence time (1/$k_{off}$) was similar for all compounds (~10-20 minutes), and was considerably shorter than the half-life of the molecules. However the $k_{on}$ was 6-10× faster (P<0.05) for zolmitriptan and NDZ than for sumatriptan on both the 5-$HT_{1B}$ and 5 $HT_{1D}$ receptors. Zolmitriptan and NDZ had a considerably higher affinity than sumatriptan for both receptors. 5-$HT1_B$ and $5HT1_D$ receptor binding parameters of zolmitriptan, N-desmethyl zolmitriptan (NDZ), and sumatriptan are presented in Table 52

TABLE 52

5-$HT1_B$ and $5HT1_D$ Receptor Binding Parameters of Zolmitriptan, N-desmethyl Zolmitriptan (NDZ), and Sumatriptan

| | Compound | $k_{on}$ (nM$^{-1}$ min$^{-1}$) | $k_{off}$ (min$^{-1}$) | $K_D$ (nM) |
|---|---|---|---|---|
| 5-$HT_{1B}$ | Zolmitriptan | 0.053 | 0.076 | 1.47 |
| | NDZ | 0.054 | 0.050 | 0.92 |
| | Sumatriptan | 0.008 | 0.052 | 6.38 |
| 5-$HT_{1D}$ | Zolmitriptan | 0.174 | 0.060 | 0.34 |
| | NDZ | 0.126 | 0.054 | 0.43 |
| | Sumatriptan | 0.018 | 0.094 | 5.21 | b. Pharmacokinetic Modeling

Figure 35:
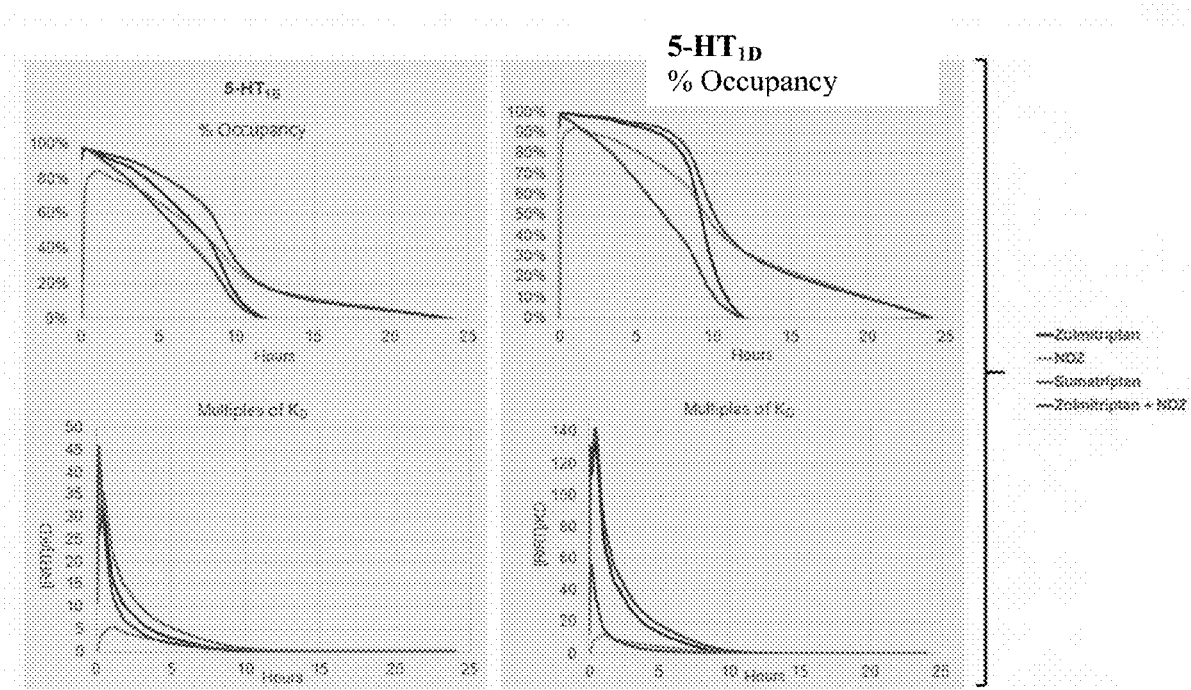
FIG. 35 is a graphic representation of the calculated fractional occupancy of 5-HT$_{1B}$ and 5-HT$_{1D}$ receptors by zolmitriptan, N-desmethyl zolmitriptan (NDZ), and sumatriptan.

The theoretical fractional receptor occupancy of 5-$HT_{1B}$ and 5-$HT_{1D}$ receptors was modeled for each of the ligands based on the in vitro binding data and previously-obtained pharmacokinetic data (FIG. 35).

This modeling made the simplifying assumption that plasma drug is freely available to the receptors mediating therapeutic benefit.

As the pharmacodynamic effect of zolmitriptan arises from the combined activities of zolmitriptan and its primary metabolite NDZ, the fractional occupancy by both ligands together was also modeled.

At the 5-$HT_{1B}$ receptor, both sumatriptan and zolmitriptan rapidly approach ~98% occupancy. Fractional occupancy peaked at ~46×KD for sumatriptan and ~35×KD for zolmitriptan/NDZ at $C_{max}$. However, occupancy by sumatriptan diminished more quickly than for zolmitriptan/NDZ so that at post-dosing times >30 min, zolmitriptan/NDZ maintained a higher and more sustained level of receptor occupancy.

At the 5-$HT_{1D}$ receptor, both sumatriptan and zolmitriptan also rapidly approach an asymptotic level of receptor occupancy of >98%, representing in the case of sumatriptan ~60×KD and in the case of zolmitriptan+NDM-zolmitriptan ~145×KD. Occupancy by sumatriptan also diminished more quickly than for zolmitriptan at this receptor subtype.

At both 5-$HT_{1B}$ and 5-$HT_{1D}$ receptors, zolmitriptan/NDZ displayed higher receptor occupancy than sumatriptan at all time points beyond 30 minutes post-dose.

Discussion and Conclusions

In patients with acute migraine, zolmitriptan administered intracutaneously using ADAM provides rapid and durable pain relief and pain freedom.

Here we have explored the role that receptor binding kinetics might play in determining the favorable pharmacokinetic and pharmacodynamic profile observed for ADAM zolmitriptan.

Zolmitriptan and NDZ had a considerably higher affinity in vitro than sumatriptan for both the 5-$HT_{1B}$ and 5-$HT_{1D}$ receptors. Affinities were similar for zolmitriptan and NDZ, suggesting that the reported differences in their potencies[1] can not be attributable to receptor binding alone.

Residence time is an important determinant of durable pharmacological effect, especially where steady-state conditions are unlikely to be met. However, the observed in vitro residence times for zolmitriptan, NDZ, and sumatriptan on both the $5\text{-}HT_{1B}$ and $5\text{-}HT_{1D}$ receptors was considerably less than the $t_{1/2}$, suggesting that residence time is unlikely to substantially influence durability of the pharmacodynamic effect.

Fast ligand-receptor on-rates are increasingly recognized as an important factor in drug persistence-of-effect.[6,7]

The $k_{on}$ was significantly (P<0.05) more rapid for zolmitriptan and NDZ than for sumatriptan on both the $5\text{-}HT_{1B}$ and $5\ HT_{1D}$ receptors.

A faster on-rate has the potential to impact the durability of response if unbound drug persists in the vicinity of receptors for a prolonged period of time. Such an effect might occur, for example, if diffusion is limited or if intact cell membranes have the potential to act as a reservoir for drug. Examples of such micro-pharmacokinetic effects have been observed for the long-acting $\beta_2$-adrenoceptor agonist drug salmeterol and phospholipid-cholecystokinin 9 (CCK-9) adducts acting at the CCK-A receptor.[6,7]

A pharmacokinetic model, based on in vitro receptor affinities and the plasma ligand concentrations determined in a phase 1 PK study[2], suggested that receptor occupancy may be sustained for a longer period of time for zolmitriptan and zolmitriptan/NDZ than for sumatriptan. This result was particularly pronounced for $5\text{-}HT_{1D}$ receptor occupancy.

This model did not account for potential micro-pharmacokinetic effects.

These data highlight interesting differences in ligand-receptor interactions for sumatriptan and zolmitriptan/NDZ that may be relevant to their different pharmacodynamic behavior in patients. However, these findings are subject to the caveat that numerous other factors not considered in this analysis also influence agonist drug behavior, including target receptor density, agonist intrinsic efficacy, and drug partitioning into the receptor biophase, any combination of which might also profoundly influence the time-course of physiological responses to the drug.

Abbreviations $K_D$: Equilibrium dissociation constant
$k_{on}$: Association rate constant (on-rate constant)
$k_{off}$: Dissociation rate constant (off-rate constant)
[L]: Ligand concentration
[R]: Free Receptor concentration
[RT]: Total Receptor concentration

REFERENCES

1. Zomig [package insert] Hayward, Calif.: Impax Pharmaceuticals; 2012.
2. Kellerman D J, Ameri M, Tepper S J. Rapid systemic delivery of zolmitriptan using an adhesive dermally applied microarray. Pain management. 2017; 7(6):559-67.
3. Spierings E L, Brandes J L, Kudrow D B, Weintraub J, Schmidt P C, Kellerman D J, et al. Randomized, double-blind, placebo-controlled, parallel-group, multi-center study of the safety and efficacy of ADAM zolmitriptan for the acute treatment of migraine. Cephalalgia: an international journal of headache. 2018; 38(2):215-24.
4. Rapoport A, Berman G, Kellerman D, Engels J, Schmidt P. Rapid Systemic Absorption of Zolmitriptan from M207 is Associated with a High Rate of Pain Relief and a Low Incidence of Moderate or Severe Pain Recurrence. The 60th Annual Scientific Meeting of the American Headache Society, Poster #PF50
5. Treatment of migraine attacks with sumatriptan. The Subcutaneous Sumatriptan International Study Group. The New England journal of medicine. 1991; 325(5):316-21.
6. Vauquelin G. Effects of target binding kinetics on in vivo drug efficacy: koff, kon and rebinding. British journal of pharmacology. 2016; 173(15):2319-34.
7. Vauquelin G. Cell membranes . . . and how long drugs may exert beneficial pharmacological activity in vivo. British journal of clinical pharmacology. 2016; 82(3):673-82.

Figure 36:
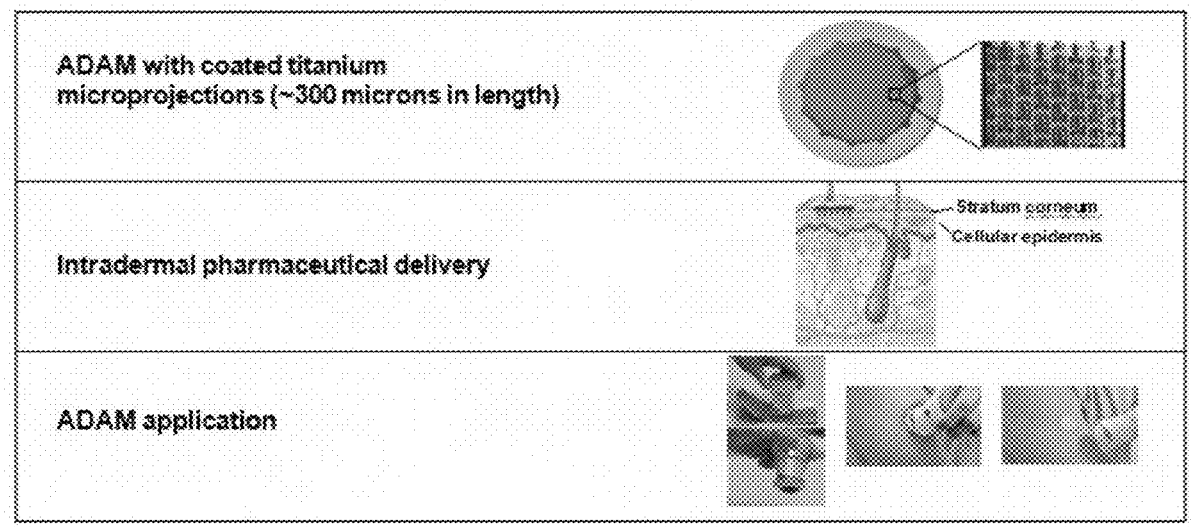
FIG. 36 depicts the ADAM—an Adhesive Dermally-Applied Microarray.

Example 9—Rapid Systemic Absorption of Zolmitriptan from M207 is Associated with a High Rate of Pain Relief and a Low Incidence of Moderate or Severe Pain Recurrence Introduction Rapid pain relief and a low incidence of pain recurrence are important attributes for acute migraine treatment. Adhesive Dermally Applied Microarray (ADAM) is an investigational system that provides intracutaneous drug administration (FIG. 36).

Figure 37:
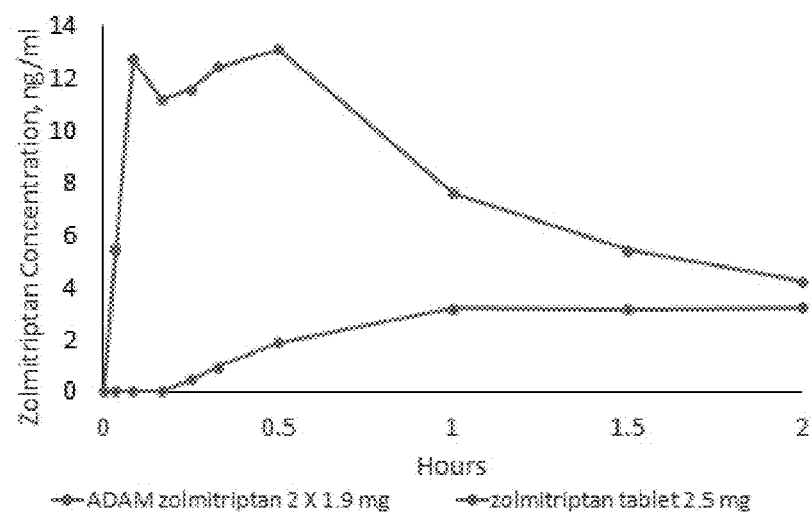
FIG. 37 is a graphic representation of zolmitriptan plasma concentration over time following delivery using ADAM or oral tablets.

In a Phase 1 study evaluating the pharmacokinetics of zolmitriptan delivered with ADAM, the median $t_{max}$ in serum was less than 20 minutes. Absorption was considerably faster than for oral zolmitriptan, with higher exposure in the first two hours (FIG. 37).[1]

In a pivotal phase 2b/3 randomized, double-blind, placebo-controlled study (ZOTRIP), ADAM zolmitriptan 3.8 mg met both co-primary endpoints (which were selected based on 2018 FDA Guidance Document for Clinical Trials Evaluating Drugs for Acute Migraine Treatment[2]) of pain freedom and freedom from patients' usual other most bothersome symptom (MBS) two hours post-dose (FIG. 38 and FIG. 39).[3,4]

As pain relief has been used as a primary endpoint in a number of prior trials in the acute treatment of migraine, we examine here the effectiveness of ADAM zolmitriptan 3.8 mg in providing pain relief in the ZOTRIP study.

We also evaluate the durability of pain relief as a function of recurrence.

Study Design and Methods a. Pivotal Efficacy Study—Conducted June 2016-February 2017

ZOTRIP was a phase 2b/3 multicenter, randomized, double-blind, placebo-controlled, parallel-group study conducted at 36 sites in the US.[3]

Eligible patients had to experience 2 to 8 migraine headaches (with or without aura) during a 28-day run-in period. See Tables 53 and 54.

TABLE 53

Patient Disposition[3]

|  | Placebo | ADAM Zolmitriptan 3.8 mg |
|---|---|---|
| Randomized | 91 | 92 |
| Safety Population | 83 (91%) | 83 (90%) |

TABLE 53-continued

Patient Disposition[3]

|  | Placebo | ADAM Zolmitriptan 3.8 mg |
|---|---|---|
| mITT Population[a] | 77 (85%) | 82 (89%) |
| Completed | 83 (91%) | 83 (90%) |

[a]Those who were randomized, treated a qualifying migraine, and had at least one post-treatment efficacy assessment

TABLE 54

Demographics and Baseline Characteristics[3]

|  | Placebo n = 77 | ADAM Zolmitriptan 3.8 mg n = 82 |
|---|---|---|
| Female | 69 (90%) | 68 (83%) |
| Age, Mean (SD) Years | 42.7 (11.5) | 41.0 (11.4) |
| Race |  |  |
| White | 59 (77%) | 67 (82%) |
| MBS |  |  |
| Nausea | 20 (26%) | 17 (21%) |
| Phonophobia | 21 (27%) | 22 (27%) |
| Photophobia | 36 (47%) | 43 (52%) |

Patients prespecified their usual most bothersome migraine-associated symptom (MBS) symptom from the following: photophobia, phonophobia, nausea.

Patients received ADAM zolmitriptan 1 mg, 1.9 mg, 3.8 mg, or placebo, in a 1:1:1:1 randomization ratio stratified by MBS.

They treated one moderate or severe headache and used an e-diary to record symptoms.

The co-primary endpoints were pain freedom and MBS freedom 2 hours post-dose.

The secondary endpoints included the proportion of patients who achieved pain relief (defined as improvement to mild or none) at 15 and 30 minutes, as well as 2, 3, and 4 hours post-dose.

Results

Figures 38, 39:
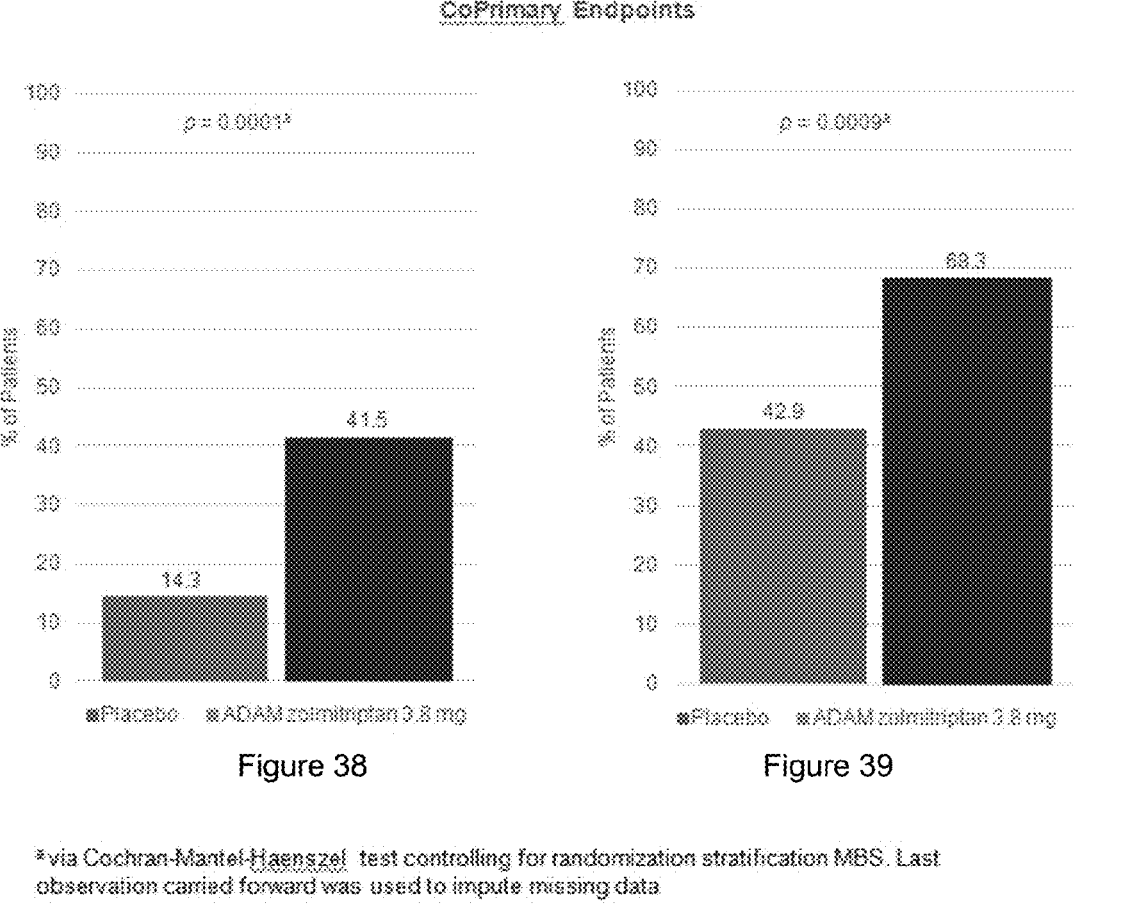
FIG. 38 is a bar graph of the pain freedom at 2 hours (mITT Population).
FIG. 39 is a bar graph of the freedom from MBS at 2 hours (mITT Population).

Results for the primary endpoints are shown in FIG. 38 and FIG. 39 and have been previously published.[3]

Results are presented here for the ADAM zolmitriptan 3.8 mg group which showed significant superiority vs placebo for the primary endpoints.

Figure 40:
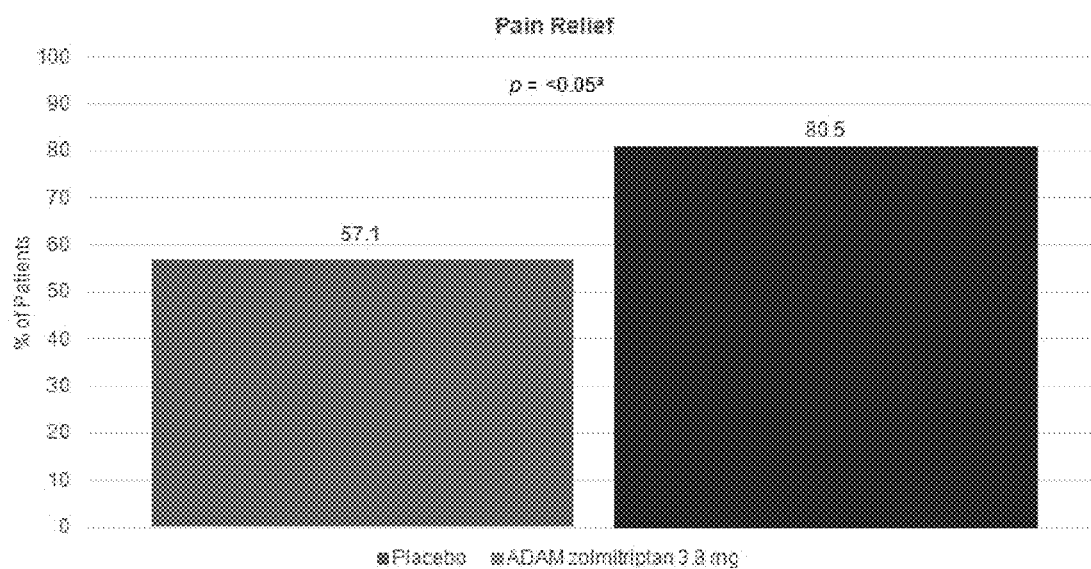
FIG. 40 is a bar graph of the pain relief at 2 hours post-dose (mITT Population).

More patients experienced pain relief in the ADAM zolmitriptan treatment group than in the placebo group (FIG. 40).

The result for this secondary endpoint was nominally significant, but not formally significant due to the fixed sequential testing methodology used in this study to control for overall type I error.

Nominally significant superiority over placebo was achieved as early as 1 hour post-dose and persisted out to 48 hours (the longest time point tested) (Table 55).

TABLE 55

Pain Relief Over Time (mITT Population)[a]

| Time Post-Dose (Hours) | Placebo n = 77 | ADAM Zolmitriptan 3.8 mg n = 82 | p Value[b] |
|---|---|---|---|
| 0.25 | 11 (14.3%) | 19 (23.2%) | 0.156 |
| 0.5 | 26 (33.8%) | 38 (46.3%) | 0.102 |

TABLE 55-continued

Pain Relief Over Time (mITT Population)[a]

| Time Post-Dose (Hours) | Placebo n = 77 | ADAM Zolmitriptan 3.8 mg n = 82 | p Value[b] |
|---|---|---|---|
| 0.75 | 35 (45.5%) | 46 (56.1%) | 0.167 |
| 1 | 41 (53.2%) | 56 (68.3%) | 0.045 |
| 2 | 44 (57.1%) | 66 (80.5%) | 0.001 |
| 3 | 40 (51.9%) | 67 (81.7%) | <0.001 |
| 4 | 40 (51.9%) | 68 (82.9%) | <0.001 |

Figure 41:
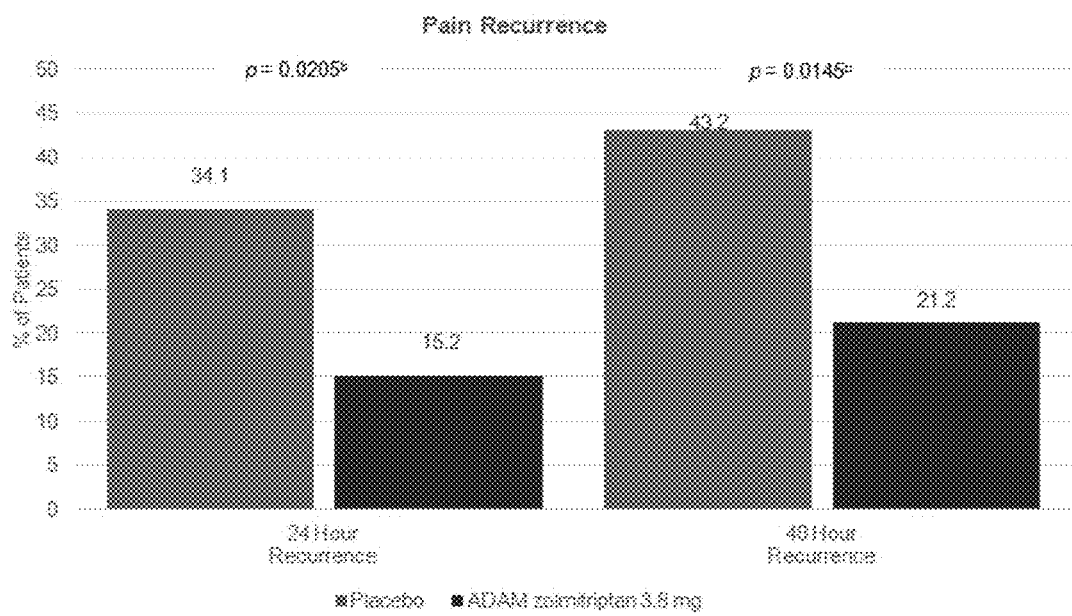
FIG. 41 is a bar graph of the pain recurrence 24 and 48 hours after pain relief (mITT Population). Pain Recurrence is defined as those who had pain relief at 2 hours and a recurrence of moderate or severe pain at the given time point.

[a]Last observation carried forward was used to impute missing data
[b]via Cochran-Mantel-Haenszel test controlling for randomization stratification MBS. This secondary endpoint not formally considered to be significant due to the fixed sequential testing methodology used in this study to control for overall type I error In a post-hoc analysis, fewer patients who received zolmitriptan 3.8 mg had pain recurrence 24 or 48 hours after achieving pain relief compared with placebo, a result that also reached nominal significance (FIG. 41).

Conclusions and Discussion

ADAM zolmitriptan provides for rapid absorption of zolmitriptan with higher 2-hour exposure than orally delivered zolmitriptan.[1]

In the pivotal ZOTRIP trial, ADAM zolmitriptan 3.8 mg was significantly superior to placebo in providing freedom from pain and MBS 2 hours post-dose.[3]

Rapid pain relief and a low incidence of pain recurrence are important attributes for the acute treatment of migraine; pain relief has been used as a primary endpoint in a number of clinical trials.

Despite the fact that a higher than expected placebo response was observed for pain relief in the ZOTRIP trial, ADAM zolmitriptan provided superior pain relief (vs placebo) as early as 1 hour post-dose.[3]

The fact that the drug-device combination is new and innovative, and that there is some sensation when the device is applied, may have led some participants to believe they were receiving the active agent, whether or not this was the case. In addition, patients were aware that three different doses of zolmitriptan were investigated, leading to a 75% probability of receiving active therapy. The odds in favor of receiving a drug that is known to be effective may have also elevated the placebo response[3,5].

Among those who had pain relief at 2 hours, the proportion of patients with pain recurrence was lower for the ADAM zolmitriptan 3.8 mg group than for the placebo group.

The fast onset of pain relief for ADAM zolmitriptan was not associated with a high rate of recurrence.

REFERENCES

1. Kellerman D J, Ameri M, Tepper S J. Rapid systemic delivery of zolmitriptan using an adhesive dermally applied microarray. Pain management. 2017.
2. Migraine: Developing Drugs for Acute Treatment Guidance for Industry. https://www.fda.gov/downloads/drugs/guidances/ucm419465.pdf
3. Spierings E L, Brandes J L, Kudrow D B, Weintraub J, Schmidt P C, Kellerman D J, et al. Randomized, double-blind, placebo-controlled, parallel-group, multi-center study of the safety and efficacy of ADAM zolmitriptan for the acute treatment of migraine. Cephalalgia: an international journal of headache. 2017:333102417737765.
4. Dodick D W, Tepper S J, Friedman D I, Schmidt P C, Kellerman D J, Gelfand A A. Use of Most Bothersome Symptom as a Coprimary Endpoint in Migraine Clinical Trials: A Post-hoc Analysis of the Pivotal ZOTRIP Randomized, Controlled Trial. Headache. 2018 May 21 [Epub ahead of print].

5. Geraud G, Olesen J, Pfaffenrath V, Tfelt-Hansen P, Zupping R, Diener H C, et al. Comparison of the efficacy of zolmitriptan and sumatriptan: issues in migraine trial design. Cephalalgia: an international journal of headache. 2000; 20 (1):30-8.

The embodiments of the invention described above are intended to be merely exemplary; numerous variations and modifications will be apparent to those skilled in the art. All such variations and modifications are intended to be within the scope of the present invention as defined in any appended claim.

We claim:

1. A method for treating migraine in a patient in need thereof, comprising intracutaneously administering about 3.8 mg zolmitriptan using an adhesive dermally-applied microarray (ADAM) comprising a plurality of microprojections coated with the zolmitriptan, the microprojections adapted to penetrate or pierce the stratum corneum of the patient, wherein the method provides rapid and durable pain relief and pain freedom and wherein zolmitriptan has a pharmacodynamic effect that arises from combined activities of zolmitriptan and its primary metabolite N-desmethyl zolmitriptan (NDZ).

2. The method of claim 1, wherein the patient is pain-free at 2 hours post-dose and does not have migraine recurrence within 24 hours post-dose.

3. The method of claim 1, wherein on-rate constant ($k_{on}$) is 6 to 10 times faster for zolmitriptan and NDZ than for sumatriptan on both the $5\text{-HT}_{1B}$ and $5\text{-HT}_{1D}$ receptors based on in vitro binding data.

4. The method of claim 3, wherein the on-rate constant ($k_{on}$) for zolmitriptan on $5\text{-HT}_{1B}$ receptors is about 0.053 $nM^{-1}min^{-1}$ and the on-rate constant ($k_{on}$) for zolmitriptan on $5\text{-HT}_{1D}$ receptors is about 0.174 $nM^{-1}min^{-1}$ based on in vitro binding data.

5. The method of claim 3, wherein equilibrium dissociation constant ($K_D$) of zolmitriptan on $5\text{-HT}_{1B}$ receptors is about 1.47 nM and equilibrium dissociation constant ($K_D$) of zolmitriptan on $5\text{-HT}_{1D}$ receptors is about 0.34 nM based on in vitro binding data.

6. The method of claim 3, wherein on-rate constant ($k_{on}$) of NDZ on $5\text{-HT}_{1B}$ receptors is about 0.054 $nM^{-1}min^{-1}$ and on-rate constant ($k_{on}$) of NDZ on $5\text{-HT}_{1D}$ receptors is about 0.126 $nM^{-1}min^{-1}$ based on in vitro binding data.

7. The method of claim 3, wherein equilibrium dissociation constant ($K_D$) of NDZ on $5\text{-HT}_{1B}$ receptors is about 0.92 nM and equilibrium dissociation constant ($K_D$) of NDZ on $5\text{-HT}_{1D}$ receptors is about 0.43 nM based on in vitro binding data.

8. The method of claim 1, wherein zolmitriptan and NDZ have higher affinity than sumatriptan for $5\text{-HT}_{1B}$ and $5\text{-HT}_{1D}$ receptors based on in vitro binding data.

9. The method of claim 8, wherein the affinities of zolmitriptan and NDZ for both $5\text{-HT}_{1B}$ and $5\text{-HT}_{1D}$ receptors are similar based on in vitro binding data.

10. The method of claim 1, wherein zolmitriptan rapidly approaches about 98% occupancy at $5\text{-HT}_{1B}$ receptors and rapidly approaches an asymptotic level of receptor occupancy of greater than about 98% at $5\text{-HT}_{1D}$ receptors based on in vitro binding data.

11. The method of claim 10, wherein occupancy by sumatriptan diminishes quicker than occupancy by zolmitriptan/NDZ at $5\text{-HT}_{1B}$ and at $5\text{-HT}_{1D}$ receptors based on in vitro binding data.

12. The method of claim 11, wherein zolmitriptan/NDZ maintain a higher and more sustained level of receptor occupancy than sumatriptan at $5\text{-HT}_{1B}$ receptors based on in vitro binding data.

13. The method of claim 10, wherein at $5\text{-HT}_{1B}$ and $5\text{-HT}_{1D}$ receptors, zolmitriptan/NDZ display higher receptor occupancy than sumatriptan at all time points beyond 30 minutes post-dose based on in vitro binding data.

14. The method of claim 1, wherein fractional occupancy peaks at about 35xKD for zolmitriptan/NDZ at $C_{max}$ at $5\text{-HT}_{1B}$ receptors and fractional occupancy peaks about 145xKD for zolmitriptan+NDM-zolmitriptan at $C_{max}$ at $5\text{-HT}_D$ receptors based on in vitro binding data.

15. The method of claim 1, wherein observed in vitro residence times for zolmitriptan, NDZ, and sumatriptan on both $5\text{-HT}_{1B}$ and $5\text{-HT}_{1D}$ receptors are considerably less than elimination half life ($t_{1/2}$).

16. The method of claim 1, wherein time-course of physiological responses to zolmitriptan is affected by ligand-receptor interactions for zolmitriptan/NDZ, target receptor density, agonist intrinsic efficacy, and drug partitioning into receptor biophase, or any combination thereof.

17. A method for treating migraine in a patient in need thereof, comprising intracutaneously administering about 3.8 mg zolmitriptan using an adhesive dermally-applied microarray (ADAM) comprising a plurality of microprojections coated with the zolmitriptan, the microprojections adapted to penetrate or pierce the stratum corneum of the patient, wherein the method provides rapid absorption of zolmitriptan with higher 2-hour exposure than orally delivered zolmitriptan.

18. The method of claim 17, wherein zolmitriptan is associated with a high rate of pain relief and a low incidence of moderate or severe pain recurrence for migraine treatment.

19. The method of claim 1, wherein the about 3.8 mg zolmitriptan is administered by two microarrays each comprising about 1.9 mg zolmitriptan.

20. A method for treating migraine in a patient in need thereof, comprising the steps of:
 (a) providing a composition comprising 3.8 mg zolmitriptan, and
 (b) intracutaneously administering the composition comprising the zolmitriptan using an adhesive dermally-applied microarray (ADAM) comprising a plurality of microprojections coated with the zolmitriptan, the microprojections adapted to penetrate or pierce the stratum corneum of the patient,
 wherein the method results in pain relief, pain freedom, reduction in most bothersome migraine-associated symptoms (MBS), or a combination thereof.

21. The method of claim 20, wherein when the treatment is administered to a population of patients, the treatment results in at least one of the following outcomes:
 (a) about 23.2% of the patients achieve pain relief at 0.25 hour post-dose,
 (b) about 46.3% of the patients achieve pain relief at 0.5 hour post-dose,
 (c) about 56.1% of the patients achieve pain relief at 0.75 hour post-dose,
 (d) about 68.3% of the patients achieve pain relief at 1 hour post-dose,
 (e) about 80.5% of the patients achieve pain relief at 2 hours post-dose,
 (f) about 81.7% of the patients achieve pain relief at 3 hours post-dose, (g) about 82.9% of the patients achieve pain relief at 4 hours post-dose,
(h) about 41.5% of the patients achieve pain freedom at 2 hours post-dose,
(i) about 68.3% of the patients achieve freedom from MBS at 2 hours post-dose,
(j) about 15.2% of the patients have pain recurrence 24 hours after achieving pain relief,
(k) about 21.2% of the patients have pain recurrence 48 hours after achieving pain relief, and
(l) fast onset of pain relief that is not associated with a high rate of recurrence.

* * * * *